United States Patent
Ichiyanagi et al.

(10) Patent No.: US 11,879,149 B2
(45) Date of Patent: Jan. 23, 2024

(54) QUANTIFICATION METHOD OF ETHANOLAMINE PHOSPHATE, OXIDOREDUCTASE FOR QUANTIFICATION, COMPOSITION FOR QUANTIFICATION, KIT FOR QUANTIFICATION AND SENSOR FOR QUANTIFICATION

(71) Applicant: KIKKOMAN CORPORATION, Noda (JP)

(72) Inventors: Atsushi Ichiyanagi, Noda (JP); Yosuke Masakari, Noda (JP); Haruka Hiraguchi, Noda (JP)

(73) Assignee: KIKKOMAN CORPORATION, Noda (JP)

(*) Notice: Subject to any disclaimer, the term of this patent is extended or adjusted under 35 U.S.C. 154(b) by 61 days.

(21) Appl. No.: 17/345,187

(22) Filed: Jun. 11, 2021

(65) Prior Publication Data

US 2021/0310043 A1 Oct. 7, 2021

Related U.S. Application Data

(63) Continuation of application No. PCT/JP2019/048963, filed on Dec. 13, 2019.

(30) Foreign Application Priority Data

Dec. 13, 2018 (JP) ................. 2018-233440

(51) Int. Cl.
*C12Q 1/26* (2006.01)
*C12Q 1/52* (2006.01)
*C12N 9/06* (2006.01)

(52) U.S. Cl.
CPC ............ *C12Q 1/52* (2013.01); *C12N 9/0022* (2013.01); *C12N 9/0032* (2013.01); *C12Q 1/26* (2013.01)

(58) Field of Classification Search
CPC ........... C12Q 1/52; C12Q 1/26; C12N 9/0022
See application file for complete search history.

(56) References Cited

U.S. PATENT DOCUMENTS

| 5,089,393 A | 2/1992 | Imamura |
| 5,206,147 A | 4/1993 | Hoenes |

(Continued)

FOREIGN PATENT DOCUMENTS

| EP | 0901018 A2 | 3/1999 |
| GB | 2103607 A | 2/1983 |

(Continued)

OTHER PUBLICATIONS

Ohta et al., Int J Anal Bio-Sci, 2016, 4(4):110-116.*

(Continued)

*Primary Examiner* — Erin M. Bowers
(74) *Attorney, Agent, or Firm* — ROSSI, KIMMS & McDOWELL LLP

(57) ABSTRACT

There is provided a novel quantification method for quantifying a concentration of EAP, which is a biomarker of depression, an enzyme for quantitation, a composition for quantitation, a kit for quantitation or a sensor for quantitation. There is provided a quantification method of ethanolamine phosphate by adding oxidoreductase to a sample containing ethanolamine phosphate. A mediator may be reduced by adding the oxidoreductase, and the reduced mediator may be reacted with a reagent to determine a concentration of ethanolamine phosphate. In addition, hydrogen peroxide produced by adding the oxidase as the oxidoreductase may be reacted with a reagent to determine a concentration of the ethanolamine phosphate.

7 Claims, 9 Drawing Sheets

Specification includes a Sequence Listing.

(56) References Cited

U.S. PATENT DOCUMENTS

| 8,003,359 | B2 | 8/2011 | Hirokawa |
| 9,631,224 | B2* | 4/2017 | Ohga ................. C12Q 1/32 |
| 2001/0006150 | A1 | 7/2001 | Taniike |
| 2009/0011508 | A1 | 1/2009 | Takahashi |
| 2012/0282592 | A1 | 11/2012 | Kawamura |
| 2015/0366491 | A1 | 12/2015 | Boock et al. |
| 2016/0208310 | A1 | 7/2016 | Ohga |

FOREIGN PATENT DOCUMENTS

| JP | S589698 A | 1/1983 |
| JP | S5898096 A | 6/1983 |
| JP | H02174695 A | 7/1990 |
| JP | H1142098 A | 2/1999 |
| JP | 2001183330 A | 7/2001 |
| JP | 2007089538 A | 4/2007 |
| JP | 2007222055 A | 9/2007 |
| WO | 2007125779 A1 | 11/2007 |
| WO | 2011019072 A1 | 2/2011 |
| WO | 2013069645 A1 | 5/2013 |
| WO | 2018062204 A1 | 4/2018 |

OTHER PUBLICATIONS

Extended European Search Report issued in European Appln. No. 19894878.8 dated Aug. 1, 2022.
Tanizawa "Cloning and Sequencing of Phenylethylamine Oxidase from Arthrobacter globiformis and Implication of Tyr-382 as the Precursor to Its Covalently Bound Quinone Cofactor", Biochemical and Biophysical Research Communications. Mar. 30, 1994: pp. 1096-1102. vol. 199, No. 3.
A0a068s1q5: "Amine oxidase" Oct. 1, 2014. Retrieved on Jul. 13, 2022, URL:https://rest.uniprot.org/uniprotkb/A0A068S1Q5.txt.
A0a077w728: "Amine oxidase", Oct. 29, 2014. Retrieved on Jul. 13, 2022, URL:https://rest.uniprot.org/uniprotkb/A0A077W728.txt.
A0a1x2hwf3: "Amine oxidase", Jul. 5, 2017. Retrieved on Jul. 13, 2022, URL:https://uniprot.org/uniprotkb/A0A1X2HWF3.txt.
A0a1x2hwh0: "Amine oxidase", Jul. 5, 2017. Retrieved on Jul. 13, 2022, URL:https://rest.uniprot.org/uniprotkb/A0A1X2HWH0.txt.
Database JPO Proteins [Online] "JP 2014233219-A/11: Ethanolamine oxidase.", Retrieved from EBI accession No. JPOP:DL932318. Mar. 24, 2015. Database accession No. DL932318.
English translation of Written Opinion issued in Intl. Appln. No. PCT/JP2019/048963 dated Mar. 10, 2020, previously cited in IDS filed Jun. 11, 2021.
Kawamura. "Plasma metabolome analysis of patients with major depressive disorder." Psychiatry and Clinical Neurosciences. 2018: 349-361. vol. 72.
Gietz. "Transforming yeast with DNA." Methods in Molecular and Cellular Biology. 1995: 255-269. vol. 5.
Pribylova. "Efficient transformation of the osmotolerant yeast Zygosaccharomyces rouxii by electroporation." Journal of Microbiological Methods. 2003: 481-484. vol. 55.
Unkles. "The development of a homologous transformation system for Aspergillus oryzae based on the nitrate assimilation pathway: A convenient and general selection system for filamentous fungal transformation." Molecular and General Genetics. 1989: 99-104. vol. 218.
Ozeki. "A Method for the Re-isolation of an Autonomously Replicating Plasmid from Aspergillus Transformants." Bioscience, Biotechnology, and Biochemistry. 1995: 1133-1134. vol. 59, No. 6.
International Search Report issued in Intl. Appln. No. PCT/JP2019/048963 dated Mar. 10, 2020. English translation provided.
Written Opinion issued in Intl. Appln. No. PCT/JP2019/048963 dated Mar. 10, 2020.
Bruggemann. "Enzymes and genes of taurine and isethionate dissimilation in Paracoccus denitrificans." Microbiology. 2004: 805-816. vol. 150.
Definition: "putative taurine dehydrogenase large subunit [*Paracoccus denitrificans*]". Database DDBJ/EMBL/GenBank [online], uploaded: Jul. 26, 2016, Accession No. AAS78784. [https://www.ncbi.nlm.nih.gov/protein/AAS78784.1/].
OTA. "Enzymatic Characterization of an Amine Oxidase from *Arthrobacter* sp. Used to Measure Phosphatidylethanolamine." Bioscience, Biotechnology, and Biochemistry. 2008: 2732-2738. vol. 72, No. 10.
Hirano. "Syncephalastrum racemosum amine oxidase with high catalytic efficiency toward ethanolamine and its application in ethanolamine determination." Applied Microbiology and Biotechnology. 2016: 3999-4013. vol. 100, No. 9.
Office Action issued in Chinese Appln. No. 201980081434.X, dated Aug. 20, 2023. English machine translation provided.
Office Action issued in Japanese Appln. No. 2020-559338 dated Oct. 17, 2023. English machine translation provided.

* cited by examiner

QUANTIFICATION METHOD OF ETHANOLAMINE PHOSPHATE, OXIDOREDUCTASE FOR QUANTIFICATION, COMPOSITION FOR QUANTIFICATION, KIT FOR QUANTIFICATION AND SENSOR FOR QUANTIFICATION

CROSS-REFERENCE TO RELATED APPLICATIONS

This application is based upon and claims the benefit of priority from the prior Japanese Patent Application No. 2018-233440, filed on Dec. 13, 2018, and PCT Application No. PCT/JP2019/048963, filed on Dec. 13, 2019, the entire contents of which are incorporated herein by reference.

The instant application contains a Sequence Listing which has been submitted in ASCII format via EFS-Web and is hereby incorporated by reference in its entirety. Said ASCII copy, created on Jul. 5, 2023, is named "TAKA-0017US1_NFOA1_AmendedSequence_List" and is 81959 bytes in size.

FIELD

The present invention relates to a quantification method of ethanolamine phosphate, oxidoreductase for quantitation, a composition for quantitation, a kit for quantitation and sensor for quantitation.

BACKGROUND

Ethanolamine phosphate (EAP) is contained in human blood. International patent publication No. 2011/019072 describes that EAP is a biomarker for diagnosing depression. Kawamura N, "Plasma metabolome analysis of patients with major depressive disorder." Psychiatry Clin Neurosci. 2018 May; 72(5):349-361 describes that it is possible to diagnose the depression with a concentration of EAP of 1.5 μM or less as a reference value.

In addition, International patent publication No. 2013/069645 describes a method for measuring a concentration of EAP using an EAP phospholyase and an acetaldehyde dehydrogenase.

SUMMARY

As a measurement method of the concentration of EAP other than the method disclosed in International patent publication No. 2013/069645 has not been reported so far, development of a novel measurement method is desired.

An aim of the present invention is to provide a novel quantification method for quantifying a concentration of EAP, which is a biomarker of depression, an enzyme for quantitation, a composition for quantitation, a kit for quantitation or a sensor for quantitation.

According to an embodiment of the present invention, there is provided a quantification method of ethanolamine phosphate by adding oxidoreductase to a sample containing ethanolamine phosphate.

A mediator may be reduced by adding the oxidoreductase, and the reduced mediator may be reacted with a reagent to determine a concentration of ethanolamine phosphate.

According to an embodiment of the present invention, there is provided oxidoreductase used in the quantification method of ethanolamine phosphate.

The oxidoreductase may be an oxidoreductase belonged to EC NO: 1.4 or EC NO: 1.5.

The oxidoreductase belonged to EC NO: 1.4 or EC NO: 1.5 may be selected from primary amine dehydrogenase, monoamine dehydrogenase, diamine dehydrogenase, polyamine dehydrogenase, ethanolamine dehydrogenase, tyramine dehydrogenase, phenylethylamine dehydrogenase, benzylamine dehydrogenase, histamine dehydrogenase, serotonin dehydrogenase, spermine dehydrogenase, spermidine dehydrogenase, β-alanine dehydrogenase, gamma-aminobutyric acid (GABA) dehydrogenase, taurine dehydrogenase, cadaverine dehydrogenase, cadaverine dehydrogenase, and acyl dehydrogenase.

The taurine dehydrogenase may include a large subunit.

The oxidoreductase belonged to EC NO: 1.4 or EC NO: 1.5 may be oxidase belonged to EC NO: 1.4.3 or EC NO: 1.5.3.

The oxidase may be an oxidase selected from primary amine oxidase, monoamine oxidase, diamine oxidase, polyamine oxidase, ethanolamine oxidase, tyramine oxidase, phenylethylamine oxidase, benzylamine oxidase, histamine oxidase, serotonin oxidase, spermine oxidase, spermidine oxidase, β-alanine oxidase, γ-aminobutyric acid (GABA) oxidase, taurine oxidase, cadaverine oxidase, agmatine oxidase.

According to an embodiment of the present invention, there is provided a composition for a quantification of ethanolamine phosphate including any of oxidoreductases described above.

The composition for the quantification of ethanolamine phosphate may comprise a mediator which is reduced by adding oxidoreductase and a reagent which reacts with the reduced mediator.

According to an embodiment of the present invention, there is provided a kit for the quantification of ethanolamine phosphate including oxidoreductase of any of the above, a mediator which is reduced by adding oxidoreductase, and a reagent which reacts with the reduced mediator.

In the method for the quantification of ethanolamine phosphate described above, oxidoreductase may be an oxidase, and hydrogen peroxide produced by adding the oxidase may be reacted with a reagent to determine a concentration of the ethanolamine phosphate.

According to an embodiment of the present invention, there is provided an oxidase used as the oxidoreductase in the method for the quantification of ethanolamine phosphate.

The oxidase may be an oxidase belonged to EC NO: 1.4.3 or EC NO: 1.5.3.

The oxidase may be an oxidase selected from primary amine oxidase, monoamine oxidase, diamine oxidase, polyamine oxidase, ethanolamine oxidase, tyramine oxidase, phenylethylamine oxidase, benzylamine oxidase, histamine oxidase, serotonin oxidase, spermine oxidase, spermidine oxidase, β-alanine oxidase, γ-aminobutyric acid (GABA) oxidase, taurine oxidase, cadaverine oxidase, and agmatine oxidase.

According to an embodiment of the present invention, there is provided a composition for the quantification of ethanolamine phosphate including oxidase of any of the above.

The composition for the quantification of ethanolamine phosphate may include a reagent which reacts with hydrogen peroxide produced by adding the oxidase.

According to an embodiment of the present invention, there is provided a kit for the quantification of ethanolamine phosphate including the oxidase of any of the above and a reagent which reacts with hydrogen peroxide produced by adding the oxidase.

According to an embodiment of the present invention, there is provided an electrode including the oxidoreductase according to any of the above, or the oxidase according to any of the above.

According to an embodiment of the present invention, there is provided a sensor chip including the electrode as a working electrode.

According to an embodiment of the present invention, there is provided a sensor including the sensor chip.

REFERENCE SIGNS LIST

Figure 1:
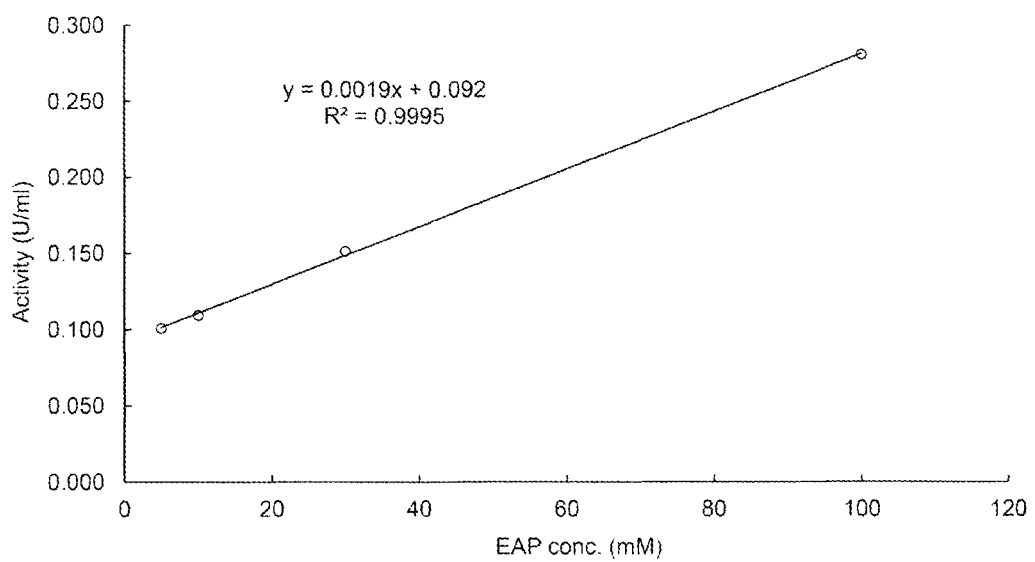
FIG. 1 shows a correlation between a concentration of EAP and an enzyme activity (U/ml) according to an example of the present invention.

1: working electrode, 3: counter electrode, 5: reference electrode, 7: wiring unit, 9: terminal, 10: sensor chip, 11: substrate, 13: spacer, 15: cover, 19: reaction layer, 30: measuring unit, 31: switch, 33: display, 100: sensor, 110: control unit, 120: display unit, 130: input unit, 140: storage unit, 150: communication unit, 160: power supply, 190: wiring

DESCRIPTION OF EMBODIMENT

Hereafter, a novel quantification method for quantifying a concentration of EAP, which is a biomarker of depression, an enzyme for quantification, a composition for quantification, a kit for quantitation and sensor for quantitation according to the present invention are described. However, the novel quantitation method for quantifying the concentration of EAP, which is a biomarker of depression, the enzyme for quantification, the composition for quantification, the kit for quantification and the sensor for quantitation according to the present invention should not be construed as being limited to the description of the following embodiments and examples.

In an embodiment, oxidoreductase used in the present invention is a dehydrogenase which acts on EAP as a substrate. It is considered that EAP dehydrogenase can be most preferably used as oxidoreductase used in the present invention. However, by the time of filing the present application, EAP dehydrogenase has not been identified.

Therefore, dehydrogenase which efficiently acts on a substrate, having an analogous structure to EAP can be used as an alternative to oxidoreductase used in the present invention. The analogous structure refers to a physicochemical structure which is considered to be similar from structural, electronic, stereochemical viewpoints, and the like.

For example, the substrate structurally similar to EAP includes a substrate containing $CH-NH_2$ or $CH-NH$ bonds, and examples of the enzyme for the substrate includes oxidoreductases belonging to EC NO: 1.4 or EC NO: 1.5.

For example, the oxidoreductase belonging to EC NO: 1.4 or EC NO: 1.5 includes primary amine dehydrogenase, monoamine dehydrogenase, diamine dehydrogenase, polyamine dehydrogenase, ethanolamine dehydrogenase, tyramine dehydrogenase, phenylethylamine dehydrogenase, benzylamine dehydrogenase, histamine dehydrogenase, serotonin dehydrogenase, spermine dehydrogenase, spermidine dehydrogenase, β-alanine dehydrogenase, γ-aminobutyric acid (GABA) dehydrogenase, taurine dehydrogenase, cadaverine dehydrogenase, agmatine dehydrogenase. In particular, the substrate structurally similar to EAP includes taurine, and taurine dehydrogenase (TDH) can be suitably used as dehydrogenase for the substrate.

The oxidoreductase used in the present invention may be a multimer or a monomer. For example, when only a certain subunit (monomer) among several subunits constituting the oxidoreductase, which is a multimer, catalyzes a dehydrogenation reaction in which hydrogen is taken from a substrate to a hydrogen acceptor, the oxidoreductase used in the present invention may be a multimer or the subunit (monomer).

More specifically, the TDH used in the present invention has a large subunit (LaTDH) having a base sequence of SEQ ID NO: 2 and a small subunit (SmTDH) having a base sequence of SEQ ID NO: 4 and catalyzes a dehydrogenation reaction in which hydrogen is taken from the substrate to the hydrogen acceptor not only with a the multimer having LaTDH and SmTDH, but also only with LaTDH. Therefore, the TDH used in the present invention may have both of LaTDH and SmTDH, or only LaTDH.

Oxidoreductase belonging to EC NO: 1.4 or EC NO: 1.5 may be an oxidase belonging to EC NO: 1.4.3 or EC NO: 1.5.3.

For example, the oxidase belonging to EC NO: 1.4.3 or EC NO: 1.5.3 includes primary amine oxidase, monoamine oxidase, diamine oxidase, polyamine oxidase, ethanolamine oxidase, tyramine oxidase, phenylethylamine oxidase, benzylamine oxidase, histamine oxidase, serotonin oxidase, spermine oxidase, spermidine oxidase, β-alanine oxidase, γ-aminobutyric acid (GABA) oxidase, taurine oxidase, cadaverine oxidase, and agmatine oxidase. In particular, phenylethylamine oxidase (PEAOX) can be suitably used.

As the reaction condition of oxidoreductase used in the present invention, any condition may be available as long as it is a condition for acting on EAP and efficiently catalyzing an oxidation reaction. An enzyme generally has an optimum temperature and optimum pH which show the highest activity. Therefore, the reaction conditions are preferably near the optimum temperature and the optimum pH. For example, the reaction conditions of TDH can be suitably used at a temperature of 30° C. and pH 8.5, which will be described later, but is not limited thereto. Further, for example, the reaction conditions of PEAOX can be suitably used at a temperature of 37° C. and pH 8.5, which will be described later, but is not limited thereto.

The oxidoreductase of the present invention may be an oxidoreductase produced by a naturally occurring microorganism or an oxidoreductase produced by a transformed microorganism. From the viewpoint of efficient mass expression of the enzyme, the enzyme can be efficiently expressed in large quantities by using the transformed microorganism.

The microorganism from which the oxidoreductase of the present invention is derived includes, the genus *Paracoccus*, the genus *Methylarcula*, the genus *Martelella*, the genus *Rhodobacter*, the genus *Roseobacter*, the genus *Gemmobacter*, the genus *Arthrobacter*, the genus *Paenarthrobacter*, the genus *Pseudarthrobacter*, the genus *Cryobacterium*, the genus *Bacillus*, the genus *Sinomonas*, the genus *Tersicoccus*, the genus *Kocuria*, the genus *Micrococcus*, the genus *Brevibacterium*, the genus *Zhihengliuella*, the genus *Citricoccus*, the genus *Geodematophilus*, the genus *Rhodococcus*, the genus *Amycolatopsis*, the genus *Nocardia*, the genus *Modestobacter*, the genus *Glutamincibacter*, the genus *Psudonocardia*, the genus *Gordonia*, the genus *Streptomyces*, the genus *Geodermatophilus*, the genus *Cellulomonas*, the genus *Mycobacterium*, the genus *Mycolicibacterium*, the genus *Psudoglutamicibacter*, the genus *Corynebacterium*, the genus *Nocardiopsis*, the genus *Nonomuraea*, the genus *Saccharomonospora*, the genus *Prauserella*, the genus *Amnibacterium*, the genus *Actinobacteria*, the genus *Saccharopolyspora*, the genus *Leifsonia*, the genus *Agromyces*, the genus *Streptacidiphilus*, the genus *Xylanimonas*, the genus *Tsukamurella*, the genus *Williamsia*, the genus *Asanoa*, the genus *Plantactinospora*, the genus *Salinispora*, the genus *Agreia*, the genus *Cryocola*, the genus *Curtobacterium*, the genus *Murinocardiopsis*, the genus *Subtercola*, the genus *Microbispora*, the genus *Jiangella*, the genus *Blastococcus*, the genus *Actinomadura*, the genus *Actinoplanes*, the genus *Catenulispora*, the genus *Lichtheimia*, and the genus *Syncephalastrum* can be suitably used, but are not limited thereto.

For example, although the oxidoreductase of the present invention may be TDH produced by *Paracoccus denitrificans* or TDH produced by *E. coli* transformed with a plasmid containing a TDH gene derived from *Paracoccus denitrificans*, oxidoreductase can be efficiently expressed in large quantities by using the *E. coli* transformed with the plasmid containing a TDH gene derived from *Paracoccus denitrificans*.

Also, for example, although the oxidoreductase of the present invention may be a PEAOX produced by *Arthrobacter globiformis* or a PEAOX produced by *E. coli* transformed with a plasmid containing a PEAOX gene derived from *Arthrobacter globiformis*, oxidoreductase can be efficiently expressed in large quantities by using the *E. coli* transformed with the plasmid containing a PEAOX gene derived from *Arthrobacter globiformis*.

Also, for example, although the oxidoreductase of the present invention may be amine oxidase (LcAOX) produced by *Lichtheimia corymbifera* or amine oxidase produced by *E. coli* transformed with a plasmid containing an LcAOX gene having a base sequence of SEQ ID NO: 16 derived from *Lichtheimia corymbifera*, oxidoreductase can be efficiently expressed in large quantities by using the *E. coli* transformed with the plasmid containing the LcAOX gene derived from *Lichtheimia corymbifera*.

Also, for example, although the oxidoreductase of the present invention may be hypothetical protein (LrHP) produced by *Lichtheimia ramosa* or hypothetical protein produced by *E. coli* transformed with a plasmid containing an LrHP gene having a base sequence of SEQ ID NO: 21 derived from *Lichtheimia ramosa*, oxidoreductase can be efficiently expressed in large quantities by using the *E. coli* transformed with the plasmid containing the LrHP gene derived from *Lichtheimia ramosa*.

Also, for example, although the oxidoreductase of the present invention may be amine oxidase (SrAOX3925) produced by *Syncephalastrum racemosum* or amine oxidase produced by *E. coli* transformed with a plasmid containing an SrAOX3925 gene having a base sequence of SEQ ID NO: 26 derived from *Syncephalastrum racemosum*, oxidoreductase can be efficiently expressed in large quantities by using the *E. coli* transformed with the plasmid containing the SrAOX3925 gene derived from *Syncephalastrum racemosum*.

Also, for example, although the oxidoreductase of the present invention may be amine oxidase (SrAOX3926) produced by *Syncephalastrum racemosum* or amine oxidase produced by *E. coli* transformed with a plasmid containing an SrAOX3926 gene having a base sequence of SEQ ID NO: 31 derived from *Syncephalastrum racemosum*, oxidoreductase can be efficiently expressed in large quantities by using the *E. coli* transformed with the plasmid containing the SrAOX3926 gene derived from *Syncephalastrum racemosum*.

Also, for example, although the oxidoreductase of the present invention may be ethanolamine oxidase (SrEAOX) produced by *Syncephalastrum racemosum* or ethanolamine oxidase produced by *E. coli* transformed with a plasmid containing an SrEAOX gene having a base sequence of SEQ ID NO: 36 derived from *Syncephalastrum racemosum*, oxidoreductase can be efficiently expressed in large quantities by using the *E. coli* transformed with the plasmid containing the SrEAOX gene derived from *Syncephalastrum racemosum*.

In an embodiment, the oxidoreductase of the present invention includes oxidoreductase which has high sequence identity (e.g., 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, and 99% or more) relative to an amino acid sequence (SEQ ID NO: 1) of LaTDH produced by *Paracoccus denitrificans* and oxidoreductase having an amino acid sequence in which 1 or more amino acids have been altered or varied, deleted, substituted, added and/or inserted in the amino acid sequence of SEQ ID NO: 1.

In an embodiment, the oxidoreductase of the present invention includes oxidoreductase which has high sequence identity (e.g., 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, and 99% or more) relative to an amino acid sequence (SEQ ID NO: 9) of PEAOX produced by *Arthrobacter globiformis*, and oxidoreductase having an amino acid sequence in which 1 or more amino acids are altered or varied, deleted, substituted, added and/or inserted in the amino acid sequence of SEQ ID NO: 9.

In an embodiment, the oxidoreductase of the present invention includes oxidoreductase which has high sequence identity (e.g., 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, and 99% or more) relative to an amino acid sequence (SEQ ID NO: 15) of LcAOX produced by *Lichtheimia corymbifera*, and oxidoreductase having an amino acid sequence in which 1 or more amino acids are altered or varied, deleted, substituted, added and/or inserted in the amino acid sequence of SEQ ID NO: 15.

In an embodiment, the oxidoreductase of the present invention includes oxidoreductase which has high sequence identity (e.g., 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, and 99% or more) relative to an amino acid sequence (SEQ ID NO: 20) of LrHP produced by *Lichtheimia ramosa*, and oxidoreductase having an amino acid sequence in which 1 or more amino acids are altered or varied, deleted, substituted, added and/or inserted in the amino acid sequence of SEQ ID NO: 20.

In an embodiment, the oxidoreductase of the present invention includes oxidoreductase which has high sequence identity (e.g., 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, and 99% or more) relative to an amino acid sequence (SEQ ID NO: 25) of SrAOX3925 produced by *Syncephalastrum racemosum*, and oxidoreductase having an amino acid sequence in which 1 or more amino acids are altered or varied, deleted, substituted, added and/or inserted in the amino acid sequence of SEQ ID NO: 25.

In an embodiment, the oxidoreductase of the present invention includes oxidoreductase which has high sequence identity (e.g., 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, and 99% or more) relative to an amino acid sequence (SEQ ID NO: 30) of SrAOX3926 produced by *Syncephalastrum racemosum*, and oxidoreductase having an amino acid sequence in which 1 or more amino acids are altered or varied, deleted, substituted, added and/or inserted in the amino acid sequence of SEQ ID NO: 30.

In an embodiment, the oxidoreductase of the present invention includes oxidoreductase which has high sequence identity (e.g., 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, and 99% or more) relative to an amino acid sequence (SEQ ID NO: 35) of SrEAOX produced by *Syncephalastrum racemosum*, and oxidoreductase having an amino acid sequence in which 1 or more amino acids are altered or varied, deleted, substituted, added and/or inserted in the amino acid sequence of SEQ ID NO: 35.

(Amino Acid Sequence Identity)

Amino acid sequence identity can be calculated by programs such as maximum matching or search homology of GENETYX (registered trademark) (GENETYX CORPORATION), or maximum matching or multiple alignment of DNASIS (registered trademark) Pro (Hitachi Solutions, Ltd.), or multiple alignment of CLUSTAL W. When the amino acid sequences of 2 or more oxidoreductases are aligned in order to calculate the amino acid sequence identity, a position of the amino acid which is identical in the 2 or more oxidoreductases can be examined. An identical region in the amino acid sequence can be determined based on such information. Here, with respect to two or more amino acid sequences, percent identity refers to a percentage with the total number of amino acids in the region where the amino acids can be aligned as a denominator and the number of positions occupied by the identical amino acid as a numerator when the two or more amino acid sequences are aligned using algorithms such as Blosum62. Therefore, in general, when there is a region in which no identity is found in two or more amino acid sequences, for example, when an additional sequence in which no identity is found at the N-terminus or the C-terminus exists in one amino acid sequence, the region in which no identity is found cannot be aligned, and therefore, it is not used to calculate the percent identity.

(Method for Preparing Enzyme)

Hereinafter, a method for preparing oxidoreductase according to the present invention will be described.

(Construction of Expression Plasmid)

The plasmid for expressing oxidoreductase according to the present invention is obtained by a commonly used method. For example, DNA is extracted from a microorganism producing oxidoreductase according to the present invention to construct a DNA library. A DNA fragment encoding the oxidoreductase according to the present invention is identified and isolated from the constructed DNA library. The DNA fragment is amplified by a polymerase chain reaction (PCR) with complementary primers in which the isolated DNA fragment is used as a template to clone a gene encoding the oxidoreductase according to the present invention. The amplified DNA fragment is ligated into a vector to obtain a plasmid having the DNA fragment encoding the oxidoreductase according to the present invention.

Alternatively, the DNA fragment encoding the oxidoreductase according to the present invention is chemically synthesized, and the DNA fragment is ligated into the vector to obtain the plasmid having DNA encoding the oxidoreductase according to the present invention.

A strain such as *E. coli* is transformed with the obtained plasmid to obtain a strain such as the *E. coli* having the DNA encoding the oxidoreductase according to the present invention.

Further, for example, the strain such as yeast may be transformed with the obtained plasmid to obtain a strain such as yeast having the DNA encoding the oxidoreductase according to the present invention. As a transformation method to yeast, a known method, for example, a method using lithium acetate (Methods Mol. Cell. Biol., 5, 255-269 (1995)), an electroporation (J Microbiol Methods 55 (2003) 481-484), or the like, can be suitably used, but the present invention is not limited thereto, and transformation may be performed using various optional techniques including a spheroplast method, a glass bead method, and the like. Microorganisms classified as yeasts include, for example, yeasts belonging to the genus *Zygosaccharomyces*, the genus *Saccharomyces*, the genus *Pichia*, and the genus *Candida*. The plasmid having the DNA encoding the oxidoreductase of the present invention may include a marker gene to allow the selection of transformed cells. The marker gene includes, for example, genes which complement the auxotrophy of the host, such as URA3, TRP1. It is also desirable that the plasmid having the DNA encoding the oxidoreductase of the present invention contain a promoter or other control sequence (e.g., secretory signal sequence, enhancer sequence, terminator sequence or polyadenylation sequence, and the like) capable of expressing the oxidoreductase gene of the present invention in the host cell. Specific examples of the promoter include a GAL1 promoter, an ADH1 promoter, and the like.

Other examples of host cells include, for example, filamentous fungi such as the genus *Aspergillus* and the genus *Trichoderma*. A method for producing a transformant of a filamentous fungus is not particularly limited, and examples thereof include a method of inserting into a host filamentous fungus in an aspect in which the DNA encoding the oxidoreductase of the present invention is expressed according to a conventional method. Specifically, a transformant overexpressing the gene encoding the oxidoreductase is obtained by making a DNA construct in which the gene encoding the oxidoreductase is inserted between an expression-inducing promoter and a terminator, then transforming the host filamentous fungus with the DNA construct containing the gene encoding the oxidoreductase of the present invention. In this specification, the DNA fragment consisting of an expression-inducible promoter-a gene encoding the oxidoreductase-terminator and a recombinant vector containing the DNA fragment produced for transforming a host filamentous fungus are collectively referred to as a DNA construct.

The method of inserting the gene encoding the oxidoreductase into the host filamentous fungus in such a manner that the gene is expressed is not particularly limited, and for example, the method includes a method of inserting the gene directly into the chromosome of the host organism by using homologous recombination, or a method of introducing the gene into the host filamentous fungus by linking on a plasmid vector, and the like.

In a method using homologous recombination, the DNA construct can be ligated between sequences homologous to an upstream region and a downstream region of the recombination site on the chromosome and inserted into the genome of the host filamentous fungus. Transformants by self-cloning can be obtained by overexpressing within the host filamentous fungi under high expression promoter control of the host filamentous fungus itself. The high expression promoter is not particularly limited, and examples thereof include a promoter region of a TEF1 gene (tef1), which is a translational elongation factor, a promoter region of an α-amylase gene (amy), and an alkaline protease gene (alp) promoter region.

In a method utilizing the vector, the DNA construct can be incorporated into the plasmid vector used in the transformation of filamentous fungi by a conventional method, and the corresponding host filamentous fungus can be transformed by a conventional method.

Such a suitable vector-host system is not particularly limited as long as it is a system capable of producing the oxidoreductase of the present invention in a host filamentous fungus, and examples thereof include a system of pUC19 and filamentous fungi, a system of pSTA14 (Mol. Gen. Genet. 218, 99-104, 1989), and filamentous fungi.

The DNA construct is preferably introduced into the chromosomes of the host filamentous fungus and used, in other ways, but can also be used without introduction into the chromosomes by incorporating the DNA construct into autonomously replicated vector (Ozeki et al. Biosci. Biotechnol. Biochem. 59, 1133 (1995)).

The DNA construct may include a marker gene to allow the selection of transformed cells. The marker gene is not particularly limited, and examples of the marker gene include a gene which complement the auxotrophy of the host, such as pyrG, niaD, adeA; and a drug resistance gene against a drug, such as pyrithiamine, hygromycin B, or oligomycin. It is also preferred that the DNA construct contains a promoter, a terminator, or other control sequences (e.g., an enhancer, a polyadenylation sequence, and the like) which allow for overexpression of the gene encoding the oxidoreductase of the invention in the host cell. Promoters include, but are not limited to, an appropriate expression-inducing promoter and a constitutive promoter, such as a tef1 promoter, an alp-promoter, an amy-promoter, and the like. The terminator is also not particularly limited, and examples thereof include an alp terminator, an amy terminator, and a tef1 terminator.

In the DNA construct, the expression control sequence of the gene encoding the oxidoreductase of the present invention is not necessarily required when the DNA fragment including the gene encoding the oxidoreductase of the present invention, which will be inserted, includes a sequence having an expression control function. When transformation is performed by a co-transformation method, the DNA construct may not have a marker gene in some cases.

An embodiment of the DNA construct is a DNA construct in which, for example, a tef1 gene promoter, a gene encoding the oxidoreductase, an alp gene terminator, and a pyrG marker gene are ligated to an In-Fusion Cloning Site at a multicloning site of pUC19.

As a transformation method to a filamentous fungus, a method known to those skilled in the art can be appropriately selected, and for example, a protoplast PEG method using polyethylene glycol and calcium chloride after preparing a protoplast of a host filamentous fungus (see, for example, Mol. Gen. Genet. 218, 99-104, 1989, Japanese laid-open patent publication No. 2007-222055, and the like) can be used. As the medium for regenerating the transformed filamentous fungus, an appropriate medium is used according to the host filamentous fungus to be used and the transformation marker gene. For example, when *Aspergillus sojae* is used as the host filamentous fungus and a pyrG gene is used as the transformation marker gene, regeneration of the transformed filamentous fungus can be performed, for example, in a Czapek-Dox minimal medium (manufactured by Difco Laboratories) containing 0.5% agar and 1.2 M sorbitol.

(Recombinant Expression of Enzyme)

The strain such as *E. coli* having the DNA encoding the oxidoreductase of the present invention is cultured in a medium. When culturing a microbial host cell, it may be carried out by aeration-agitated deep culture, shaking culture, stationary culture, or the like, at a culture temperature of 10° C. to 42° C., preferably at a culture temperature of about 25° C., for several hours to several days, and more preferably at a culture temperature of about 25° C., for preferably 1 to 7 days. As the medium for culturing the microbial host cell, for example, a medium in which one or more kinds of inorganic salts such as sodium chloride, monopotassium phosphate, dipotassium phosphate, magnesium sulfate, magnesium chloride, ferric chloride, ferric sulfate, or manganese sulfate are added to one or more kinds of nitrogen sources such as yeast extract, tryptone, peptone, meat extract, corn steep liquor, or leaching solution of soybean or wheat bran, and if necessary, a saccharine material, vitamins, and the like are appropriately added is used. Bacterial cells are separated from the culture medium obtained by the culturing by centrifugation. The bacterial cells obtained by the separation are subjected to ultrasonic grinding, grinding, or the like, or to treatment with a lytic enzyme such as lysozyme or yatalase to obtain a suspension, and the suspension is centrifuged to obtain a crude enzyme solution from the obtained fraction.

(Purification of Enzyme)

The method for purifying an enzyme may be any method as long as it is capable of purifying an enzyme from a crude enzyme solution. For example, an enzyme can be purified from the crude enzyme solution by a commonly used method such as ion exchange chromatography, gel filtration chromatography, or the like.

(Enzyme Activity Measurement)

The method for measuring the activity of the enzyme may be any method as long as it directly or indirectly measures a product of a redox reaction catalyzed by the enzyme. For example, a reduced product is generated by catalyzing a redox reaction by the enzyme, and a current value generated by the reduced product passing electrons to an electrode is measured. Thus, it is possible to measure the enzyme activity. Suitably, the enzyme activity can be measured by reacting the reduced product by the redox reaction catalyzed by the enzyme with a reagent containing a light-absorbing substance reacting with the reduced product (hereinafter, a "light-absorbing reagent") and performing absorbance measurement.

(Quantification of EAP)

Oxidoreductase acting on EAP is allowed to act on a sample containing EAP. The concentration of EAP in the sample is not particularly limited but may be 0.1 µM to 1000 µM, for example. The duration of action may be, for example, 5 seconds to 120 minutes, preferably 0.5 to 60 minutes, more preferably 1 to 30 minutes, and even more preferably 1 to 10 minutes. The working temperature depends on the optimum temperature of the enzyme to be used, and is, for example, 20° C. to 45° C., and the temperature used for the ordinary enzyme reaction can be appropriately selected.

Suitable amounts of oxidoreductase acting on the EAP used in the present invention may be added, for example, such that the final concentration is 0.001 U/ml to 50 U/ml, preferably 0.01 U/ml to 10 U/ml. Generally, the lower the concentration of the substrate contained in the sample solution, the higher the final concentration of oxidoreductase to be added. The pH at the time of acting is preferably adjusted using a buffering agent so as to have a pH suitable for the reaction, considering an optimum pH of oxidoreductase, but is not limited thereto as long as it can act. Example is pH 3 to pH 11, preferably pH 5 to pH 9. Examples of the buffering agent which can be used include N-[tris (hydroxymethyl) methyl] glycine, phosphate, acetate, carbonate, tris (hydroxymethyl)-aminomethane, borate, citrate, dimethyl glutamate, tricine, HEPES, MES, Bis-Tris, ADA, PIPES, ACES, MOPSO, BES, MOPS, TES, DIPSO, TAPSO, POPSO, HEPPSO, EPPS, Tricine, Bicine, TAPS, phthalic acid, tartaric acid, and the like.

The present invention provides a method of measuring EAP by reducing a mediator by oxidoreductase acting on EAP, and reacting the reduced mediator with a reagent which undergoes coloring or fading. Examples of the colorimetric substrate used in the present invention include tetrazolium compounds (Tetrazolium blue, Nitro-tetrazolium blue, Water soluble tetrazolium (WST)-1, WST-3, WST-4, WST-5, WST-8, WST-9) and the like in addition to DCIP (2, 6-Dichlorophenolindophenol).

A sample used in the EAP measurement method of the present invention may be a sample derived from any biological sample, such as, blood, plasma, or the like, which may include EAP. The sample may be processed, as appropriate. For example, it may be concentrated by a centrifugal concentrator.

(Composition Containing Oxidoreductase and Kit for Quantification of Ethanolamine Phosphate)

The quantification method of EAP utilizing the oxidoreductase according to the present invention may be carried out by providing a composition containing oxidoreductase and a product reaction reagent or may be carried out by combining oxidoreductase and a commercially available product reaction reagent. For example, the quantification method may be provided as a composition for quantification of ethanolamine phosphate containing oxidoreductase, and as a composition for the quantification of ethanolamine phosphate further including a mediator which is reduced by adding the oxidoreductase, and a reagent which reacts with the reduced mediator. Also, the quantification method may be provided as a kit for quantification of ethanolamine phosphate including oxidoreductase, a mediator which is reduced by adding the oxidoreductase, and a reagent which reacts with the reduced mediator.

The mediator (also referred to as an artificial electron mediator, an artificial electron acceptor or an electron mediator) used in the measurement method or the kit for quantitation of the present invention is not particularly limited as long as it can receive electrons from oxidoreductase. Examples of the mediators include quinones, phenazines, viologens, cytochromes, phenoxazines, phenothiazines, ferricyanides e.g., potassium ferricyanide, ferredoxins, ferrocene, osmium complexes and derivatives thereof, and the phenazine compounds include, but are not limited to, 5-Methylphenazinium methosulfate (PMS) and methoxy PMS.

(Sensor Chip and Electrode)

Figure 8A:
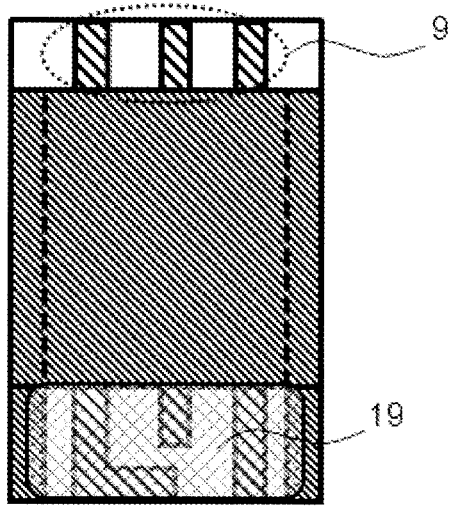
FIG. 8A is a schematic diagram of a sensor chip 10 according to an embodiment of the present invention.
Figure 8B:
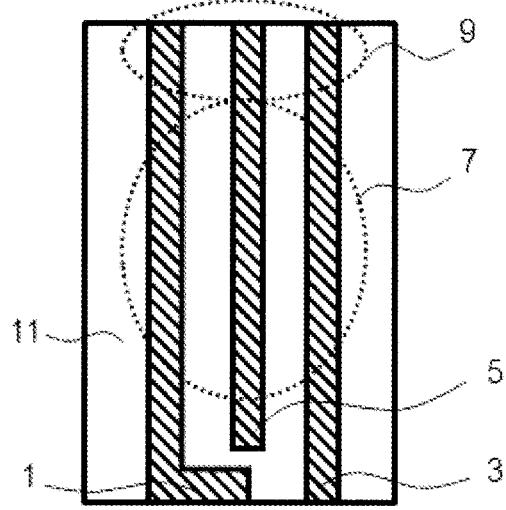
FIG. 8B is a schematic diagram showing a member constituting the sensor chip 10.
Figure 8C:
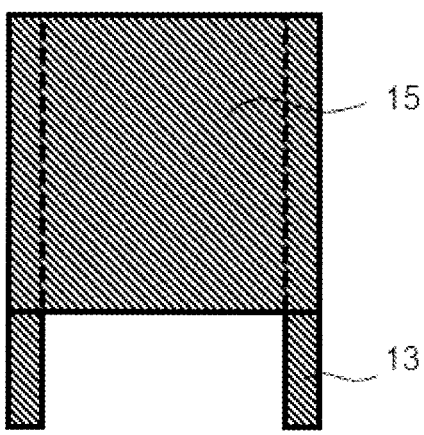
FIG. 8C is a schematic diagram showing a member constituting the sensor chip 10.
Figure 8D:
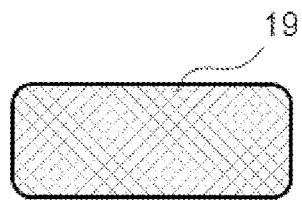
FIG. 8D is a schematic diagram showing a member constituting the sensor chip 10.

FIG. 8A is a schematic diagram of a sensor chip 10 according to an embodiment of the present invention, and FIGS. 8B to 8D are schematic diagrams showing a member constituting the sensor chip 10. The sensor chip 10 includes two or more electrodes arranged on a substrate I 11. The substrate 11 is made of an insulating material. In FIGS. 8A and 8B, as an example, a working electrode 1, a counter electrode 3, and a reference electrode 5 are arranged on the substrate 11. Each electrode is electrically connected to a wiring unit 7, and the wiring unit 7 is electrically connected to a terminal 9 located on the opposite side of each electrode. The working electrode 1, the counter electrode 3, and the reference electrode 5 are arranged apart from each other. The working electrode 1, the counter electrode 3, and the reference electrode 5 are preferably formed integrally with the wiring unit 7 and the terminal 9. Further, the counter electrode 3 and the reference electrode 5 may be integral.

As shown in FIGS. 8A and 8C, a spacer 13 is arranged on an end of the substrate 11 which is parallel to the wiring unit 7, and a cover 15 which covers the working electrode 1, the counter electrode 3, the reference electrode 5, and the spacer 13 is arranged. The spacer 13 and the cover 15 are made of an insulating material. The spacer 13 preferably has a thickness substantially equal to that of the working electrode 1, the counter electrode 3, and the reference electrode 5, and is in close contact with the working electrode 1, the counter electrode 3, and the reference electrode 5. The spacer 13 and the cover 15 may be integrally formed. The cover 15 is a protective layer which prevents the wiring unit 7 from being deteriorated by being exposed to the outside air and short-circuiting due to the penetration of the measurement sample.

In an embodiment, the oxidoreductase of the present invention may be applied, adsorbed, or immobilized on the electrode. Preferably, the oxidoreductase of the present invention is applied, adsorbed, or immobilized on the working electrode. In another embodiment, the mediator together with oxidoreductase may also be applied, adsorbed, or immobilized on the electrode. Oxidoreductase, or oxidoreductase and the mediator may be included in a reaction layer 19 arranged on the working electrode 1, the counter electrode 3, and the reference electrode 5. As the electrode, a carbon electrode, a metal electrode such as platinum, gold, silver, nickel, or palladium can be used. In the case of carbon electrodes, examples of the material include pyrolytic graphite carbon (PG), glassy carbon (GC), carbon paste and plastic foamed carbon (PFC). A measurement system may be a two-electrode system or a three-electrode system, for example, enzymes may be immobilized on the working electrode. Examples of the reference electrode include a standard hydrogen electrode, a reversible hydrogen electrode, a silver-silver chloride electrode (Ag/AgCl), a palladium-hydrogen electrode, and a saturated calomel electrode, and the Ag/AgCl is preferably used from the viewpoint of stability and reproducibility.

The enzymes can be immobilized on the electrode by crosslinking, coating with a dialysis membrane, encapsulation in a polymer matrix, use of a photocrosslinkable polymer, use of a conductive polymer, use of an oxidation/reduction polymer, and the like. The enzymes may also be immobilized in a polymer or adsorbed onto the electrode together with a mediator, or these techniques may be combined.

The mediator (also referred to as an artificial electron mediator, an artificial electron acceptor or an electron mediator) used in the composition, kit, electrode, or sensor chip of the present invention is not particularly limited as long as it can receive electrons from oxidoreductase. Examples of the mediators include quinones, phenazines, viologens, cytochromes, phenoxazines, phenothiazines, ferricyanides, e.g., potassium ferricyanide, ferredoxins, ferrocene, osmium complexes and derivatives thereof, and the like, and examples of the phenazine compounds include, but are not limited to, PMS and methoxy PMS.

The oxidoreductase of the present invention can be applied to various electrochemical measurement methods by using a potentiostat, a galvanostat, or the like. The electrochemical measurement includes various techniques such as amperometry, potentiometry, and coulometry. For example, by using an amperometry method, the concentration of EAP in a sample can be calculated by measuring a current value generated by applying +600 mV to +1000 mV (vs. Ag/AgCl) by a hydrogen peroxide electrode to hydrogen peroxide produced when oxidoreductase reacts with EAP. For example, a calibration curve can be generated by measuring current values for known concentrations of EAP (0, 50, 100, 150, 200 μM) and plotting against concentrations of EAP. The concentration of EAP can be obtained from the calibration curve by measuring the current value of the unknown EAP. As the hydrogen peroxide electrode, for example, a carbon electrode or a platinum electrode can be used. The amount of hydrogen peroxide can be quantified by measuring the reduction current value generated by applying −400 mV to +100 mV (vs. Ag/AgCl) using an electrode immobilized with a reductase such as peroxidase or catalase, instead of the hydrogen peroxide electrode, and the value of EAP can also be measured.

By, for example, an amperometry method, the concentration of EAP in the sample can be calculated by mixing a mediator in a reaction solution, transferring electrons generated when oxidoreductase reacts with EAP to an oxidized mediator, generating a reduced mediator, and measuring a current value generated by applying −1000 mV to +500 mV (vs. Ag/AgCl). As the counter electrode, a carbon electrode or a platinum electrode is preferred. For example, a calibration curve can be generated by measuring current values for known concentrations of EAP (0, 50, 100, 150, 200 μM) and plotting against the concentrations of EAP. The concentration of EAP can be obtained from the calibration curve by measuring the current value of the unknown EAP.

In addition, printed electrodes (sensor chips) can be used to reduce the amount of solution required for measurement. In this case, the electrodes are preferably formed on a substrate composed of an insulating substrate. Specifically, the electrodes are preferably formed on the substrate by photolithography or printing techniques such as screen printing, gravure printing, and flexographic printing. Further, examples of the material of the insulating substrate include silicon, glass, ceramic, polyvinyl chloride, polyethylene, polypropylene, and polyester, but those having strong resistance to various solvents and chemicals are more preferably used.

[EAP Measurement Sensor]

Figure 9A:
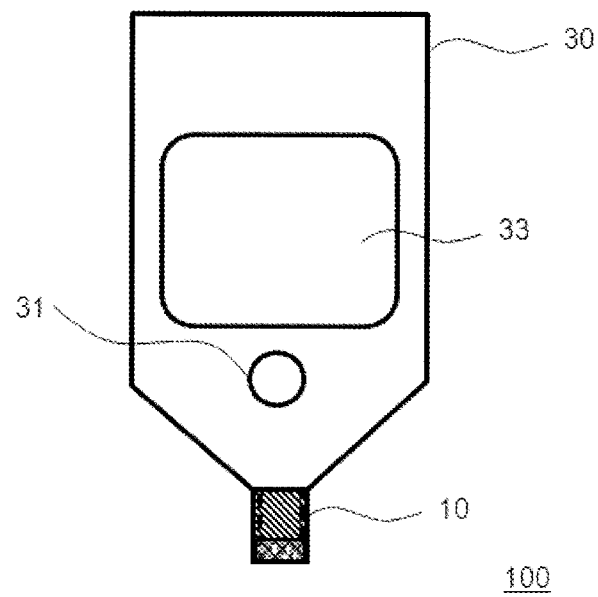
FIG. 9A is a schematic diagram of a sensor 100 according to an embodiment of the present invention.

In an embodiment, an EAP measurement sensor using the oxidoreductase of the present invention is provided. FIG. 9A is a schematic diagram of a sensor 100 according to an embodiment of the present invention. The sensor is an EAP measurement device using the oxidoreductase of the present invention and includes the sensor chip containing the oxidoreductase, and a measurement unit. A measurement unit 30 may include, for example, a switch 31 serving as an input unit and a display 33 serving as a display unit. The switch 31 may be used, for example, to control ON/OFF of a power supply of the measurement unit 30, or to control the initiation or interruption of the EAP measurement by the sensor 100. The display 33 may display a measured value of EAP, for example, and may include a touch panel as the input unit for controlling the measurement unit 30.

Figure 9B:
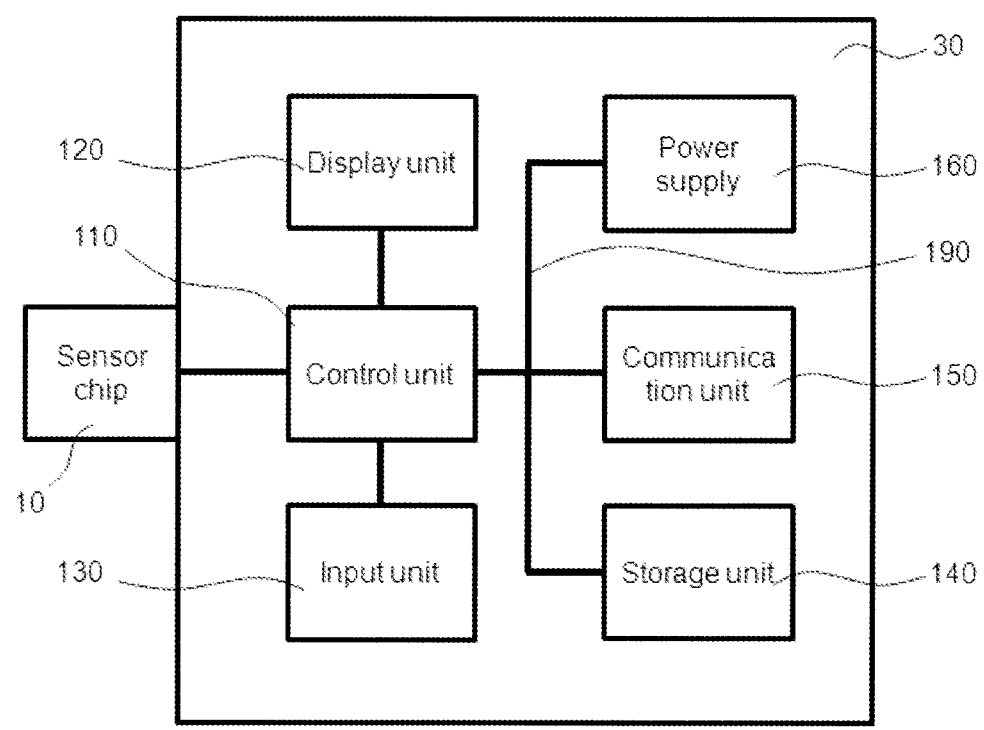
FIG. 9B is a block diagram of the sensor 100 according to an embodiment of the present invention.

FIG. 9B is a block diagram of the sensor 100 according to an embodiment of the present invention. The sensor 100 may include, for example, a control unit 110, a display unit 120, an input unit 130, a storage unit 140, a communication unit 150, and a power supply 160 in the measurement unit 30, which may be electrically connected to each other by a wiring 190. Further, a terminal of the sensor chip 10 to be described later and a terminal of the measurement unit 30 are electrically connected, and the current generated at the sensor chip 10 is detected by the control unit 110. The control unit 110 is a control device which controls the sensor 100 and is composed of, for example, a known central processing unit (CPU) and an operation program which controls the sensor 100. The control unit 110 may include a central processing unit (CPU) and an operating system (OS) and may include application programs or modules for performing EAP measurements.

The display unit 120 may include, for example, the known display 33, and may display the measured value of EAP, states of the measurement unit 30, and requests for operations to a measurer. An input unit 130 is an input device for the measurer to operate the sensor 100, and may be, for example, a touch panel arranged on the switch 31 or the display 33. A plurality of switches 31 may be arranged in the measurement unit 30.

The storage unit 140 consists of a main storage device (memory) and an auxiliary storage device (hard disk) may be arranged externally. The main storage device (memory) may be composed with a read-only memory (ROM) and/or random access memory (RAM). The operation program, operating system, application program, or module is stored in the storage unit 140 and executed by the central processing unit to configure the control unit 110. The measured values and the current values can be stored in the storage unit 140.

The communication unit 150 is a known communication device which connects the sensor 100 or the measurement unit 30 to external devices (such as computers, printers, or networks). The communication unit 150 and the external devices are connected by wired or wireless communication. The power supply 160 is also a known power supply device which supplies power to the sensor 100 or the measurement unit 30.

As described above, the quantification method of EAP according to the present invention, oxidoreductase for quantitation, the composition for quantification, and the kit for quantification can provide a novel quantification method for quantifying the concentration of EAP, which is a biomarker of depression, a novel enzyme for quantification, a novel composition for quantification, a novel kit for quantification and a novel sensor for quantification, by containing the oxidoreductase.

(Quantitation Method of EAP Using Oxidase Activity)

The oxidase used in the present invention is an oxidizing enzyme which acts on EAP as a substrate. It is considered that EAP oxidase can be most suitably used as the oxidase used in the present invention. However, by the time of filing the present application, the EAP oxidase has not been identified. Substrates with CH—NH$_2$ or CH—NH bonds exist as substrates structurally similar to EAP, and amine oxidase exists as the enzyme to the substrate.

More specifically, examples of the substrates structurally similar to EAP include phenylethylamine, ethanolamine, tyramine, benzylamine, histamine, serotonin, spermine, spermidine, β-alanine, γ-aminobutyric acid (GABA), taurine, cadaverine, agmatine, and the like, and examples of the oxidizing enzyme to the substrate include phenylethylamine oxidase (PEAOX), ethanolamine oxidase, tyramine oxidase, benzylamine oxidase, histamine oxidase, serotonin oxidase, spermine oxidase, spermidine oxidase, β-alanine oxidase, γ-aminobutyric (GABA) oxidase, taurine oxidase, cadaverine oxidase, agmatine oxidase, and the like.

As the reaction condition of the oxidase used in the present invention, any condition may be used as long as it is a condition for acting on EAP and efficiently catalyzing an oxidation reaction. An enzyme generally has an optimum temperature and optimum pH which show the highest activity. Therefore, the reaction conditions are preferably near the optimum temperature and the optimum pH. For example, the reaction conditions of PEAOX can be suitably used at a temperature of 37° C. and pH8.5, which will be described later, but is not limited thereto.

As a reaction process of the oxidase used in the present invention, various chemicals may be participated when the oxidase of the present invention acts on EAP. For example, when the oxidase of the present invention acts on EAP, oxygen may participate as an electron acceptor for the redox reaction.

The oxidase of the present invention may be an oxidase produced by a naturally occurring microorganism or oxidase produced by a transformed microorganism. From the viewpoint of efficient mass expression of the enzyme, the enzyme can be efficiently expressed in large quantities by using the transformed microorganism.

For example, the oxidase of the present invention may be oxidase (AgPEAOX) produced by *Arthrobacter globiformis* or oxidase produced by *E. coli* transformed with a plasmid containing a PEAOX gene derived from *Arthrobacter globiformis*, but by using the *E. coli* transformed with the plasmid containing the PEAOX gene derived from *Arthrobacter globiformis*, oxidase can be efficiently expressed in large quantities.

For example, the oxidase of the present invention may be LcAOX produced by *Lichtheimia corymbifera* or amine oxidase produced by *E. coli* transformed with a plasmid containing the LcAOX gene having the base sequence of SEQ ID NO: 16 derived from *Lichtheimia corymbifera*, but by using the *E. coli* transformed with the plasmid containing the LcAOX gene derived from *Lichtheimia corymbifera*, oxidase can be efficiently expressed in large quantities.

Further, for example, the oxidase of the present invention may be LrHP produced by *Lichtheimia ramosa* or hypothetical protein produced by *E. coli* transformed with a plasmid containing the LrHP gene having the base sequence of SEQ ID NO: 21 derived from *Lichtheimia ramosa*, but by using the *E. coli* transformed with the plasmid containing the LrHP gene derived from *Lichtheimia ramosa*, oxidase can be efficiently expressed in large quantities.

For example, the oxidase of the present invention may be SrAOX3925 produced by *Syncephalastrum racemosum* or amine oxidase produced by *E. coli* transformed with a plasmid containing the SrAOX3925 gene having the base sequence of SEQ ID NO: 26 derived from *Syncephalastrum racemosum*, but by using the *E. coli* transformed with the plasmid containing the SrAOX3925 gene derived from *Syncephalastrum racemosum*, oxidase can be efficiently expressed in large quantities.

For example, the oxidase of the present invention may be SrAOX3926 produced by *Syncephalastrum racemosum* or amine oxidase produced by *E. coli* transformed with a plasmid containing the SrAOX3926 gene having the base sequence of SEQ ID NO: 31 derived from *Syncephalastrum racemosum*, but by using the *E. coli* transformed with the plasmid containing the SrAOX3926 gene derived from *Syncephalastrum racemosum*, oxidase can be efficiently expressed in large quantities.

For example, the oxidase of the present invention may be SrEAOX produced by *Syncephalastrum racemosum* or an ethanolamine oxidase produced by *E. coli* transformed with a plasmid containing the SrEAOX gene having the base sequence of SEQ ID NO: 36 derived from *Syncephalastrum racemosum*, but by using the *E. coli* transformed with the plasmid containing the SrEAOX gene derived from *Syncephalastrum racemosum*, oxidase can be efficiently expressed in large quantities.

In an embodiment, examples of the oxidase of the present invention include oxidase which has high sequence identity (e.g., 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, and 99% or more) relative to the amino acid sequence (SEQ ID NO: 9) of PEAOX produced by *Arthrobacter globiformis*, and oxidase having an amino acid sequence in which 1 or more amino acids are altered or varied, deleted, substituted, added and/or inserted in the amino acid sequence of SEQ ID NO: 9.

In an embodiment, examples of the oxidase of the present invention include oxidase which has high sequence identity (e.g., 70% or more, 72% or more, 73% or more, 74% or more, 75% or more, 76% or more, 77% or more, 78% or more, 79% or 80% or more, more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, e.g., 99% or more) relative to the amino acid sequence of LcAOX (SEQ ID NO: 15) produced by *Lichtheimia corymbifera*, and oxidase having an amino acid sequence in which 1 or more amino acids are altered or varied, deleted, substituted, added and/or inserted in the amino acid sequence of SEQ ID NO: 15.

In an embodiment, examples of the oxidase of the present invention include oxidase which has high sequence identity (e.g., 70% or more, 72% or more, 73% or more, 74% or more, 75% or more, 76% or more, 77% or more, 78% or more, 79% or 80% or more, more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, e.g., 99% or more) to the amino acid sequence (SEQ ID NO: 20) of LrHP produced by *Lichtheimia ramosa*, and oxidase having an amino acid sequence in which 1 or more amino acids are altered or varied, deleted, substituted, added and/or inserted in the amino acid sequence of SEQ ID NO: 20.

In an embodiment, examples of the oxidase of the present invention include oxidase which has high sequence identity (e.g., 70% or more, 72% or more, 73% or more, 74% or more, 75% or more, 76% or more, 77% or more, 78% or more, 79% or 80% or more, more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, e.g., 99% or more) to the amino acid sequence (SEQ ID NO: 25) of SrAOX3925 produced by *Syncephalastrum racemosum*, and oxidase having an amino acid sequence in which 1 or more amino acids are altered or varied, deleted, substituted, added and/or inserted in the amino acid sequence of SEQ ID NO: 25.

In an embodiment, examples of the oxidase of the present invention include oxidase which has high sequence identity (e.g., 70% or more, 72% or more, 73% or more, 74% or more, 75% or more, 76% or more, 77% or more, 78% or more, 79% or 80% or more, more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, e.g., 99% or more) to the amino acid sequence (SEQ ID NO: 30) of SrAOX3926 produced by *Syncephalastrum racemosum*, and oxidase having an amino acid sequence in which 1 or more amino acids are altered or varied, deleted, substituted, added and/or inserted in the amino acid sequence of SEQ ID NO: 30.

In an embodiment, examples of the oxidase of the present invention include oxidase which has high sequence identity (e.g., 70% or more, 72% or more, 73% or more, 74% or more, 75% or more, 76% or more, 77% or more, 78% or more, 79% or 80% or more, more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, e.g., 99% or more) to the amino acid sequence (SEQ ID NO: 35) of SrEAOX produced by *Syncephalastrum racemosum*, and oxidase having an amino acid sequence in which 1 or more amino acids are altered or varied, deleted, substituted, added and/or inserted in the amino acid sequence of SEQ ID NO: 35.

Since the amino acid sequence identity of these oxidases is calculated by the same method as the amino acid sequence identity of oxidoreductase, detailed description thereof will be omitted.

(Methods for Preparing Enzyme)

Hereinafter, a method for preparing oxidase according to the present invention will be described.

(Construction of Expression Plasmid)

A plasmid for expressing oxidase according to the present invention is obtained by a commonly used method. For example, DNA is extracted from a microorganism producing oxidase according to the present invention to create a DNA library. From the created DNA library, a DNA fragment encoding the oxidase according to the present invention is identified and isolated. The DNA fragment is amplified by a polymerase chain reaction (PCR) with complementary primers in which the isolated DNA fragment is used as a template to clone a gene encoding the oxidoreductase according to the present invention. The amplified DNA fragment is ligated into a vector to obtain a plasmid having the DNA fragment encoding the oxidase according to the invention.

Alternatively, the DNA fragment encoding the oxidase according to the present invention is chemically synthesized, and the DNA fragment is ligated to the vector to obtain a plasmid having the DNA fragment encoding the oxidase according to the present invention.

A strain such as *E. coli* is transformed with the obtained plasmid to obtain a strain such the *E. coli* having the DNA encoding the oxidase according to the present invention.

As a host cell utilized for the expression of the oxidase according to the present invention, yeast or a filamentous fungus may be used. The method may be the same as that for the expression of the oxidoreductase described above, and a detailed description thereof will be omitted.

The oxidase according to the present invention may have an amino acid substitution which enhances the reactivity to EAP. For example, it may have an amino acid substitution at a position corresponding to phenylalanine at position 105 and/or a position corresponding to leucine at position 358 of PEAOX derived from *Arthrobacter globiformis* having an amino acid sequence of SEQ ID NO: 9.

(Recombinant Expression and Purification of Enzymes)

The expression and purification of the oxidase may be performed by the same method as in the expression and purification of the oxidoreductase described above, and a detailed description thereof will be omitted.

(Enzyme Activity Measurement)

The method for measuring the activity of an enzyme may be any method as long as it directly or indirectly measures a product by a reaction catalyzed by an enzyme. For example, if a product by the reaction catalyzed by the enzyme and a reagent reacting with the product (hereinafter, a "product reaction reagent") are reacted and a light-absorbing substance generated by the reaction is measured, the enzyme activity can be measured by performing absorbance measurement.

(Quantification of EAP)

The oxidase acting on EAP is allowed to act on a sample containing EAP. A concentration of EAP in the sample is not particularly limited, but may be, for example, 0.1 µM to 1000 µM. Duration of action may be, for example, 5 seconds to 120 minutes, preferably 0.5 minutes to 60 minutes, more preferably 1 minute to 30 minutes, and even more preferably 1 minute to 10 minutes. A working temperature depends on the optimum temperature of the enzyme to be used, and is, for example, 20° C. to 45° C., and the temperature used for the ordinary enzyme reaction can be appropriately selected.

Suitable amounts of oxidase acting on the EAP used herein may be added, for example, such that the final concentration is 0.001 U/ml to 50 U/ml, preferably 0.01 U/ml to 10 U/ml. Generally, the lower the concentration of substrate contained in the sample solution, the higher the final concentration of oxidase to be added. pH at the time of acting is preferably adjusted using a buffering agent so as to have an optimum pH of the oxidase and to have a pH suitable for the reaction but is not limited thereto as long as it can act. The example is pH 3 to pH 11, preferably pH 5 to pH 9. The buffering agents which can be used are similar to those for quantifying EAP by oxidoreductase.

The present invention provides a method for measuring EAP by measuring a product or consumption by the action of oxidase acting on EAP but hydrogen peroxide is exemplified as a product which is easy to measure as a preferable measurement target. The hydrogen peroxide produced by the action of the oxidase may be detected by a chromogenic substrate, and the examples of a chromogenic substrate used in the present invention include, for example, ADOS (N-ethyl-N-(2-hydroxy-3-sulfopropyl)-m-anisidine), ALOS (N-ethyl-N-(2-hydroxy-3-sulfopropyl)aniline), TOOS (N-ethyl-N-(2-hydroxy-3-sulfopropyl)-m-toluidine sodium), DA-67 (10-(carboxymethylaminocarbonyl)-3,7-bis(dimethylamino)-phenothiazine), DA-64 (N-(carboxymethylaminocarbonyl)-4'-4'-bis(dimethylamino)-diphenylamine), and the like in addition to 4-aminoantipyrine. ADOS, ALOS, TOOS develop color when condensed with 4-aminoantipyrine. DA-64, DA-67 do not require 4-aminoantipyrine and develop color when formulated alone. In both cases, the chromogenic reaction is catalyzed by peroxidase. Further, examples of the consumption to be measured include dissolved oxygen, and the amount of dissolved oxygen in the reaction solution can be measured using a dissolved oxygen meter or the like. For example, the degree of color development (absorbance change amount) of the above measurement reagent is measured by a spectrophotometer or a biochemical automatic analyzer or the like, and the EAP contained in the sample can be measured as compared with the absorbance of the standard sample.

The sample used in the EAP measurement method of the present invention may be a sample derived from any biological sample, such as, blood, plasma, or the like, which may include EAP. The sample may be processed, as appropriate. For example, it may be concentrated by a centrifugal concentrator.

(Composition Containing Oxidase and Kit for Quantification of Ethanolamine Phosphate)

The method for a quantification of EAP using the oxidase according to the present invention may be carried out by providing a composition containing oxidase and a product reaction reagent or may be carried out by combining oxidase and a commercially available product reaction reagent. For example, it may be provided as a composition for the quantification of ethanolamine phosphate containing oxidase or a composition for the quantification of ethanolamine phosphate further comprising a reagent which reacts with the hydrogen peroxide produced by adding oxidase. Further, it may be provided as a kit for the quantification of ethanolamine phosphate containing the oxidase and a reagent which reacts with hydrogen peroxide produced by adding oxidase.

(Sensor Chip and Electrode)

In an embodiment, the oxidase of the present invention may be applied, adsorbed, or immobilized on an electrode. Preferably, the oxidase of the present invention is applied, adsorbed, or immobilized on a working electrode. Since the configuration of the electrode can be applied with the same configuration as that of the configuration described for the electrode using oxidoreductase, a detailed description thereof will be omitted. In addition, the oxidase can be immobilized to the electrode by crosslinking, coating with a dialysis membrane, encapsulation in a polymer matrix, use of a photocrosslinkable polymer, use of a conductive polymer, use of an oxidation/reduction polymer, and the like.

The oxidase of the present invention can be applied to various electrochemical measurement methods by using a potentiostat, a galvanostat, or the like. The electrochemical measurement includes various techniques such as amperometry, potentiometry, and coulometry. For example, by the amperometry method, the concentration of EAP in the sample can be calculated by measuring the current value generated by applying +600 mV to +1000 mV (vs. Ag/AgCl) by the hydrogen peroxide electrode to the hydrogen peroxide produced when oxidase reacts with EAP. For example, a calibration curve can be generated by measuring current values for known concentrations of EAP (0, 50, 100, 150, 200 µM) and plotting against the concentrations of EAP. The concentration of EAP can be obtained from the calibration curve by measuring the current value of the unknown EAP. As the hydrogen peroxide electrode, for example, a carbon electrode or a platinum electrode can be used. In addition, The amount of hydrogen peroxide can be quantified by measuring the reduction current value generated by applying −400 mV to +100 mV (vs. Ag/AgCl) using an electrode immobilized with a reductase such as peroxidase or catalase, instead of the hydrogen peroxide electrode, and the value of EAP can also be measured.

Further, the printed electrodes (sensor chips) can be used to reduce the amount of solution required for measurement. The electrodes are then preferably formed on the substrate made of the insulating substrate. The configuration of the sensor chip using oxidase may be the same as the configuration of the sensor chip using oxidoreductase, and a detailed description thereof will be omitted.

[EAP Measurement Sensor]

In an embodiment, an EAP measurement sensor using the oxidase of the present invention is provided. The sensor is an EAP measurement device using the oxidase of the present invention and includes a sensor chip containing the oxidase and a measurement unit. The configuration of the EAP measurement sensor using the oxidase may be the same as the configuration of the EAP measurement sensor using oxidoreductase, and a detailed description thereof is omitted.

As described above, the method for the quantification of EAP, the oxidase for quantification, the composition for quantification, and the kit for quantitation according to the present invention can provide a novel quantification method for quantifying the concentration of EAP, which is a biomarker of depression, a novel enzyme for quantification, a novel composition for quantification, a novel kit for quantification and a novel sensor for quantification by containing the oxidase.

EXAMPLE

By showing specific examples and test results of the quantification method, oxidoreductase for quantification, the composition for quantification, and the kit for quantification according to the present invention described above, a detailed description will be given.

(Preparation of Recombinant Plasmid peT22b(+)-LaTDH DNA)

An LaTDH gene having the base sequence of SEQ ID NO: 2, which contain the restriction sites NdeI and BamHI at both ends, and a SmTDH gene having the base sequence of SEQ ID NO: 4 were synthesized entirely, and first, the LaTDH gene was inserted between the restriction sites NdeI and BamHI of peT22b(+), and this was used to transform *E. coli* JM109.

An *E. coli* strain JM109 (peT22b(+)-LaTDH) with the recombinant plasmid was inoculated into 2.5 ml of LB-amp medium [1% (W/V) bactotryptone, 0.5% (W/V) yeast extract, 0.5% (W/V) NaCl, 50 μg/ml Ampicillin], and cultured by shaking at 37° C. for 20 hours to obtain cultures.

The culture was centrifuged at 7,000 rpm for 5 minutes to collect the bacterium and obtain bacterial cells. Then, the recombinant plasmid peT22b(+)-LaTDH was extracted from this bacterial cell and purified using QIAGEN (registered trademark) tip-100 (manufactured by QIAGEN K.K.) to obtain 2.5 pg of DNA of the recombinant plasmid peT22b(+)-LaTDH.

(Preparation of Recombinant Plasmid peT22b(+)-LaTDH-SmTDH DNA)

Using the SmTDH gene having the base sequence of SEQ ID NO: 4 as a template, a synthetic oligonucleotide of SEQ ID NOs: 5 and 6, PrimeSTAR (registered trademark) Max DNA Polymerase (manufactured by Takara Bio Inc.), were used, and a PCR reaction was carried out under the following conditions. In other words, 25 μl of PrimeSTAR Max Premix (2×), 100 pg of the template SmTDH gene, and 15 pmol of the above synthetic oligonucleotides were added, respectively, and the total amount was set to 50 μl by sterile water. The prepared reaction solution was incubated using a thermal cycler (manufactured by Eppendorf) for 2 minutes at 98° C. and followed by 30 cycles of "98° C., 10 seconds"-"55° C., 5 seconds"-"72° C., 35 seconds". In the same manner, using the obtained recombinant plasmid peT22b (+)-LaTDH as a template, a synthetic oligonucleotide of SEQ ID NOs: 7 and 8 was used, and a PCR reaction was performed. The reaction solution was electrophoresed on 1.0% agarose gel, and the amplified desired DNA was sliced and purified.

Next, using an In-Fusion (registered trademark) HD Cloning Kit (manufactured by Clontech Laboratories, Inc.), the resulting DNA fragments were ligated, and a co-expression vector in which the SmTDH gene was inserted into a 3' end side of LaTDH in peT22b(+)-LaTDH was constructed.

*E. coli* JM109 was transformed in the same manner as described above to obtain 2.5 pg of DNA of a recombinant plasmid peT22b(+)-LaTDH-SmTDH.

(Manufacturing of LaTDH, SmTDH)

An *E. coli* strain BL21(DE3) was transformed with the recombinant plasmid obtained by the above procedure. Each *E. coli* strain BL21(DE3) was cultured in 2.5 ml ZYP-5052 medium (0.5% glycerol, 0.05% glucose, 0.2% lactose, 50 mM $(NH_4)_2SO_4$, 50 mM $KH_2PO_4$, 50 mM $Na_2HPO_4$, 1 mM $MgSO_4$)) at 25° C. for 27 hours.

Thereafter, each bacterial cell was washed with 0.05 M CHES-NaOH acid buffer solution of pH 8.5, ultrasonically pulverized, and centrifuged at 15,000 rpm for 10 minutes, and a crude enzyme solution containing LaTDH having an amino acid sequence of SEQ ID NO: 1 and a crude enzyme solution containing LaTDH and SmTDH having an amino acid sequence of SEQ ID NO: 3 were prepared in the amount of 1.5 ml, respectively.

Similarly, the *E. coli* strain BL21(DE3) transformed only with peT22b(+) vector was also cultured and subjected to ultrasonic pulverization to prepare 1.5 ml of crude enzyme solution.

(Evaluation of Substrate Specificity of Each Crude Enzyme Solution)

An activity measurement using 2, 6-Dichlorophenolindophenol (DCIP) was performed in a 96-well plate. As shown in Table 1, 5 μl of the crude enzyme solution was mixed with 145 μl of a reagent consisting of potassium phosphate buffer solution pH 8.0, 5-Methylphenazinium methosulfate (PMS, manufactured by Fujifilm Wako Pure Chemical Corporation), 2, 6-Dichlorophenolindophenol (DCIP, manufactured by Sigma-Aldrich) and a substrate, and the loss of blue color (change in color) derived from DCIP caused by dehydrogenase activity was observed. As the substrate, taurine (manufactured by Fujifilm Wako Pure Chemical Corporation), ethanolamine phosphate (EAP, manufactured by Fujifilm Wako Pure Chemical Corporation), ethanolamine (manufactured by Tokyo Chemical Industry, Co., Ltd.), and benzylamine (manufactured by Tokyo Chemical Industry Co., Ltd.) were used.

TABLE 1

| Compound | Concentration |
| --- | --- |
| Potassium phosphate buffer pH 8.0 | 100 mM |
| PMS | 0.50 mM |
| DCIP | 0.09 mM |
| Substrate | 5 mM |

(LaTDH Activity Measurement) Among the compounds of Table 1, by mixing the regent in which the buffer solution is changed from potassium phosphate buffer pH 8.0 to CHES-NaOH acid buffer solution pH 8.5 and EAP is used as the substrate, which is adjusted to the concentration of 5 mM, 10 mM, 30 mM, 100 mM of EAP, with the crude enzyme solution of LaTDH-SmTDH or LaTDH, and by measuring the amount of change in absorbance at 600 nm, the enzyme activity of LaTDH-SmTDH or LaTDH was calculated.

The amount of change in absorbance was determined by incubating 1400 µl of the reagent containing CHES-NaOH acid buffer solution, DCIP, and EAP for 5 minutes at 30° C., then adding 50 µl of PMS and 50 µl of the crude enzyme solution and measuring the amount of change at $A_{600}$ ($\Delta A_s$) per 1 minute at 30° C. using a spectrophotometer (U-3900, manufactured by Hitachi High-Tech Science Corporation).

Next, 50 µl of M CHES-NaOH acid buffer solution instead of the substrate solution was added and mixed, and the amount of change at $A_{600}$ ($\Delta A_0$) per 1 minute at 30° C. was measured.

Dehydrogenase activity was calculated based on the following formula:

$$\text{Dehydrogenase activity (U/ml)} = (\Delta A_S - \Delta A_0) \times 1.5 \times df/\\(21.4 \times 0.05) = 1.4 \times (\Delta A_S - \Delta A_0) \times df$$

21.4: Millimolar extinction coefficient ($mM^{-1}cm^{-1}$) of DCIP dye for 600 nm-wavelength light df: Dilution rate of enzyme solution (Test Results: Evaluation of Substrate Specificity of Each Crude Enzyme Solution)

By observing the degree of loss of blue color derived from DCIP, a result that both the crude enzyme solution co-expressing LaTDH-SmTDH and the crude enzyme solution expressing LaTDH reacted most to taurine and also reacted to ethanolamine phosphate was obtained. On the other hand, a result that the crude enzymatic solution co-expressing LaTDH-SmTDH and the crude enzymatic solution expressing LaTDH did not react with ethanolamine and benzylamine was obtained. That is, a result that LaTDH-SmTDH and LaTDH were able to recognize EAP as the substrate was obtained.

(Test Results: EAP Measurement Results by LaTDH)

FIG. 1 is a diagram showing the correlations between the concentration of EAP and the enzyme activity (U/ml) according to an example of the present invention.

According to FIG. 1, a result that there was a correlation between the concentration of EAP (mM) and the enzyme activity (U/ml) was obtained because the coefficient of determination ($R^2$), which is an index of the correlation between the EAP concentration and the enzyme activity (U/ml), in the range of 5 mM to 100 mM was 0.9995. That is, by utilizing LaTDH, a result that the concentration of EAP (mM) could be measured in the range of 5 mM to 100 mM was obtained.

(Construction of Plasmid for Expression of AgPEAOX)

A plasmid (pKK223-3-AgPEAOX) for expression of phenylethylamine oxidase (AgAPEAOX, UniProt ID P46881) derived from *Arthrobacter globiformis* having an amino acid sequence of SEQ ID NO: 9 was prepared using the In-Fusion (registered trademark) HD Cloning Kit (manufactured by Clontech Laboratories, Inc.).

A fragment of the vector (pKK223-3) was prepared by PCR using pKK223-3-CFP-T7 (Refer the publication of WO2007/125779) as a template, pKK223-3 HindIII 3Fw(5'-AAGCTTGGCT GTTTTGGCGG ATGAGAGAAG-3') (SEQ ID NO: 40) and pKK223-3 EcoRI 5Rv(5'-GAAT-TCTGTT TCCTGTGTGA AATTGTTATC-3') (SEQ ID NO: 41) as primers.

1.0 µl of DpnI (manufactured by New England BioLabs, Inc.) was added to the solution after PCR and treated for 1 hours at 37° C., followed by agarose gel electrophoresis, and the gel containing the desired fragment (about 4.6 kbp) was sliced and extracted from the gel using illustra (registered trademark) GFX PCR DNA and Gel Band Purification Kit (manufactured by GE Healthcare).

Synthesis of an AgPEAOX gene having a base sequence of SEQ ID NO: 10 was entrusted to Integrated DNA Technologies by dividing into a first half portion (agpeaox-1-325) in which the DNA sequence of SEQ ID NO: 11 and SEQ ID NO: 12 were sequentially bound in a direction from 5' end to 3' end, and a second half portion (agpeaox-321-638) in which the DNA sequence of SEQ ID NO: 13 and SEQ ID NO: 14 were sequentially bound in a direction from 5' end to 3' end. 15 bases at the 5' end side of the agpeaox_1-325 (SEQ ID NO: 11: CAGGAAACAGAATTC) (SEQ ID NO: 42) and 15 bases at the 3' end side of the agpeaox_321-638 (SEQ ID NO: 14: AAGCTTGGCTGTTTT) (SEQ ID NO: 43) indicate sequences derived from the pKK223-3 vector. The 15 bases (ATCACGTACCTGTCC) (SEQ ID NO: 44) at the 3' end of agpeaox_1-325 and the 15 bases (ATCACGTACCTGTCC) (SEQ ID NO: 45) at the 5' end of agpeaox_321-638 indicate overlapping sequences in the first and second half of AgPEAOX gene.

The vector fragment of pKK223-3, and the two AgPEAOX gene fragments were used to perform in-fusion reaction (50° C., 15 minutes) with the composition of Table 2 to obtain the plasmid (pKK223-3-AgPEAOX) for expression of AgPEAOX. The *E. coli* strain JM109 was transformed with the resulting plasmid.

TABLE 2

| | |
|---|---|
| 5× In-Fusion HD Enzyme Premix | 2.0 µl |
| 38.2 ng/µl pKK223-3 vector fragment | 4.6 µl |
| 50 ng/µl agpeaox_1-325 | 1.7 µl |
| 50 ng/µl agpeaox_321-638 | 1.7 µl |
| | 10.0 µl |

(Recombinant expression of AgPEAOX)

An AgPEAOX producing strain was inoculated into 2.5 ml of LB-amp medium (ampicillin concentration 50 µg/ml) charged into a test tube and seed cultured at 37° C. and 160 rpm overnight. 1 ml of seed culture solution was inoculated into 150 ml of LB-amp medium (ampicillin concentration 50 µg/ml) containing 0.1 mM $CuSO_4$ and 0.1 mM IPTG charged into a Sakaguchi flask and cultured at 25° C. for 16 hours.

A pellet obtained by centrifugation of the culture solution for 6 Sakaguchi flasks at 6,500×g for 10 minutes was resuspended in 20 mM Tris-HCl pH 8.0 containing 2 mM $CuSO_4$.

After ultrasonic pulverization of the bacterial cell suspension, a supernatant obtained by centrifugation at 20,400×g for 15 minutes was buffer-replaced with 20 mM Tris-HCl pH 8.0 using Amicon (registered trademark) Ultra Ultracel-30K (manufactured by Millipore) to obtain a crude enzymatic solution of AgPEAOX.

(Purification of AgPEAOX)

The crude enzyme solution of AgPEAOX was applied to HiScreen (registered trademark) Capto Q (manufactured by GE Healthcare, resin volume 4.7 ml) equilibrated with 20 mM Tris-HCl pH 8.0 to bind to an anion exchange resin.

Thereafter, the resin was washed with 47 ml (10 CV) of 20 mM Tris-HCl (pH 8.0) containing 150 mM NaCl, and 164. 5 ml (35 CV) was fed while linearly increasing NaCl concentration contained in 20 mM Tris-HCl (pH 8.0) from 150 mM to 500 mM to elute AgPEAOX bound to the resin.

The eluted fractions were concentrated by Amicon Ultra Ultracel-30K and purified by HiLoad (registered trademark)

26/60 Superdex 200 columns. 20 mM Tris-HCl (pH 8.0) was used for equilibration of the resin and elution.

The purity of each eluted fraction was assessed by SDS-PAGE, and the fraction containing no contaminant protein was recovered and used as a purified preparation of AgPEAOX.

(Dehydrogenase Activity Measurement of AgPEAOX)

After incubation of 609 μl of the reagent consisting of the composition of Table 3 for 5 minutes at 37° C., 21 μl of the substrate solution (1500 mM EAP) was added and mixed, and the amount of change at $A_{438}$ ($\Delta A_S$) per 1 minute at 37° C. was measured using the spectrophotometer (U-3900, manufactured by Hitachi High-Tech Science Corporation).

Next, 21 μl of ion-exchanged water was added instead of the substrate solution and mixed, and the amount of change at $A_{438}$ ($\Delta A_0$) per 1 minute at 37° C. was measured. 1-methoxy-5-ethylphenazinium ethyl sulfate (1-MPES), and 2-(4-iodophenyl)-3-(4-nitrophenyl)-5-(2,4-disulfophenyl)-2H-tetrazolium monosodium salt (WST-1) manufactured by DOJINDO LABORATORIES were used.

TABLE 3

| | |
|---|---|
| 250 mM Bicine-NaOH pH 8.5 | 226.8 μl |
| 5 mM 1-MPES | 12.6 μl |
| 10 mM WST-1 | 31.5 μl |
| H₂O (ion-exchanged water) | 338.1-x μl |
| AgPEAOX solutions | x μl |
| | 609 μl |

Dehydrogenase activity was calculated based on the following formula:

Dehydrogenase activity (U/ml)=($\Delta A_S - \Delta A_0$)×630×df/(37.0×x)=17.0×($\Delta A_S - \Delta A_0$)×df/x 37.0: Millimolar extinction coefficient (mM⁻¹ cm⁻¹) of WST-1 formazan dye for 438 nm-Wavelength Light
df: Dilution rate of enzyme solution (Quantification of EAP by AgPEAOX)

After incubation of 609 μl of the reagent consisting of the composition of Table 4 for 5 minutes at 37° C., 21 μl of EAP solution (30 mM to 300 mM) or ion-exchanged water was added and mixed, and the change in absorbance ($A_{438}$) at 37° C. for 10 minutes was measured using the spectrophotometer (U-3900). The correlation between $A_{438}$ and the concentration of EAP was evaluated on the vertical axis as $A_{438}$ and the horizontal axis as the concentration of EAP at 10 minutes after the initiation of the measurement.

TABLE 4

| | |
|---|---|
| 250 mM Bicine-NaOH pH 8.5 | 226.8 μl |
| 5 mM 1-MPES | 12.6 μl |
| 10 mM WST-1 | 31.5 μl |
| H₂O (ion-exchanged water) | 246.4 μl |
| 0.069 U/ml (*purified AgPEAOX solution) | 91.4 μl |
| | 609.00 μl |

*Activity (U) was measured at pH 8.5 using a final concentration of 50 mM EAP.

(Test Results: EAP—Measurement Results by AgPEAOX)

Figure 2:
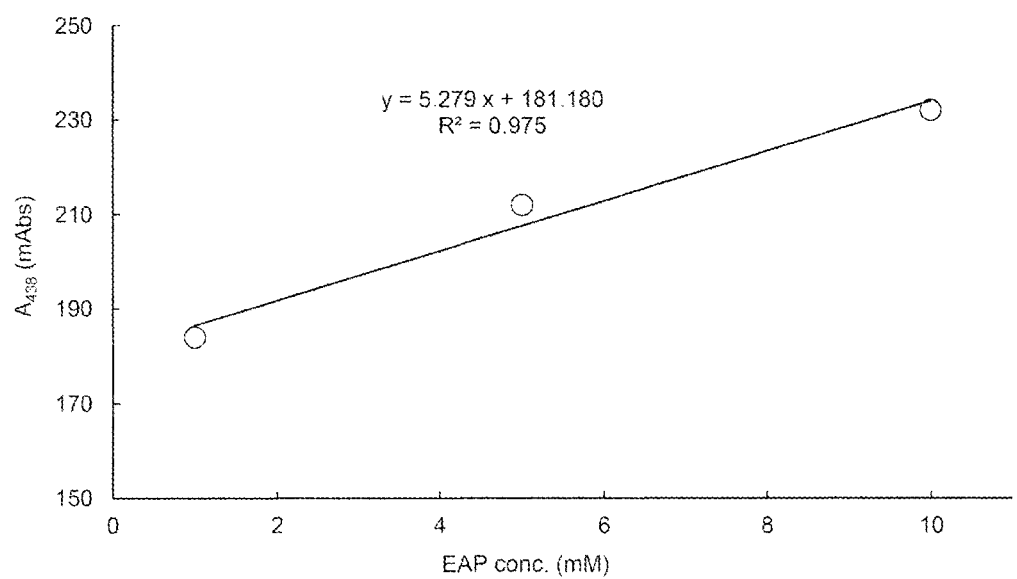
FIG. 2 shows a relationship between a concentration of EAP and absorbance ($A_{438}$, mAbs) according to an example of the present invention.

FIG. 2 is a diagram showing the correlation between the concentration of EAP and the absorbance ($A_{438}$, mAbs) after 10 minutes. According to FIG. 2, since the coefficient of determination ($R^2$), which is indicator of the correlation between the concentration of EAP and the absorbance ($A_{438}$, mAbs) after 10 minutes, is 0.975, a result that there is a correlation between the concentration of EAP (mM) and the absorbance ($A_{438}$ (mAbs)) in the range of 1 mM and 10 mM was obtained. That is, by using the dehydrogenase activity possessed by AgPEAOX, a result that it is possible to measure the concentration of EAP (mM) in the range of 1 mM to 10 mM was obtained. It is assumed that increasing the amount of AgPEAOX to be used makes it easier to quantify the lower concentration of EAP and decreasing the amount of AgPEAOX to be used makes it easier to quantify the higher concentration of EAP.

As described above, it is possible to provide the novel quantitation method for quantifying the concentration of EAP, which is a biomarker of depression, the novel enzyme for quantitation, the novel composition for quantitation, the novel kit for quantification and novel sensor for quantitation by the quantification method for the concentration of EAP according to the present invention in which oxidoreductase is added to a sample containing EAP, oxidoreductase for quantifying EAP added to a sample containing EAP, a composition for quantifying EAP containing oxidoreductase added to a sample containing EAP, a kit for quantifying EAP containing oxidoreductase added to a sample containing EAP, and a sensor for quantifying EAP containing oxidoreductase added to a sample containing EAP.

(Oxidase Activity Measurement of AgPEAOX)

Oxidase activity was measured for the expressed, purified AgPEAOX by the methods described above. After incubating 609 μl of a reagent consisting of the composition of Table 5 at 37° C. for 5 minutes, 21 μl of a substrate solution (1500 mM EAP) was added and mixed, and the amount of change at $A_{555}$ ($\Delta A_S$) per 1 minute at 37° C. was measured using the spectrophotometer (U-3900, manufactured by Hitachi High-Tech Science Corporation).

Next, 21 μl of ion-exchanged water was added instead of the substrate solution and mixed, and the amount of change at $A_{555}$ ($\Delta A_0$) per 1 minute at 37° C. was measured. 4-aminoantipyrine (4-AA) and EAP were manufactured by Fujifilm Wako Pure Chemical Corporation, N-ethyl-N-(2-hydroxy-3-sulfopropyl)-3-methylaniline (TOOS) was manufactured by DOJINDO LABORATORIES, and horseradish peroxidase (POD) was manufactured by TOYOBO Co., LTD..

TABLE 5

| | |
|---|---|
| 0.73 mM 4-AA | |
| 7.5 U/ml POD | 378 μl |
| 150 mM Bicine-NaOH pH 8.5 | |
| 15 mM TOOS | 21 μl |
| H₂O (ion-exchanged water) | 210-x μl |
| AgPEAOX solution | x μl |
| | 609 μl |

The oxidase activity was calculated based on the following formula:

Oxidase activity (U/ml)=($\Delta A_S - \Delta A_0$)×630×df/(39.2× 0.5×x)=32.1×($\Delta A_S - \Delta A_0$)×df/x 39.2: Millimolar extinction coefficient (mM⁻¹cm⁻¹) of 4-AA-TOOS Condensation dye for 555 nm-wavelength light
df: Dilution rate of enzyme solution (pH-Dependence Measurement of Catalytic Reaction of AgPEAOX)

When the pH dependence of catalytic reaction of AgPEAOX was measured, the activity was measured by replacing Bicine-NaOH buffer solution pH 8.5 contained in the reagent for activity measurement in Table 5 with a potassium phosphate buffer solution, MOPS-NaOH buffer solution, or Bicine-NaOH adjusted to a predetermined pH.

(Quantification of EAP by AgPEAOX)

After incubation of 609 µl of the reagent consisting of the composition of Table 6 at 37° C. for 5 minutes, 21 µl of EAP solution (6, 12, 18, 24 or 30 mM) or ion-exchanged water was added and mixed, and the $A_{555}$ change at 37° C. for 5 minutes was measured using the spectrophotometer (U-3900). The correlation between $A_{555}$ and the concentration of EAP was evaluated on the vertical axis as $A_{555}$ at 5 minutes after the initiation of the measurement and on the horizontal axis as the concentration of EAP.

TABLE 6

| | |
|---|---|
| 250 mM Bicine-NaOH pH 8.5 | 226.80 µl |
| 295 mM 4-AA | 0.95 µl |
| 300 U/ml POD | 9.45 µl |
| 15 mM TOOS | 21.00 µl |
| H₂O (ion-exchanged water) | 340.30 µl |
| 2.29 U/ml (*purified AgPEAOX solution) | 10.50 µl |
| | 609.00 µl |

*Activity (U) was measured at pH 8.5 using a final concentration of 50 mM EAP.

(Test Results: pH-Dependence of Catalytic Reaction of AgPEAOX)

Figure 3:
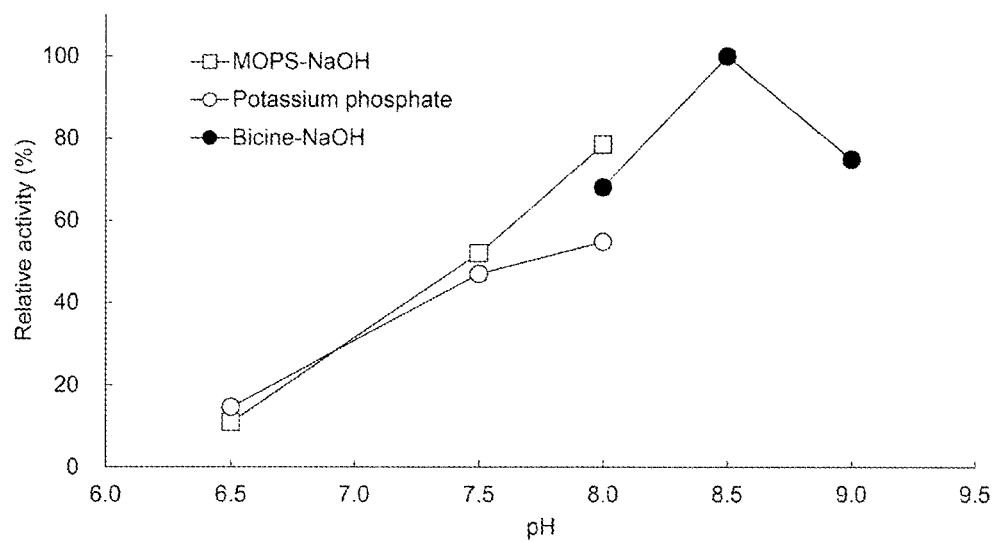
FIG. 3 shows pH dependence of an enzymatic reaction according to an example of the present invention.

FIG. 3 is a diagram showing the pH dependence of an enzymatic reaction according to an example of the present invention. The vertical axis shows the relative activity of AgPEAOX (Relative activity (%)), and the horizontal axis shows the pH, respectively. The relative activity is a relative oxidase activity when the oxidase activity in Bicine-NaOH buffer solution pH 8.5 is set to 100%. From FIG. 3, a result that the optimum pH for the catalytic reaction of AgPEAOX was 8.5 was obtained. Therefore, a reagent was prepared so as to be pH 8.5, and the concentration of EAP was measured using the reagent.

(Test Results: EAP Measurement Results by AgPEAOX)

Figure 4:
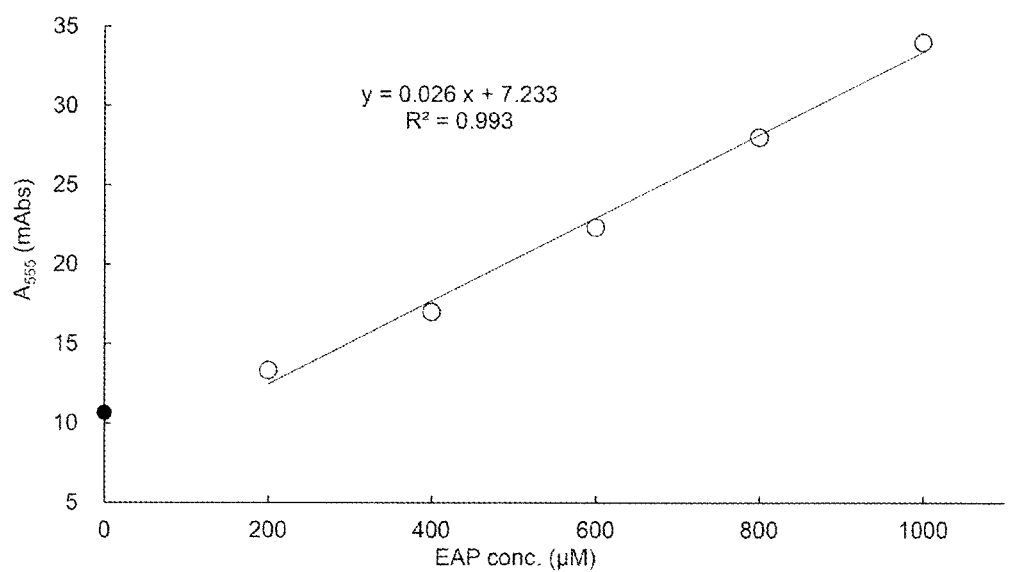
FIG. 4 shows a relationship between a concentration of EAP and absorbance ($A_{555}$, mAbs) according to an example of the present invention.

FIG. 4 is a diagram showing the correlation between the concentration of EAP and the absorbance ($A_{555}$, mAbs) after 5 minutes. According to FIG. 4, since the coefficient of determination ($R^2$), which is indicator of the correlation between the concentration of EAP and the absorbance ($A_{555}$, mAbs) after 5 minutes, is 0.993 in a range of 200 µM and 1000 µM, a result that there is a correlation between the concentration of EAP (µM) and the absorbance ($A_{555}$ (mAbs)) was obtained. That is, by utilizing AgPEAOX, a result that it was possible to measure the concentration of EAP (µM) in the range of 200 µM to 1000 µM was obtained. It is assumed that increasing the amount of AgPEAOX to be used makes it easier to quantify the lower concentration of EAP and decreasing the amount of AgPEAOX to be used makes it easier to quantify the higher concentration of EAP.

As described above, the novel quantitation method for quantifying the concentration of EAP, which is a biomarker of depression, the novel enzyme for quantification, the novel composition for quantification, the novel kit for quantification and novel sensor for quantification can be provided by the quantification method for EAP according to the present invention in which oxidase is added to a sample containing EAP, oxidase for quantifying EAP added to a sample containing EAP, a composition for quantifying EAP added to a sample containing EAP, a kit for quantifying EAP added to a sample containing EAP, and a sensor for quantifying EAP added to a sample containing EAP.

(Construction of Plasmid for Expression of LcAOX)

A plasmid (pKK223-3-LcAOX) for expression of amine oxidase (LcAOX, GenBank ID CDH56199.1) having the amino acid sequence of SEQ ID NO: 15 derived from *Lichtheimia corymbifera* was constructed using the In-Fusion (registered trademark) HD Cloning Kit (manufactured by Clontech Laboratories, Inc.).

The fragment of vector (pKK223-3) was prepared according to the methods described in (Construction of Plasmid for Expression of AgPEAOX).

Synthesis of a LcAOX gene having the base sequence of SEQ ID NO: 16 was entrusted to Integrated DNA Technologies by dividing the gene into an anterior half portion (lcaox_frag1) in which the DNA sequences of SEQ ID NO: 11 and SEQ ID NO: 17 were sequentially bound in a direction from the 5' end to the 3' end, an intermediate portion (lcaox_frag2) described in SEQ ID NO: 18, and the last half portion (lcaox_frag3) in which the DNA sequences of SEQ ID NO: 19 and SEQ ID NO: 14 were sequentially bound in a direction from the 5' end to the 3' end. To take advantage of in-fusion reactions, 15 bases (CCCGAACACCTTGGT) (SEQ ID NO: 46) at the 3' end of lcaox_frag1 and the 5' end of lcaox_frag2 and 15 bases (CAGCATCATCAACAT) (SEQ ID NO: 47) at the 3' end of lcaox_frag2 and the 5' end of lcaox_frag3 were overlapped, respectively.

The vector fragment of pKK223-3 and three LcAOX gene fragments were used to perform the in-fusion reaction (50° C., 15 minutes) with the composition of Table 7 to obtain the plasmid (pKK223-3-LcAOX) for expression of LcAOX. The *E. coli* strain JM109 was transformed with the resulting plasmid.

TABLE 7

| | |
|---|---|
| 5× In-Fusion HD Enzyme Premix | 2.0 µl |
| 40 ng/µl pKK223-3 vector fragment | 1.4 µl |
| 25 ng/µl lcaox_frag1 | 2.2 µl |
| 25 ng/µl lcaox_frag2 | 2.2 µl |
| 25 ng/µl lcaox_frag3 | 2.2 µl |
| | 10.0 µl |

(Construction of Plasmid for Expression of LrHP)

A plasmid for expression (pKK223-3-LrHP) of hypothetical protein (LrHP, GenBank ID CDS02610.1) having an amino acid sequence of SEQ ID NO: 20 derived from *Lichtheimia ramosa* was constructed using the In-Fusion (registered trademark) HD Cloning Kit (manufactured by Clontech Laboratories, Inc.).

The fragment of the vector (pKK223-3) was prepared according to the methods described in (Construction of Plasmid for Expression of AgPEAOX).

Synthesis of a LrHP gene having a base sequence of SEQ ID NO: 21 was entrusted to Integrated DNA Technologies by dividing into an anterior half portion (lrhp_frag1) in which the DNA sequence of SEQ ID NO: 11 and SEQ ID NO: 22 were sequentially bound in a direction from the 5' end to the 3' end, an intermediate portion (lrhp_frag2) in SEQ ID NO: 23, and the last half portion (lrhp_frag3) in which the DNA sequence of SEQ ID NO: 24 and SEQ ID NO: 14 were sequentially bound in a direction from the 5' end to the 3' end. To take advantage of in-fusion reactions, 15 bases (CATTTAGGGCAAGAT) (SEQ ID NO: 48) at the 3' end of lrhp_frag1 and at the 5' end of lrhp_frag2, and 15 bases (CACCATCAACATTTG) (SEQ ID NO: 49) at the 3' end of lrhp_frag2 and at the 5' end of lrhp_frag3, respectively, were overlapped.

The vector fragment of pKK223-3 and three LrHP gene fragments were used to perform in-fusion reaction (50° C., 15 minutes) with the composition of Table 8 to obtain the plasmid (pKK223-3-LrHP) for expression of LrHP. The *E. coli* strain JM109 was transformed with the resulting plasmid.

TABLE 8

| | |
|---|---|
| 5× In-Fusion HD Enzyme Premix | 2.0 µl |
| 40 ng/µl pKK223-3 vector fragment | 1.4 µl |
| 25 ng/µl lrhp_frag1 | 2.2 µl |
| 25 ng/µl lrhp_frag2 | 2.2 µl |
| 25 ng/µl lrhp_frag3 | 2.2 µl |
| | 10.0 µl |

(Construction of Plasmid for Expression of SrAOX3925)

A plasmid (pKK223-3-SrAOX3925) for expression of amine oxidase (SrAOX3925, GenBank ID ORZ03925.1) having an amino acid sequence of SEQ ID NO: 25 derived from *Syncephalastrum racemosum* was constructed using the In-Fusion (registered trademark) HD Cloning Kit (manufactured by Clontech Laboratories, Inc.).

The fragment of the vector (pKK223-3) was prepared according to the methods described in (Construction of Plasmid for Expression of AgPEAOX).

Synthesis of aSrAOX3925 gene having a base sequence of SEQ ID NO: 26 was entrusted into Integrated DNA Technologies by dividing the gene into an anterior half portion (sraox3925-frag1) in which the DNA sequences of SEQ ID NO: 11 and SEQ ID NO: 27 were sequentially bound in a direction from the 5' end to the 3' end, an intermediate portion (sraox3925-frag2) described in SEQ ID NO: 28, and the last half portion (sraox3925-frag3) in which the DNA sequences of SEQ ID NO:29 and SEQ ID NO: 14 were sequentially bound in a direction from the 5' end to the 3' end. To take advantage of in-fusion reactions, 15 bases (CAGTTTTTACCAGAG) (SEQ ID NO: 50) at the 3' end of sraox3925-frag1 and the 5' end of sraox3925-frag2 and 15 bases (GTCGTAGGCCAGCAT) (SEQ ID NO: 51) at the 3' end of sraox3925-frag2 and the 5' end of sraox3925-frag3 were overlapped, respectively.

The vector fragment of pKK223-3 and three SrAOX3925 gene fragments were used to perform In-fusion reaction (50° C., 15 minutes) with the composition of Table 9 to obtain the plasmid (pKK223-3-SrAOX3925) for expression of SrAOX3925. The *E. coli* strain JM109 was transformed with the resulting plasmid.

TABLE 9

| | |
|---|---|
| 5× In-Fusion HD Enzyme Premix | 2.0 µl |
| 40 ng/µl pKK223-3 vector fragment | 1.4 µl |
| 25 ng/µl sraox3925_frag1 | 2.2 µl |
| 25 ng/µl sraox3925_frag2 | 2.2 µl |
| 25 ng/µl sraox3925_frag3 | 2.2 µl |
| | 10.0 µl |

(Construction of Plasmid for Expression of SrAOX3926)

A plasmid (pKK223-3-SrAOX3926) for expression of amine oxidase (SrAOX3926, GenBank ID ORZ03926.1) having an amino acid sequence of SEQ ID NO: 30 derived from *Syncephalastrum racemosum* was constructed using the In-Fusion (registered trademark) HD Cloning Kit (manufactured by Clontech Laboratories, Inc.).

The fragments of the vector (pKK223-3) was prepared according to the methods described in (Construction of Plasmid for Expression of AgPEAOX).

Synthesis of aSrAOX3926 gene having a base sequence of SEQ ID NO: 31 was entrusted to Integrated DNA Technologies by dividing the gene into an anterior half portion (sraox3926-frag 1) in which the DNA sequences of SEQ ID NO: 11 and SEQ ID NO: 32 were sequentially bound in a direction from the 5' end to the 3' end, an intermediate portion (sraox3926-frag 2) described in SEQ ID NO: 33, and the last half portion (sraox3926-frag 3) in which the DNA sequences of SEQ ID NO: 34 and SEQ ID NO: 14 were sequentially bound in a direction from the 5' end to the 3' end. To take advantage of in-fusion reactions, 15 bases (TTGCGCAAAGATATT) (SEQ ID NO: 52) on the 3' end of sraox3926-frag1 and the 5' end of sraox3926-frag2 and 15 bases (GATCCGATGGTAGAC) (SEQ ID NO: 53) on the 3' end of sraox3926-frag2 and the 5' end of sraox3926-frag3 were overlapped, respectively.

The vector fragment of pKK223-3 and three SrAOX3926 gene fragments were used to perform in-fusion reaction (50° C., 15 minutes) with the composition of Table 10 to obtain the plasmid (pKK223-3-SrAOX3926) for expression of SrAOX3926. The *E. coli* strain JM109 was transformed with the resulting plasmid.

TABLE 10

| | |
|---|---|
| 5× In-Fusion HD Enzyme Premix | 2.0 µl |
| 40 ng/µl pKK223-3 vector fragment | 1.4 µl |
| 25 ng/µl sraox3926_frag1 | 2.2 µl |
| 25 ng/µl sraox3926_frag2 | 2.2 µl |
| 25 ng/µl sraox3926_frag3 | 2.2 µl |
| | 10.0 µl |

(Construction of Plasmid for Expression of SrEAOX)

A plasmid (pKK223-3-SrEAOX) for expression of an ethanolamine oxidase (SrEAOX, GenBank ID BAU20376.1) having an amino acid sequence of SEQ ID NO: 35 derived from *Syncephalastrum racemosum* was constructed using the In-Fusion (registered trademark) HD Cloning Kit (manufactured by Clontech Laboratories, Inc.).

The fragment of the vector (pKK223-3) was prepared according to the methods described in (Construction of Plasmid for Expression of AgPEAOX).

Synthesis of a SrEAOX gene having a base sequence of SEQ ID NO: 36 was entrusted into Integrated DNA Technologies by dividing into an anterior half portion (sreaox_frag1) in which the DNA sequence of SEQ ID NO: 11 and SEQ ID NO: 37 were sequentially bound in a direction from the 5' end to the 3' end, an intermediate portion (sreaox_frag2) in SEQ ID NO: 38, and the last half portion (sreaox_frag3) in which the DNA sequence of SEQ ID NO: 39 and SEQ ID NO: 14 were sequentially bound in a direction from the 5' end to the 3' end. To take advantage of in-fusion reactions, 15 bases (CTCCGCAAAGATATA) (SEQ ID NO: 54) at the 3' end of sreaox_frag1 and at the 5' end of sreaox_frag2 and 15 bases (CCAATGGTAGATGGA) (SEQ ID NO: 55) at the 3' end of sreaox_frag2 and at the 5' end of sreaox_frag3, respectively, were overlapped.

The vector fragment of pKK223-3 and three SrEAOX gene fragments were used to perform In-fusion reaction (50° C., 15 minutes) with the compositions of Table 11 to obtain the plasmid (pKK223-3-SrEAOX) for expression of SrEAOX. The *E. coli* strain JM109 was transformed with the resulting plasmid.

TABLE 11

| | |
|---|---|
| 5× In-Fusion HD Enzyme Premix | 2.0 µl |
| 40 ng/µl pKK223-3 vector fragment | 1.4 µl |
| 25 ng/µl sreaox_frag1 | 2.2 µl |
| 25 ng/µl sreaox_frag2 | 2.2 µl |
| 25 ng/µl sreaox_frag3 | 2.2 µl |
| | 10.0 µl |

(Recombinant Expression of Enzyme)

LcAOX, LrHP, SrAOX3925, SrAOX3926, SrEAOX producer strains were inoculated into 2.5 ml of LB-amp medium (ampicillin concentration 50 µg/ml) charged into test tubes and seed cultured at 37° C. and 160 rpm overnight. 1.5 ml of seed culture solution was inoculated into 150 ml of LB-amp medium (ampicillin concentration 50 µg/ml) containing 0.02 mM $CuSO_4$ and 0.1 mM IPTG charged into a Sakaguchi flask and cultured at 25° C. for 16 hours.

The pellet obtained by centrifuging 150 ml of the culture solution at 6500×g for 10 minutes was resuspended in 20 mM Tris-HCl pH 7.5. After ultrasonic pulverization of the bacterial cell suspension, the supernatant was collected by centrifugation at 20,400×g for 15 minutes to serve as a crude enzyme solution.

(Purification of LcAOX, LrHP, SrAOX3925)

The crude enzyme solutions of LcAOX, LrHP or SrAOX3925 were applied to HiScreen (registered trademark) Capto Q (manufactured by GE Healthcare, resin volume 4.7 ml) equilibrated with 20 mM Tris-HCl pH 7.5 to bind to the anion exchange resin.

Thereafter, the resin was washed with 47 ml (10 CV) of 20 mM Tris-HCl (pH 7.5), and 117.5 ml (25 CV) was fed while linearly increasing NaCl concentration contained in 20 mM Tris-HCl (pH 7.5) from 0 mM to 500 mM to elute LcAOX, LrHP or SrAOX3925 bound to the resin.

The eluted fraction was diluted with ion exchanged water three times to reduce salt concentration, and then applied to HiScreen (registered trademark) Capto Q InpRes (manufactured by GE Healthcare, resin amount 4.7 ml) equilibrated with 20 mM Tris-HCl pH 7.5 to bind to the anion exchange resin.

Thereafter, the resin was washed with 23.5 ml (5 CV) of 20 mM Tris-HCl (pH 7.5), and 141 ml (30 CV) of NaCl concentration contained in 20 mM Tris-HCl (pH 7.5) was fed while linearly increasing from 0 mM to 300 mM to elute LcAOX, LrHP or SrAOX3925 bound to the resin.

The eluted fractions were concentrated by Amicon Ultra Ultracel-30K and purified by HiLoad (registered trademark) 26/60 Superdex 200 columns. 10 mM Bis-Tris-HCl (pH 7.0) with 150 mM NaCl was used for equilibration of the resins and elution.

The purity of each eluted fraction was assessed by SDS-PAGE, and the fraction containing no contaminant protein was collected to serve as a purified preparation of LcAOX, LrHP or SrAOX3925.

(Oxidase Activity Measurement of LcAOX, LrHP, SrAOX3925, SrAOX3926, SrEAOX)

Oxidase activity was measured for LcAOX, LrHP, SrAOX3925, SrAOX3926, SrEAOX expressed by the methods described above. After incubating 580 µl of a reagent consisting of the composition of Table 12 at 37° C. for 5 minutes, 20 µl of a substrate solution (1500 mM EAP) was added and mixed, and the amount of change at $A_{555}$ ($\Delta A_S$) per 1 minute at 37° C. was measured using the spectrophotometer (U-3900, manufactured by Hitachi High-Tech Science Corporation). Subsequently, 20 µl of ion-exchanged water was added instead of the substrate solution and mixed, and the amount of change at $A_{555}$ ($\Delta A_0$) per 1 minute at 37° C. was measured.

TABLE 12

| | |
|---|---|
| 0.73 mM 4-AA | |
| 7.5 U/ml POD | 360 µl |
| 150 mM Bicine-NaOH pH 7.5 | |
| 15 mM TOOS | 20 µl |
| $H_2O$ (ion-exchanged water) | 200-x µl |
| Enzyme solution | x µl |
| | 580 µl |

The oxidase activity was calculated based on the following formula:

Oxidase activity (U/ml)=$(\Delta A_S - \Delta A_0) \times 600.0 \times df/(39.2 \times 0.5 \times x) = 30.6 \times (\Delta A_S - \Delta A_0) \times df/x$ 39.2: Millimolar extinction coefficient ($mM^{-1}cm^{-1}$) of 4-AA-TOOS Condensation dye for 555 nm-wavelength light df: Dilution rate of enzyme solution (Quantification of EAP by LrHP)

After incubation of 580.0 µl of the reagent consisting of the composition of Table 13 for 5 minutes at 37° C., 20.0 µl of EAP solution (3, 6, 18 or 30 mM) or ion-exchanged water was added and mixed, and the change at $A_{555}$ was measured for 20 minutes at 37° C. using the spectrophotometer (U-3900). The correlation between $A_{555}$ and the concentration of EAP was evaluated on the vertical axis as $A_{555}$ and on the horizontal axis as the EAP concentration at 20 minutes after the initiation of the measurement.

TABLE 13

| | |
|---|---|
| 250 mM Bicine-NaOH pH 7.5 | 216.0 µl |
| 295 mM 4-AA | 0.9 µl |
| 300 U/ml POD | 9.0 µl |
| 15 mM TOOS | 20.00 µl |
| $H_2O$ (ion-exchanged water) | 294.1 µl |
| 0.14 U/ml (*purified LrHP solutions) | 40.0 µl |
| | 580.0 µl |

*Activity (U) was measured at pH 7.5 using a final concentration of 50 mM EAP.

(Quantification of EAP by LrHP by Electrochemical Methods)

20 µl of 150 mM Bicine-NaOH buffer solution (pH 7.5), 15 µl of 1.5 M potassium chloride solution, and 5 µl of LrHP solution (0.14 U/ml) were applied and mixed on a SCREEN-PRINTED ELECTRODES (manufactured by DropSens, Product Number DRP-C110). A dedicated connector (DRP-CAC) was then used to connect to ALS electrochemical analyzer 814D. Chronoamperometric measurements were performed at +600 mV (Ag/AgCl). Subsequently, 2 µl of EAP solution at each concentration was added, and the current value at 100 seconds after the initiation of measurement was recorded. Similar experiments were carried out using 5 µl of ultrapure water (ion-exchanged water) instead of LrHP solution as a control experiment.

(Test Results: Oxidase Activity Measurement of LcAOX, LrHP, SrAOX3925, SrAOX3926, SrEAOX)

The oxidase activity of the crude enzymatic solution of LcAOX, LrHP, SrAOX3925, SrAOX3926, SrEAOX against EAP was 1.8, 5.8, 2.6, 0.2 and 16 U/L, respectively. For LcAOX, LrHP, SrAOX3925, it showed 0.11, 0.31 and 0.16 U/ml activities, respectively, even after being purified. Thus, LcAOX, LrHP, SrAOX3925 were shown to catalyze the reaction, each alone, to oxidize EAP to produce hydrogen peroxide. It is considered that SrAOX3926, SrEAOX show oxidase activity against EAP even after being purified to a level free of contaminant proteins.

(Test Results: EAP Measurement Results by LrHP)

Figure 5:
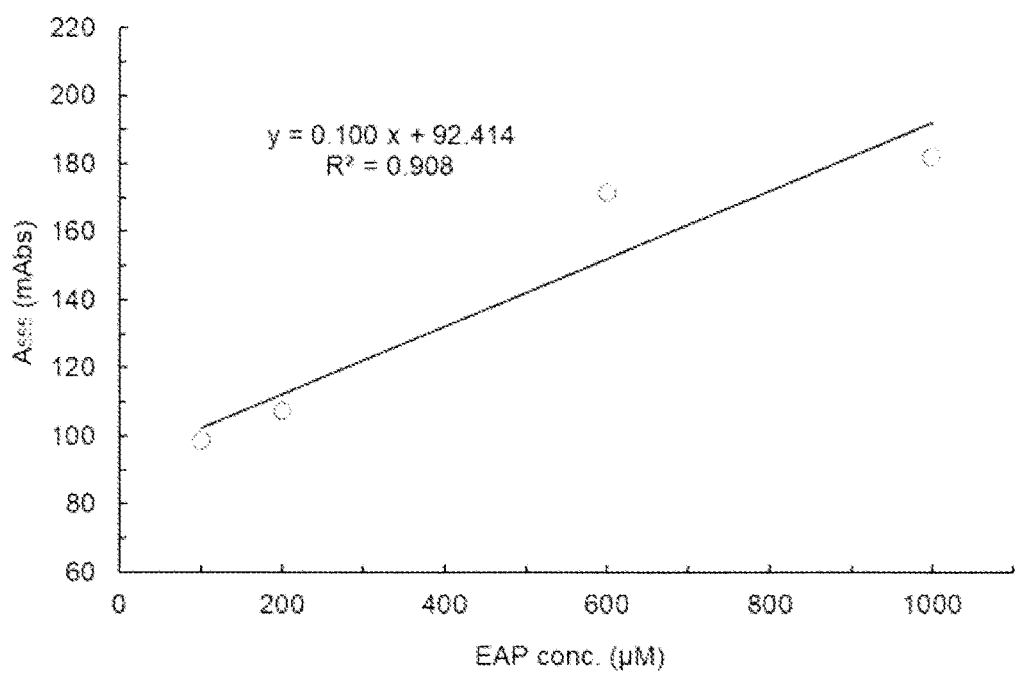
FIG. 5 shows a relationship between a concentration of EAP and absorbance ($A_{555}$, mAbs) according to an example of the present invention.

FIG. 5 is a diagram showing the correlation between the concentration of EAP and the absorbance ($A_{555}$, mAbs) after 20 minutes. According to FIG. 5, since the coefficient of determination ($R^2$), which is indicator of the correlation between the concentration of EAP and the absorbance ($A_{555}$, mAbs) after 20 minutes, is 0.908 in the range of 100 µM to 1000 µM, a result that there is a correlation between the concentration of EAP (µM) and the absorbance ($A_{555}$ (mAbs) was obtained. That is, by utilizing LrHP, a result that it is possible to measure the concentration of EAP (µM) in the range of 100 µM to 1000 µM. It is assumed that increasing the amount of LrHP to be used makes it easier to quantify the lower concentration of EAP and decreasing the amount of LrHP to be used makes it easier to quantify the higher concentration of EAP. It is believed that the concentration of EAP (µM) can be measured even when LcAOX, SrAOX3925, SrAOX3926 or SrEAOX is used instead of LrHP.

(Test Results: Quantification of EAP by LrHP by Electrochemical Methods)

Figure 6:
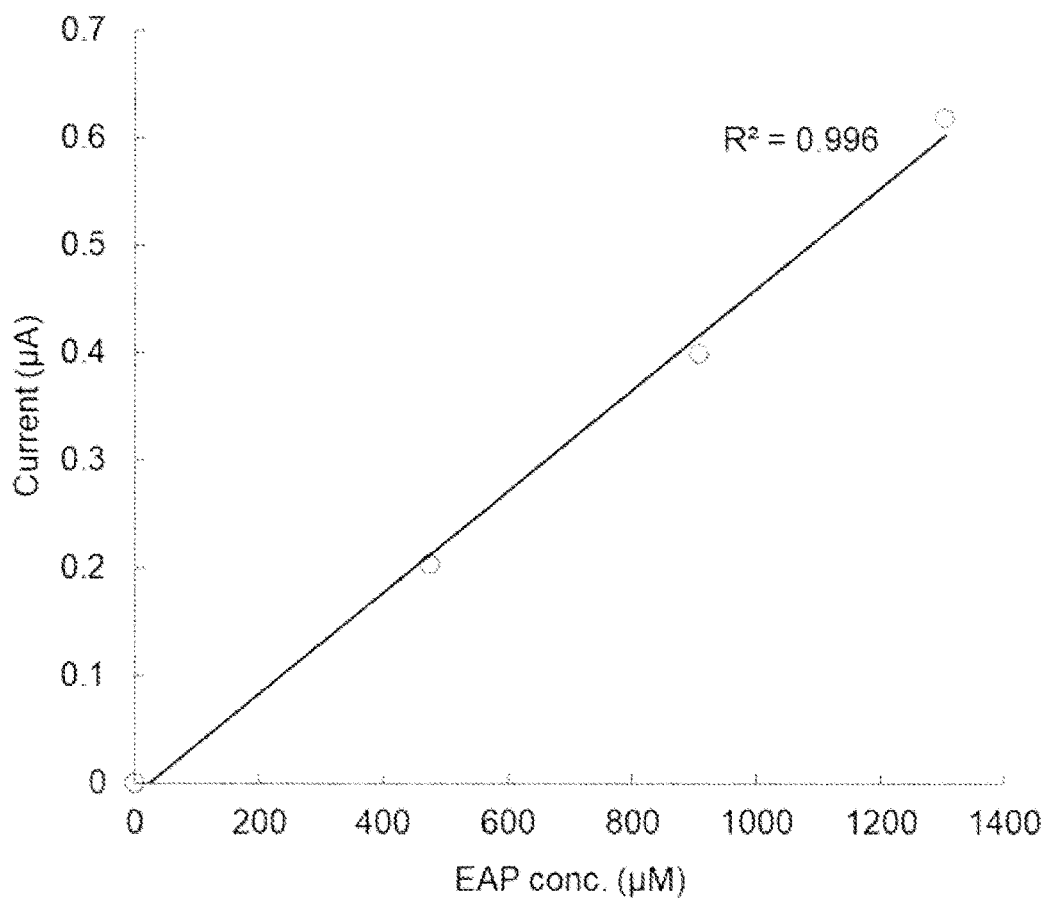
FIG. 6 shows a relationship between a concentration of EAP and a current value (μA) according to an example of the present invention.
Figure 7:
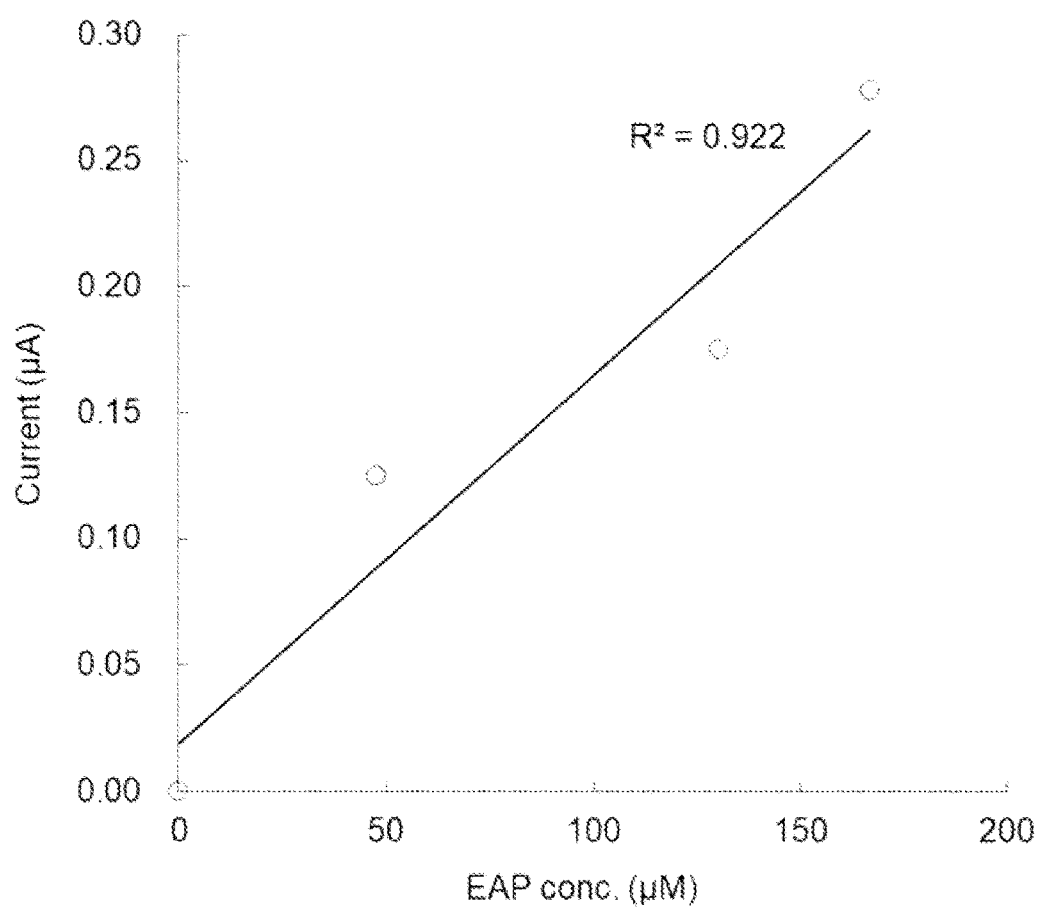
FIG. 7 shows a relationship between a concentration of EAP and a current value (μA) according to an example of the present invention.

FIG. 6 is a diagram plotting the current value at 100 seconds after the initiation of measurement when 0 µM to 1400 µM of EAP is added. FIG. 7 is a diagram plotting the current value at 100 seconds after the initiation of measurement when 0 µM to 170 µM of EAP is added. In both results, it was found that as the concentration of EAP increased, the current value also increased. Similar experiments were performed when 5 µl of ultrapure water (ion-exchanged water) was used instead of EAPOX solution as a control, but no increase in the response current was seen when EAP was added. Therefore, it was assumed that the quantification of EAP was also possible by the electrochemical measurement. It is assumed that increasing the amount of LrHP to be used makes it easier to quantify the lower concentration of EAP and decreasing the amount of LrHP to be used makes it easier to quantify the higher concentration of EAP. It is believed that the concentration of EAP (µM) can be measured even when AgPEAOX, LcAOX, SrAOX3925, SrAOX3926 or SrEAOX is used instead of LrHP.

As described above, a novel quantitation method for quantifying the concentration of EAP, which is a biomarker of depression, a novel enzyme for quantification, a novel composition for quantification, a novel kit for quantification and a novel sensor for quantification can be provided by the quantification method of EAP in which oxidase is added to a sample containing EAP according to the present invention, the oxidase for quantification which is added to a sample containing EAP, the composition for the quantification of EAP contains oxidase which is added to a sample containing EAP, the kit for the quantification of EAP contains oxidase which is added to a sample containing EAP, and the sensor for the quantification of EAP contains oxidase which is added to a sample containing EAP.

According to the present invention, a novel quantification method for quantifying the concentration of EAP, which is a biomarker of depression, an enzyme for quantitation, a composition for quantitation, a kit for quantitation or a sensor for quantitation is provided.

What is claimed is:

1. A quantitation method of ethanolamine phosphate comprising:
   adding an oxidoreductase to a sample containing ethanolamine phosphate, and
   allowing the oxidoreductase to act on the ethanolamine phosphate as a substrate,
   wherein the oxidoreductase is an oxidoreductase belonging to EC NO: 1.4 or EC NO: 1.5.

2. The quantitation method of ethanolamine phosphate according to claim 1 further comprising:
   reducing a mediator by adding the oxidoreductase; and
   reacting the reduced mediator with a reagent to determine concentration of the ethanolamine phosphate in the sample.

3. The quantitation method of ethanolamine phosphate according to claim 1,
   wherein
   the oxidoreductase is an oxidase, and
   hydrogen peroxide produced by adding the oxidase is reacted with a reagent to determine a concentration of the ethanolamine phosphate.

4. The quantitation method of ethanolamine phosphate according to claim 1, wherein the oxidoreductase is an oxidase belonging to EC NO: 1.4.3 or EC NO: 1.5.3.

5. The quantitation method according to claim 1, wherein the oxidoreductase is selected from the group consisting of primary amine dehydrogenase, monoamine dehydrogenase, diamine dehydrogenase, polyamine dehydrogenase, ethanolamine dehydrogenase, tyramine dehydrogenase, phenylethylamine dehydrogenase, benzylamine dehydrogenase, histamine dehydrogenase, serotonin dehydrogenase, spermine dehydrogenase, spermidine dehydrogenase, β-alanine dehydrogenase, γ-aminobutyric acid (GABA) dehydrogenase, taurine dehydrogenase, cadaverine dehydrogenase, and agmatine dehydrogenase.

6. The quantitation method according to claim 3, wherein the oxidase is selected from the group consisting of primary amine oxidase, monoamine oxidase, diamine oxidase, polyamine oxidase, ethanolamine oxidase, tyramine oxidase, phenylethylamine oxidase, benzylamine oxidase, histamine oxidase, serotonin oxidase, spermine oxidase, spermidine oxidase, β-alanine oxidase, γ-aminobutyric acid (GABA) oxidase, taurine oxidase, cadaverine oxidase, and agmatine oxidase.

7. The quantitation method according to claim 5, wherein the oxidoreductase is a taurine dehydrogenase that includes a large subunit.

* * * * *

SEQUENCE LISTING

<160> NUMBER OF SEQ ID NOS: 55

<210> SEQ ID NO 1
<211> LENGTH: 463
<212> TYPE: PRT
<213> ORGANISM: Paracoccus denitrificans

<400> SEQUENCE: 1

```
Met Gln Ala Ile Glu Lys Arg Ala Gly Ala Leu Pro Tyr Asp Pro Leu
1               5                   10                  15

Tyr Asp Pro Val Thr Ala Arg Gly Leu Gly Pro Arg Ser Asp Tyr Ala
                20                  25                  30

Pro Thr Tyr Trp Ile Gly Thr Ala Gly Ala Pro Pro Pro Asp Asp Gly
            35                  40                  45

Pro Val Thr Gly Asp Met Asp Ala Asp Val Val Val Ile Gly Ser Gly
        50                  55                  60

Tyr Thr Gly Leu Ser Cys Ala Leu His Leu Ala Lys Met His Gly Ile
65                  70                  75                  80

Lys Ala Val Val Leu Glu Ala Asn Gly Val Ala Tyr Gly Cys Ser Thr
                85                  90                  95

Arg Asn Gly Gly Gln Ala Gln Val Ser Ser Gly Arg Leu Lys Arg Ser
                100                 105                 110

Gln Trp Ile Glu Arg Trp Gly Leu Asp Val Ala Arg Arg Leu His Ala
            115                 120                 125

Glu Val Cys Glu Gly Phe Asp Leu Phe Arg Gly Leu Ile Arg Asp His
        130                 135                 140

Ala Ile Asp Cys Asp Pro Gln Asp Gly Gly His Tyr Tyr Ile Ala His
```

Lys Ala Ser Ala Met Pro Ala Leu Glu Lys Glu Thr Ala Leu Leu Arg
145                 150                 155                 160

Asp Thr Phe Gly Tyr Asp Ala Arg Met Ile Ser Arg Asp Glu Leu His
            165                 170                 175

Glu Thr Val Ala Arg Asp Gln Glu Ala His Gly Ala Met Trp Glu Ala
        180                 185                 190

Asp Gly Val Gly Ile His Ala Ala Lys Leu Ala Phe Gly Tyr Leu Arg
    195                 200                 205

Ala Ala Arg Glu Leu Gly Ala Arg Val His Val Asp Ser Pro Val Gln
210                 215                 220

Gly Trp Glu Tyr Arg Asn Gly Val His His Leu Arg Thr Pro Gly Gly
225                 230                 235                 240

Thr Val Arg Ala Arg Arg Val Ala Val Ala Thr Ala Ala Tyr Ala Pro
            245                 250                 255

Arg Ser Leu His Pro Arg Leu Arg Asp Arg Leu Met Pro Ile Met Ser
        260                 265                 270

Asn Ser Ile Val Thr Arg Val Leu Thr Pro Ala Glu Leu Glu Ala Val
    275                 280                 285

Gly Ile Arg Lys Leu Ser Pro Leu Thr Asp Thr Arg Thr Leu Arg His
290                 295                 300

Tyr Tyr Arg Leu Leu Pro Asp Asn Arg Leu Gln Ile Gly Ser Arg Ala
305                 310                 315                 320

Ala Ile Thr Gly Arg Asp Ala Ala Asn Pro Ala His Leu Asp Ala Leu
            325                 330                 335

Arg Glu Gly Met Ala Arg Lys Phe Pro Ala Leu Arg Gly Ile Ala Leu
        340                 345                 350

Asp Tyr Ser Trp Trp Gly Trp Val Asp Val Ser His Asp Met Met Pro
    355                 360                 365

Arg Ile Thr Gly Leu Pro Asp Leu Pro Gly Ala Phe Tyr Ala Leu Gly
370                 375                 380

Tyr Gly Gly Asn Gly Val Met Tyr Ser Ala Met Ala Gly Arg Arg Met
385                 390                 395                 400

Ala Gln Leu Val Ala Gly Glu Ala Val Pro Asp Leu Pro Ile Phe Asn
            405                 410                 415

Asn Glu Leu Pro His Glu Gly Trp Arg Thr Pro Phe Arg Arg Leu Gly
        420                 425                 430

Gln Trp Gly Leu Tyr Lys Phe Tyr His Tyr Arg Asp Glu Arg Arg
    435                 440                 445

450                 455                 460

<210> SEQ ID NO 2
<211> LENGTH: 1392
<212> TYPE: DNA
<213> ORGANISM: Paracoccus denitrificans

<400> SEQUENCE: 2
atgcaagcta ttgaaaaacg tgcaggcgcc ttgccttacg accctcttta tgatcctgtt      60
accgcacgtg gactgggtcc gcgctccgat tatgctccga cctactggat cggcaccgca     120
ggagcacctc ccccgatga tggcccggtt accgtgata tggacgcaga gtagttgtt       180 attgggagcg gttacaccgg gctgtcatgc gctttacatc tggcaaaaat gcatgggatc     240
aaggcagtgg tcttggaggc caatggtgtt gcctatggct gctctactcg gaatggcggc     300
caggcgcagg tttcatctgg ccgccttaag agatctcaat ggattgaacg ctgggtctt     360

```
gatgtcgccc gtcgtcttca cgccgaagtt tgtgagggtt tcgatctgtt ccgtggcctt    420
attcgtgatc acgctatcga ttgtgatccg caagacggtg ggcattatta tatcgcacat    480
aaagcaagcg ctatgccggc cttagagaag gagacagccc tgctgcgtga ctactttgga   540
tatgacgccc gtatgattag ccgtgacgag ttgcatgaaa ccgttgcgcg tgaccaggaa    600
gcacatggtg ccatgtggga agccgatggt gtgggtatac acgcggcaaa attagccttc    660
ggttatttac gtgccgcaag agagctgggg gcccgtgttc acgtagacag cccggtgcaa    720
ggctgggaat accgtaatgg tgtgcatcac ctgcgcaccc cgggcggaac tgttcgcgcg    780
cgtcgcgtgg cagtggccac agcggcctac gcgccgcgtt cattacatcc tcgccttcgt    840
gaccgtctga tgcctatcat gagtaacagc atcgtgacac gcgtgcttac tccggcggaa    900
cttgaagcag tcggtattag aaaactgagt ccgctgacgg atacacggac actgcgccat    960
tattatcggt tgttaccaga caatcgcctg cagattggta gtagagcagc gataacgggt   1020
cgggacgcgg ctaatcctgc gcatctggac gcgctgcgcg agggtatggc gcgcaaattt   1080
cccgctctga gaggcattgc tctggattac tcctggtggg gttgggtaga tgtctcgcac   1140
gatatgatgc cacgcataac ggggttaccc gatctgcccg gagcttttta cgctttaggg   1200
tatggcggca acggagtaat gtattcggct atggctggcc gccggatggc gcagttggta   1260
gcggggggaag ctgtcccaga tttaccaatt tttaacaacg aactgccaca cgaaggatgg   1320
cggacgccat ttcgccggct gggacagtgg ggattgtata aatttatca ttatagagat   1380
gaaagacggt aa                                                       1392
```

<210> SEQ ID NO 3
<211> LENGTH: 139
<212> TYPE: PRT
<213> ORGANISM: Paracoccus denitrificans

<400> SEQUENCE: 3

Met Pro Arg Thr Leu Thr Ala Ala Asp Leu Gln Ala Thr Phe Asp Ala
1               5                   10                  15

Phe Asn Arg His Asp Ile Asp Gly Val Met Thr His Phe Ala Asp Asp
            20                  25                  30

Cys Val Phe Tyr Thr Val Ser Gly Glu His Glu Tyr Gly Asn Arg Ile
        35                  40                  45

Glu Gly Lys Ala Ala Ile Ala Arg Ala Phe Glu Ala Val Trp Thr Thr
    50                  55                  60

Met Pro Asp Val Gln Trp Ala Glu His Thr His Phe Leu Ser Glu Asp
65                  70                  75                  80

Gly Thr Arg Gly Val Ser Gln Trp Thr Phe Arg Ala Thr Asn Pro Asp
                85                  90                  95

Gly Ser Arg Thr Glu Val Gln Gly Val Asp Leu Phe Arg Ile Ala Asp
            100                 105                 110

Gly Arg Ile Val Glu Lys Gln Ala Ile Arg Lys Gln Arg Pro Ala Ile
        115                 120                 125

Pro Ala Thr Ala Pro Ala Leu Ala Gly Lys
    130                 135

<210> SEQ ID NO 4
<211> LENGTH: 420
<212> TYPE: DNA
<213> ORGANISM: Paracoccus denitrificans

<400> SEQUENCE: 4

```
atgccacgta ctttgaccgc tgccgactta caggccacat tcgacgcatt taacagacac    60
gatattgacg gtgtcatgac gcactttgcc gatgattgtg tattctatac cgtttccggc   120
gaacatgagt acggcaatcg cattgaaggc aaagcggcga tagcgcgtgc attcgaagcc   180
gtttggacca ccatgcccga tgtgcaatgg gcagaacata cacattttct gagcgaagac   240
ggaactcgcg gtgttagtca gtggacgttt cgcgcgacta atccggatgg atcacgtacg   300
gaggtgcagg gggtggatct gtttcgtatc gcggatgggc ggattgtcga gaaacaagca   360
attcggaagc agagacctgc aatcccggct gctacagcac cggctcttgc cggtaaataa   420
```

<210> SEQ ID NO 5
<211> LENGTH: 30
<212> TYPE: DNA
<213> ORGANISM: Artificial Sequence
<220> FEATURE:
<223> OTHER INFORMATION: Artificially Synthesized Primer Sequence
<400> SEQUENCE: 5

```
agacggtaag gatccatgcc acgtactttg                                     30
```

<210> SEQ ID NO 6
<211> LENGTH: 30
<212> TYPE: DNA
<213> ORGANISM: Artificial Sequence
<220> FEATURE:
<223> OTHER INFORMATION: Artificially Synthesized Primer Sequence
<400> SEQUENCE: 6

```
acggagctcg aattcttatt taccggcaag                                     30
```

<210> SEQ ID NO 7
<211> LENGTH: 30
<212> TYPE: DNA
<213> ORGANISM: Artificial Sequence
<220> FEATURE:
<223> OTHER INFORMATION: Artificially Synthesized Primer Sequence
<400> SEQUENCE: 7

```
ggatccttac cgtctttcat ctctataatg                                     30
```

<210> SEQ ID NO 8
<211> LENGTH: 30
<212> TYPE: DNA
<213> ORGANISM: Artificial Sequence
<220> FEATURE:
<223> OTHER INFORMATION: Artificially Synthesized Primer Sequence
<400> SEQUENCE: 8

```
gaattcgagc tccgtcgaca agcttgcggc                                     30
```

<210> SEQ ID NO 9
<211> LENGTH: 638
<212> TYPE: PRT
<213> ORGANISM: Arthrobacter globiformis
<400> SEQUENCE: 9

```
Met Thr Pro Ser Thr Ile Gln Thr Ala Ser Pro Phe Arg Leu Ala Ser
1               5                   10                  15

Ala Gly Glu Ile Ser Glu Val Gln Gly Ile Leu Arg Thr Ala Gly Leu
            20                  25                  30

Leu Gly Pro Glu Lys Arg Ile Ala Tyr Leu Gly Val Leu Asp Pro Ala
        35                  40                  45
```

```
Arg Gly Ala Gly Ser Glu Ala Glu Asp Arg Arg Phe Arg Val Phe Ile
    50                  55                  60

His Asp Val Ser Gly Ala Arg Pro Gln Glu Val Thr Val Ser Val Thr
 65              70                  75                      80

Asn Gly Thr Val Ile Ser Ala Val Glu Leu Asp Thr Ala Ala Thr Gly
                 85                  90                  95

Glu Leu Pro Val Leu Glu Glu Phe Glu Val Val Glu Gln Leu Leu
            100             105             110

Ala Thr Asp Glu Arg Trp Leu Lys Ala Leu Ala Ala Arg Asn Leu Asp
            115             120             125

Val Ser Lys Val Arg Val Ala Pro Leu Ser Ala Gly Val Phe Glu Tyr
    130             135             140

Ala Glu Glu Arg Gly Arg Arg Ile Leu Arg Gly Leu Ala Phe Val Gln
145             150             155                     160

Asp Phe Pro Glu Asp Ser Ala Trp Ala His Pro Val Asp Gly Leu Val
                165             170             175

Ala Tyr Val Asp Val Val Ser Lys Glu Val Thr Arg Val Ile Asp Thr
            180             185             190

Gly Val Phe Pro Val Pro Ala Glu His Gly Asn Tyr Thr Asp Pro Glu
        195             200             205

Leu Thr Gly Pro Leu Arg Thr Thr Gln Lys Pro Ile Ser Ile Thr Gln
    210             215             220

Pro Glu Gly Pro Ser Phe Thr Val Thr Gly Asn His Ile Glu Trp
225             230             235             240

Glu Lys Trp Ser Leu Asp Val Gly Phe Asp Val Arg Glu Gly Val Val
            245             250             255

Leu His Asn Ile Ala Phe Arg Asp Gly Asp Arg Leu Arg Pro Ile Ile
        260             265             270

Asn Arg Ala Ser Ile Ala Glu Met Val Val Pro Tyr Gly Asp Pro Ser
    275             280             285

Pro Ile Arg Ser Trp Gln Asn Tyr Phe Asp Thr Gly Glu Tyr Leu Val
    290             295             300

Gly Gln Tyr Ala Asn Ser Leu Glu Leu Gly Cys Asp Cys Leu Gly Asp
305             310             315             320

Ile Thr Tyr Leu Ser Pro Val Ile Ser Asp Ala Phe Gly Asn Pro Arg
                325             330             335

Glu Ile Arg Asn Gly Ile Cys Met His Glu Glu Asp Trp Gly Ile Leu
            340             345             350

Ala Lys His Ser Asp Leu Trp Ser Gly Ile Asn Tyr Thr Arg Arg Asn
        355             360             365

Arg Arg Met Val Ile Ser Phe Phe Thr Thr Ile Gly Asn Tyr Asp Tyr
    370             375             380

Gly Phe Tyr Trp Tyr Leu Tyr Leu Asp Gly Thr Ile Glu Phe Glu Ala
385             390             395             400

Lys Ala Thr Gly Val Val Phe Thr Ser Ala Phe Pro Glu Gly Gly Ser
                405             410             415

Asp Asn Ile Ser Gln Leu Ala Pro Gly Leu Gly Ala Pro Phe His Gln
            420             425             430

His Ile Phe Ser Ala Arg Leu Asp Met Ala Ile Asp Gly Phe Thr Asn
        435             440             445

Arg Val Glu Glu Glu Asp Val Val Arg Gln Thr Met Gly Pro Gly Asn
    450             455             460

Glu Arg Gly Asn Ala Phe Ser Arg Lys Arg Thr Val Leu Thr Arg Glu
```

| | | | | 465 | | | | | 470 | | | | | 475 | | | | | 480 |
|---|---|---|---|---|---|---|---|---|---|---|---|---|---|---|---|---|---|---|---|
Ser Glu Ala Val Arg Glu Ala Asp Ala Arg Thr Gly Arg Thr Trp Ile
                485                 490                 495

Ile Ser Asn Pro Glu Ser Lys Asn Arg Leu Asn Glu Pro Val Gly Tyr
            500                 505                 510

Lys Leu His Ala His Asn Gln Pro Thr Leu Leu Ala Asp Pro Gly Ser
            515                 520                 525

Ser Ile Ala Arg Arg Ala Ala Phe Ala Thr Lys Asp Leu Trp Val Thr
        530                 535                 540

Arg Tyr Ala Asp Asp Glu Arg Tyr Pro Thr Gly Asp Phe Val Asn Gln
545                 550                 555                 560

His Ser Gly Gly Ala Gly Leu Pro Ser Tyr Ile Ala Gln Asp Arg Asp
                565                 570                 575

Ile Asp Gly Gln Asp Ile Val Val Trp His Thr Phe Gly Leu Thr His
            580                 585                 590

Phe Pro Arg Val Glu Asp Trp Pro Ile Met Pro Val Asp Thr Val Gly
        595                 600                 605

Phe Lys Leu Arg Pro Glu Gly Phe Phe Asp Arg Ser Pro Val Leu Asp
        610                 615                 620

Val Pro Ala Asn Pro Ser Gln Ser Gly Ser His Cys His Gly
625                 630                 635

<210> SEQ ID NO 10
<211> LENGTH: 1914
<212> TYPE: DNA
<213> ORGANISM: Arthrobacter globiformis

<400> SEQUENCE: 10

```
atgacaccgt caacgattca aactgccagt ccatttcgtt tagcatcggc tggcgagatc    60
agcgaagtac aaggaatcct gcgcactgca ggcttattgg gtcccgagaa acgcattgct   120
tacttggggg tccttgatcc tgctcgtggg gccggcagcg aagcggaaga tcgccgtttc   180
cgcgttttta tccacgatgt ctcgggagcg cgccctcaag aagtgactgt gtcggtaacg   240
aacggtacgg tcatttccgc cgtcgaattg atacagccg ccactggtga attaccggta   300
ttggaagaag agttcgaggt gtagaacaa ctgctggcaa cggatgagcg ttggttaaag   360
gcacttgcgg ctcgtaacct tgatgttagt aaagtacgcg tagctcctct ttctgctggt   420
gtctttgagt acgccgaaga acgcggccgt cgcatccttc gtggcttggc ttttgtacag   480
gacttcccag aagattcggc ttgggcacat cccgtggacg gcttgtggc ctacgttgac   540 gtggtatcaa aggaagtcac ccgtgtaatt gatactgggg ttttccccgt accggcggaa   600
catgggaact acacagatcc cgagttgaca ggtcctcttc gcacgacaca gaagcctatc   660
agcattacac agcccgaagg tccttcattt acggtgacgg gcggcaacca tatcgagtgg   720
gagaaatggt ccctggacgt cggattcgac gttcgtgagg gtgtggtgct tcataacatt   780
gcttttcgtg acggagatcg ccttcgcccg attatcaacc gcgcgtccat tgctgaaatg   840
gtcgtccctt acggggatcc ttctcccatt cgctcgtggc agaactattt cgatacgggg   900
gagtacttag tcggccagta cgccaactca ttggaacttg gctgtgattg tcttggagat   960
atcacgtacc tgtcccctgt tatctcagat gcgttcggaa accctcgtga aatccgcaac  1020
gggatctgta tgcatgaaga agattggggg attcttgcaa acattcgga tttatggtcc  1080 ggcatcaact atacgcgtcg caatcgtcgt atggtgattt cattttttcac aaccatcggg  1140 aattatgatt atgggtttta ttggtatctg tacctggacg gaacgatcga gtttgaagca  1200
```

```
aaggcaactg gagtggtatt cacgtctgcg tttcccgagg gcgggtccga taatattagc    1260
cagcttgccc caggccttgg cgctccgttt catcaacaca tcttctcggc ccgtttagac    1320
atggctatcg atggattcac gaatcgtgtt gaggaagagg atgttgtgcg ccaaacgatg    1380
ggacccggca acgaacgtgg gaatgcgttc agtcgtaaac gtacggttct gacgcgcgaa    1440
tcagaagcgg tacgtgaggc agacgcacgt acaggtcgca cctggatcat ctcaaatccc    1500
gagtctaaga atcgtcttaa tgaacccgta gggtataagt tacacgccca caaccaaccg    1560
accttactgg cggaccctgg aagctcaatc gctcgtcgcg cggccttcgc caccaaagat    1620
ctgtgggtaa cacgttacgc cgacgatgag cgctatccca caggagactt cgtaaaccag    1680
cattccgggg gcgcgggttt gccatcctat attgcccagg accgcgacat cgatggccaa    1740
gacatcgtag tatggcatac atttggactt acccactttc cacgtgtgga ggactggcca    1800
attatgccgg tggacactgt aggtttcaag cttcgcccag aaggattctt tgaccgcagt    1860
cctgtgctgg atgtaccagc caatccctcc caatctggtt cacactgcca tgga         1914
```

<210> SEQ ID NO 11
<211> LENGTH: 15
<212> TYPE: DNA
<213> ORGANISM: Artificial Sequence
<220> FEATURE:
<223> OTHER INFORMATION: pKK223-3

<400> SEQUENCE: 11

```
caggaaacag aattc                                                       15
```

<210> SEQ ID NO 12
<211> LENGTH: 975
<212> TYPE: DNA
<213> ORGANISM: Arthrobacter globiformis

<400> SEQUENCE: 12

```
atgacaccgt caacgattca aactgccagt ccatttcgtt tagcatcggc tggcgagatc      60
agcgaagtac aaggaatcct gcgcactgca ggcttattgg gtcccgagaa acgcattgct     120
tacttggggg tccttgatcc tgctcgtggg gccggcagcg aagcggaaga tcgccgtttc     180
cgcgttttta tccacgatgt ctcgggagcg cgccctcaag aagtgactgt gtcggtaacg     240
aacggtacgg tcatttccgc cgtcgaattg gatacagccg ccactggtga attaccggta     300
ttggaagaag agttcgaggt tgtagaacaa ctgctggcaa cggatgagcg ttggttaaag     360
gcacttgcgc tcgtaacct  tgatgttagt aaagtacgcg tagctcctct ttctgctggt     420
gtctttgagt acgccgaaga acgcggccgt cgcatccttc gtggcttggc ttttgtacag     480
gacttcccag aagattcggc ttgggcacat cccgtggacg ggcttgtggc ctacgttgac     540
gtggtatcaa aggaagtcac ccgtgtaatt gatactgggg ttttccccgt accggcggaa     600
catgggaact acacagatcc cgagttgaca ggtcctcttc gcacgacaca gaagcctatc     660
agcattacac agcccgaagg tccttcattt acggtgacgg gcggcaacca tatcgagtgg     720
gagaaatggt ccctggacgt cggattcgac gttcgtgagg gtgtggtgct tcataacatt     780
gcttttcgtg acgagatcg  ccttcgcccg attatcaacc gcgcgtccat tgctgaaatg     840
gtcgtccctt acggggatcc ttctcccatt cgctcgtggc agaactattt cgatacgggg     900
gagtacttag tcgccagta  cgccaactca ttggaacttg gctgtgattg tcttggagat     960
atcacgtacc tgtcc                                                     975
```

<210> SEQ ID NO 13
<211> LENGTH: 957
<212> TYPE: DNA
<213> ORGANISM: Arthrobacter globiformis

<400> SEQUENCE: 13

```
atcacgtacc tgtcccctgt tatctcagat gcgttcggaa accctcgtga atccgcaac      60
gggatctgta tgcatgaaga agattggggg attcttgcaa acattcgga tttatggtcc    120
ggcatcaact atacgcgtcg caatcgtcgt atggtgattt catttttcac aaccatcggg    180
aattatgatt atgggttta ttggtatctg tacctggacg gaacgatcga gtttgaagca    240
aaggcaactg gagtggtatt cacgtctgcg tttcccgagg gcgggtccga taatattagc    300
cagcttgccc caggccttgg cgctccgttt catcaacaca tcttctcggc ccgtttagac    360
atggctatcg atggattcac gaatcgtgtt gaggaagagg atgttgtgcg ccaaacgatg    420
ggacccggca cgaacgtgg gaatgcgttc agtcgtaaac gtacggttct gacgcgcgaa    480
tcagaagcgg tacgtgaggc agacgcacgt acaggtcgca cctggatcat ctcaaatccc    540
gagtctaaga tcgtcttaa tgaacccgta gggtataagt tacacgccca caaccaaccg    600
accttactgg cggaccctgg aagctcaatc gctcgtcgcg cggccttcgc caccaaagat    660
ctgtgggtaa cacgttacgc cgacgatgag cgctatccca caggagactt cgtaaaccag    720
cattccgggg gcgcgggttt gccatcctat attgcccagg accgcgacat cgatggccaa    780
gacatcgtag tatggcatac atttggactt acccactttc cacgtgtgga ggactggcca    840
attatgccgg tggacactgt aggttttcaag cttcgcccag aaggattctt tgaccgcagt    900
cctgtgctgg atgtaccagc caatccctcc caatctggtt cacactgcca tggataa     957
```

<210> SEQ ID NO 14
<211> LENGTH: 15
<212> TYPE: DNA
<213> ORGANISM: Artificial Sequence
<220> FEATURE:
<223> OTHER INFORMATION: pKK223-3

<400> SEQUENCE: 14

```
aagcttggct gtttt                                                     15
```

<210> SEQ ID NO 15
<211> LENGTH: 676
<212> TYPE: PRT
<213> ORGANISM: Lichtheimia corymbifera

<400> SEQUENCE: 15

```
Met Ser Ser Ser Ser Ala Thr Pro Lys Pro His Pro Leu Asp Pro
1               5                   10                  15

Leu Ser Ala Asp Glu Ile Arg Arg Ala Ala Ile Ile Arg Glu Lys
                20                  25                  30

Arg Gly Gln Asp Thr Ser Tyr Val Phe Asn Ser Leu Thr Leu Lys Glu
                35                  40                  45

Pro Ala Lys Gln Gln Met Met Leu Tyr Leu Gly Trp Val Asn Ser Ser
        50                  55                  60

Ser Gln Pro Lys Pro Val Thr Ile Asp Arg Glu Val Phe Ala Val Leu
65                  70                  75                  80

Ile Asp Arg Pro Ser Gly Leu Val His Glu Met Thr Val Asn Leu Asp
                85                  90                  95

Lys Ser Ala Val Thr Ser Trp Asn Lys Val Glu Gly Arg Gln Pro Thr
```

-continued

```
                100                 105                 110
Ile Asn Ile Phe Glu Met Leu Glu Ala Glu Arg Glu Ile Leu Lys Asp
            115                 120                 125

Glu Arg Val Lys Asp Gln Cys Arg Gln Leu Gly Ile Thr Asp Met Ser
130                 135                 140

Met Val Tyr Ala Asp Pro Trp Gly Val Gly Tyr His Glu Ile Lys Gly
145                 150                 155                 160

Lys Arg Leu Val Gln Ala Leu Leu Tyr Ala Arg Thr Ser Pro Asp Asp
                165                 170                 175

Asn Gln Tyr Ala His Pro Leu Asp Phe Asn Pro Leu Tyr Asp Leu Asn
            180                 185                 190

Ala Lys Lys Val Leu Asp Ile Val Ser Lys Arg Arg Asn Ser Ser
        195                 200                 205

Phe Glu Arg Pro Val Ile Pro Met Ala Asn His His Phe Leu Pro Glu
210                 215                 220

His Leu Gly Glu Asp Arg Leu Arg Lys Asp Ile Lys Pro Ile Glu Ile
225                 230                 235                 240

Thr Gln Pro Gln Gly Val Ser Phe Ser Ile Arg Asp Gly His Gln Leu
                245                 250                 255

His Trp Gln Lys Trp Asp Met His Leu Ser Phe Asn Tyr Arg Glu Gly
            260                 265                 270

Leu Val Ile Asn Asn Leu Ser Tyr Arg Asp Met Asp Ser Thr Val Arg
        275                 280                 285

Pro Ile Ile Tyr Arg Met Ser Leu Ala Glu Met Val Val Pro Tyr Ala
    290                 295                 300

Asn Pro Tyr Lys Pro Tyr Asn His Lys Met Ala Phe Asp Val Gly Glu
305                 310                 315                 320

Tyr Gly Leu Gly Asn Leu Thr Asn Ser Leu Glu Leu Gly Cys Asp Cys
                325                 330                 335

Val Gly Lys Ile Gly Tyr Leu Asp Ala Val Leu Ser Asp Leu Asn Gly
            340                 345                 350

Asp Pro Trp His Ile Pro Asn Ala Ile Cys Ile His Glu Glu Asp Thr
        355                 360                 365

Gly Leu Leu Phe Lys His Ser Asp Tyr Arg Thr Gly Lys Ala His Ser
    370                 375                 380

Ala Arg Ser Arg Arg Leu Val Ile Ser His Ile Val Thr Ala Ala Asn
385                 390                 395                 400

Tyr Asp Tyr Gly Leu Tyr Tyr Tyr Phe Tyr Gln Asp Gly Thr Ile Gln
                405                 410                 415

Tyr Glu Val Lys Ala Thr Gly Glu Leu Asn Thr Gln Val Leu Ala Glu
            420                 425                 430

Asp Glu Asp Ala Ala Pro Tyr Gly Thr Ile Val Ala Pro Gln Val Asp
        435                 440                 445

Ala Gln His His Gln His Leu Phe Ser Met Arg Ile Asp Pro Met Leu
    450                 455                 460

Asp Gly Pro Asn Asn Ser Val Ala Glu Val Asp Val Ala Ser Asp
465                 470                 475                 480

Leu Pro Val Gly His Pro His Asn Ser Val Gly Asn Ser Phe Tyr Pro
                485                 490                 495

Val Thr Lys Val Phe Asn Thr Thr Asp Glu Ala Lys Thr Met Ala Ser
            500                 505                 510

Val Glu Arg His Arg Thr Trp Lys Ile Ile Asn Glu Ser Lys Ile His
        515                 520                 525
```

```
Pro Tyr Ala Lys Gln Pro Val Gly Phe Lys Met Met Ala His Pro Thr
        530                 535                 540

Pro Pro Leu Leu Pro Lys Pro Gly Ser Ile Val Tyr Glu Arg Ala Met
545                 550                 555                 560

Phe Ala Ser Lys Thr Leu Trp Val Thr Pro His Asn Asp Lys Gln Leu
                565                 570                 575

Tyr Pro Gly Gly Phe Tyr Cys Tyr Gln Ser Glu Pro Ser Glu Asn Leu
            580                 585                 590

Gly Leu Pro Gln Trp Thr Lys Glu Thr Gln Asn Val Arg Asp Thr Asp
        595                 600                 605

Ile Val Cys Trp Leu Asn Phe Gly Ile Thr His Ile Pro Arg Val Glu
    610                 615                 620

Asp Phe Pro Ile Met Pro Ile Glu Thr Cys Gly Ile Met Leu Lys Pro
625                 630                 635                 640

Ala Asn Phe Phe Leu Cys Asn Pro Gly Ile Asp Ile Pro Pro Ser Thr
                645                 650                 655

Arg Gln Ser Thr Lys Ser Ala Tyr Ala Asn Asp Ala Thr Cys Cys Arg
            660                 665                 670

Lys Asn Asn Leu
        675

<210> SEQ ID NO 16
<211> LENGTH: 2031
<212> TYPE: DNA
<213> ORGANISM: Lichtheimia corymbifera

<400> SEQUENCE: 16
atgtcctctt cctcaagcgc cacgccaaag cctcatccat tagacccttt gtccgcagat      60
gagatccgcc gcgcagcagc cattatccgc gaaaaacgtg gcaggatac ttcttatgtg     120 ttcaacagtt taactttgaa ggaacctgcg aaacagcaaa tgatgttgta cttgggttgg     180
gtcaacagtt catcgcagcc taagcccgtt acaattgacc gcgaagtttt cgcagttctt     240
attgatcgtc caagcggtct ggttcacgag atgacagtta acttagataa gtcggcggtt     300
acctcctgga ataaagtgga aggacgccag cccaccatta acatctttga atgttagag      360 gcggaacgcg aaatcctgaa ggatgagcgt gtcaaggacc aatgtcgcca gctgggcatc     420
accgacatgt caatggtcta tgctgacccg tgggggtag ctatcatga atcaaaggt       480 aaacgtcttg ttcaagcgtt gttatacgca cgcacgtccc ctgacgacaa tcaatacgcg     540
cacccccttg acttcaatcc cttatacgat ctgaacgcta agaaggtgct tgacatcgtc     600
gtgtccaaac gtcgtaattc ctcatttgag cgccctgtga tccccatggc gaatcatcac     660
tttctgcccg aacaccttgg tgaagaccgt cttcgtaagg atattaagcc aatcgaaatt     720
acacaaccgc agggcgtatc gtttccatt cgtgacggtc atcagcttca ttggcagaag     780
tgggacatgc atttgtcatt caactaccgc gaaggccttg ttatcaataa tcttagctac     840
cgtgatatgg actccaccgt ccgtccaatt atttaccgta tgagccttgc tgagatggtc     900
gtgccgtatg ctaaccccta caaaccgtac aatcataaga tggcgttcga cgtaggagag     960
tacggcttag gaatttaac gaatagcctt gagttaggtt gtgactgtgt tggtaagatt    1020
ggttatttag atgcggtgtt gtcggattta aacgggatc cctggcatat ccctaatgca    1080
atttgcattc atgaggagga tacggggttg ttatttaaac actcggacta ccgcacaggg    1140
aaggcgcact ctgctcgtag ccgtcgtttg gtaatttcac atatcgtgac ggcggccaac    1200
```

| | |
|---|---|
| tatgattatg gactgtacta ctacttctac caggatggta ccatccagta cgaagttaag | 1260 |
| gcaacgggtg aattgaacac ccaggtactg gccgaggatg aagacgccgc accctacggc | 1320 |
| accattgtgg ctcctcaagt cgatgcccag catcatcaac atttgttctc catgcgtatc | 1380 |
| gacccaatgt tagacggacc gaacaactcg gtcgcagagg ttgacgtggt tgcctccgat | 1440 |
| cttcccgtcg gacaccctca caattctgtg ggaaacagct tttatccagt aactaaagtc | 1500 |
| ttcaacacta ccgacgaggc caaaacaatg gcgtcagttg agcgtcaccg tacatggaaa | 1560 |
| atcattaacg aaagtaaaat ccatccctat gccaagcagc cggttggttt taagatgatg | 1620 |
| gctcatccca ccccgccgct tctgcctaag ccagggagca tcgtatatga acgcgcaatg | 1680 |
| tttgctagta agacgttatg ggtgacgcct cataacgaca agcagttata tcctggcggt | 1740 |
| ttttattgct atcagtcaga gccgtcagaa aaccttgggc ttccacaatg gacgaaggag | 1800 |
| acacaaaatg tgcgcgatac cgatatcgtc tgttggctga actttggcat cactcatatc | 1860 |
| ccacgcgtag aagactttcc tatcatgcct attgaaactt gtggaattat gcttaagccg | 1920 |
| gcgaacttct tcttatgtaa tcccgggatc gatattccgc cctccacacg tcaatcgacc | 1980 |
| aagagcgcct atgcgaatga tgcaacttgt tgtcgtaaaa acaatttata a | 2031 |

<210> SEQ ID NO 17
<211> LENGTH: 681
<212> TYPE: DNA
<213> ORGANISM: Lichtheimia corymbifera

<400> SEQUENCE: 17

| | |
|---|---|
| atgtcctctt cctcaagcgc cacgccaaag cctcatccat tagacccttt gtccgcagat | 60 |
| gagatccgcc gcgcagcagc cattatccgc gaaaaacgtg gcaggatac ttcttatgtg | 120 |
| ttcaacagtt taactttgaa ggaacctgcg aaacagcaaa tgatgttgta cttgggttgg | 180 |
| gtcaacagtt catcgcagcc taagcccgtt acaattgacc gcgaagtttt cgcagttctt | 240 |
| attgatcgtc caagcggtct ggttcacgag atgacagtta acttagataa gtcggcggtt | 300 |
| acctcctgga ataaagtgga aggacgccag cccaccatta acatctttga atgttagag | 360 |
| gcggaacgcg aaatcctgaa ggatgagcgt gtcaaggacc aatgtcgcca gctgggcatc | 420 |
| accgacatgt caatggtcta tgctgacccg tgggggtag gctatcatga gatcaaaggt | 480 |
| aaacgtcttg ttcaagcgtt gttatacgca cgcacgtccc ctgacgacaa tcaatacgcg | 540 |
| cacccccttg acttcaatcc cttatacgat ctgaacgcta agaaggtgct tgacatcgtc | 600 |
| gtgtccaaac gtcgtaattc ctcatttgag cgccctgtga tccccatggc gaatcatcac | 660 |
| tttctgcccg aacaccttgg t | 681 |

<210> SEQ ID NO 18
<211> LENGTH: 696
<212> TYPE: DNA
<213> ORGANISM: Lichtheimia corymbifera

<400> SEQUENCE: 18

| | |
|---|---|
| cccgaacacc ttggtgaaga ccgtcttcgt aaggatatta agccaatcga aattacacaa | 60 |
| ccgcagggcg tatcgttttc cattcgtgac ggtcatcagc ttcattggca gaagtgggac | 120 |
| atgcatttgt cattcaacta ccgcgaaggc cttgttatca ataatcttag ctaccgtgat | 180 |
| atggactcca ccgtccgtcc aattatttac cgtatgagcc ttgctgagat ggtcgtgccg | 240 |
| tatgctaacc cctacaaacc gtacaatcat aagatggcgt cgacgtagg agagtacggc | 300 |
| ttagggaatt taacgaatag ccttgagtta ggttgtgact gtgttggtaa gattggttat | 360 |

```
ttagatgcgg tgttgtcgga tttaaacggg gatccctggc atatccctaa tgcaatttgc    420
attcatgagg aggatacggg gttgttattt aaacactcgg actaccgcac agggaaggcg    480
cactctgctc gtagccgtcg tttggtaatt tcacatatcg tgacggcggc caactatgat    540 tatgactgt actactactt ctaccaggat ggtaccatcc agtacgaagt taaggcaacg    600
ggtgaattga acacccaggt actggccgag gatgaagacg ccgcacccta cggcaccatt    660
gtggctcctc aagtcgatgc ccagcatcat caacat                              696

<210> SEQ ID NO 19
<211> LENGTH: 684
<212> TYPE: DNA
<213> ORGANISM: Lichtheimia corymbifera

<400> SEQUENCE: 19
cagcatcatc aacatttgtt ctccatgcgt atcgacccaa tgttagacgg accgaacaac     60
tcggtcgcag aggttgacgt ggttgcctcc gatcttcccg tcggacaccc tcacaattct    120
gtgggaaaca gcttttatcc agtaactaaa gtcttcaaca ctaccgacga ggccaaaaca    180
atggcgtcag ttgagcgtca ccgtacatgg aaaatcatta acgaaagtaa aatccatccc    240
tatgccaagc agccggttgg ttttaagatg atggctcatc ccaccccgcc gcttctgcct    300
aagccaggga gcatcgtata tgaacgcgca atgtttgcta gtaagacgtt atgggtgacg    360
cctcataacg acaagcagtt atatcctggc ggtttttatt gctatcagtc agagccgtca    420
gaaaaccttg gcttccaca atggacgaag gagacacaaa atgtgcgcga taccgatatc    480
gtctgttggc tgaactttgg catcactcat atcccacgcg tagaagactt tcctatcatg    540
cctattgaaa cttgtggaat tatgcttaag ccggcgaact tcttcttatg taatcccggg    600
atcgatattc cgccctccac acgtcaatcg accaagagcg cctatgcgaa tgatgcaact    660
tgttgtcgta aaaacaattt ataa                                           684

<210> SEQ ID NO 20
<211> LENGTH: 673
<212> TYPE: PRT
<213> ORGANISM: Lichtheimia ramosa

<400> SEQUENCE: 20

Met Ser Ser Pro Ile Lys Pro Tyr Pro Leu Asp Pro Leu Thr Ala
1               5                  10                  15

Asp Glu Ile Arg Arg Ala Ala Ala Leu Ile Arg Glu Thr Arg Gly Gln
            20                  25                  30

Asp Thr Thr Tyr Val Phe Asn Ser Leu Thr Leu Lys Glu Pro Ser Lys
        35                  40                  45

Gln Gln Met Met Ser Tyr Leu Gly Trp Thr Asn Ser Pro Ser His Pro
    50                  55                  60

Lys Pro Val Thr Ile Asp Arg Glu Val Phe Ala Val Leu Ile Asp Arg
65                  70                  75                  80

Pro Ser Gly Leu Val His Glu Met Thr Val Asn Leu Asp Lys Asn Gln
                85                  90                  95

Val Thr Arg Trp Asn Lys Val Glu Gly Arg Gln Pro Thr Val Asn Val
            100                 105                 110

Phe Glu Met Leu Glu Ala Glu Arg Glu Ile Leu Lys Asp Glu Arg Val
        115                 120                 125

Lys Glu Gln Cys Arg Gln Leu Gly Ile Asn Asp Met Ser Met Val Phe
    130                 135                 140
```

-continued

```
Ala Asp Pro Trp Gly Val Gly Tyr His Glu Ile Lys Gly Lys Arg Leu
145                 150                 155                 160

Val Gln Ala Leu Met Tyr Ala Arg Thr Ser Pro Asp Asn Gln Tyr
            165                 170                 175

Ala His Pro Leu Asp Phe Asn Pro Leu Tyr Asp Val Asn Ala Lys Lys
            180                 185                 190

Val Ile Asp Ile Ile Val Ser Lys Arg Arg Asn Ser Ser Phe Asp Arg
            195                 200                 205

Pro Val Ile Pro Met Ala Asn His His Phe Leu Pro Glu His Leu Gly
            210                 215                 220

Gln Asp Arg Leu Arg Lys Asp Ile Lys Pro Ile Glu Ile Thr Gln Pro
225                 230                 235                 240

Gln Gly Val Ser Phe Ser Ile Arg Asp Gly His Gln Leu His Trp Gln
                245                 250                 255

Lys Trp Asp Met His Leu Ser Phe Asn Tyr Arg Glu Gly Leu Val Ile
            260                 265                 270

Asn Asn Leu Ser Tyr Arg Asp Met Asp Gly Thr Val Arg Pro Ile Ile
            275                 280                 285

Tyr Arg Met Ser Leu Ser Glu Met Val Val Pro Tyr Ala Asn Pro Tyr
290                 295                 300

Lys Pro Tyr Asn His Lys Met Ala Phe Asp Val Gly Glu Tyr Gly Leu
305                 310                 315                 320

Gly Asn Leu Thr Asn Ser Leu Glu Leu Gly Cys Asp Cys Val Gly Lys
                325                 330                 335

Ile Cys Tyr Leu Asp Ala Thr Leu Ser Asp Leu Asn Gly Asp Pro Trp
            340                 345                 350

Gln Ile Pro Asn Ala Ile Cys Ile His Glu Glu Asp Thr Gly Leu Leu
            355                 360                 365

Phe Lys His Thr Asp Tyr Arg Thr Gly Lys Ala His Ser Ala Arg Ser
370                 375                 380

Arg Arg Leu Val Ile Ser His Ile Val Thr Ala Ala Asn Tyr Asp Tyr
385                 390                 395                 400

Gly Leu Tyr Tyr Tyr Phe Tyr Gln Asp Gly Thr Ile Gln Tyr Glu Val
                405                 410                 415

Lys Ala Thr Gly Glu Leu Asn Thr Gln Val Leu Ala Ala Asp Glu Asp
            420                 425                 430

Ala Ala Pro Tyr Gly Thr Ile Val Ala Pro Gln Val Asp Ala Gln His
            435                 440                 445

His Gln His Leu Phe Ser Met Arg Ile Asp Pro Met Val Asp Gly Pro
            450                 455                 460

Asn Asn Ser Val Ala Glu Val Asp Val Val Ala Ser Asp Leu Pro Val
465                 470                 475                 480

Gly His Pro His Asn Ser Ile Gly Asn Ser Phe Tyr Pro Val Thr Lys
                485                 490                 495

Val Phe Asn Thr Thr Asp Glu Ala Lys Thr Met Ala Ser Ile Glu Arg
            500                 505                 510

His Arg Ser Trp Lys Ile Ile Asn Glu Asn Lys Ile His Pro Tyr Ala
            515                 520                 525

Lys Gln Pro Val Gly Phe Lys Met Met Ala His Pro Thr Pro Pro Leu
            530                 535                 540

Leu Pro Lys Pro Gly Ser Ile Val Tyr Glu Arg Ala Met Phe Ala Ser
545                 550                 555                 560
```

Lys Thr Leu Trp Val Thr Pro Tyr Asn Glu Glu Gln Arg Tyr Pro Gly
                565                 570                 575

Gly Phe Tyr Cys Tyr Gln Ser Glu Pro Ser Glu Asn Leu Gly Leu Pro
            580                 585                 590

Gln Trp Thr Lys Glu Thr Gln Asn Val Arg Asp Thr Asp Ile Val Cys
        595                 600                 605

Trp Leu Asn Phe Gly Ile Thr His Ile Pro Arg Val Glu Asp Phe Pro
    610                 615                 620

Ile Met Pro Ile Glu Thr Cys Gly Val Met Leu Lys Pro Val Asn Phe
625                 630                 635                 640

Phe Leu Gly Asn Pro Gly Ile Asp Ile Pro Pro Ser Thr Arg Gln Ser
                645                 650                 655

Thr Lys Ser Ala Tyr Ala Thr Glu Ala Thr Cys Cys Arg Lys Asn Asn
            660                 665                 670

Leu

<210> SEQ ID NO 21
<211> LENGTH: 2022
<212> TYPE: DNA
<213> ORGANISM: Lichtheimia ramosa

<400> SEQUENCE: 21

```
atgtcgtcct caccgatcaa gccgtatcct ttagatccat taacagccga tgagattcgc      60
cgcgcagcag cccttatccg tgaaacgcgc gggcaggaca ccacctatgt gttcaactct     120
ctgacactga aggaaccttc gaagcagcaa atgatgtctt accttgggtg gactaactcg     180
cctagtcacc ccaagccggt cactattgac cgcgaagtct ttgcggtgtt aatcgaccgt     240
ccatccgggt tggtccatga aatgaccgtg aacttggata aaaccaggt gacccgctgg     300
aataaggttg aaggtcgcca acctacgtta aatgtattcg agatgttgga ggcggaacgc     360
gagattttga agacgagcg tgttaaagag caatgccgcc aattggggat taatgatatg     420
agtatggtct ttgccgatcc ctgggggtgta ggatatcacg aaattaaagg caaacgtttg     480
gttcaggcct tgatgtatgc acgtacctct ccggatgaca accaatacgc tcatccactg     540
gactttaacc ctctgtacga tgtgaacgcc aagaaagtaa tcgacattat cgtgtcaaaa     600
cgtcgcaaca gtagtttcga tcgtccagtc attcccatgg caaatcatca tttcttgccg     660
gagcatttag ggcaagatcg ccttcgcaaa gacatcaagc ctattgagat cactcaacct     720
caggggttt ctttcagcat ccgcgatgga caccaattac attggcagaa gtgggacatg     780
catttgtcat ttaattaccg tgaaggactt gtgatcaaca acttgagcta tcgcgacatg     840
gatggcactg tccgccccat tatttatcgt atgtcgcttt ccgagatggt tgtgccctat     900
gcgaatccat ataagccgta taaccacaaa atggccttcg acgttggtga gtacgggctt     960
ggtaacctta caaactctct tgaattaggg tgtgactgcg tcggaaagat tgctatttta    1020
gacgcgacat tgtcggattt gaatggagac ccgtggcaga ttcccaatgc aatctgcatc    1080
catgaagaag acacaggact tctgtttaag cacacggatt accgcacggg aaaagcacac    1140
tcggcgcgtt ctcgtcgttt ggttatctct catatcgtta cggcggcaaa ttacgactac    1200
ggtttatatt attacttcta tcaagacggt accattcagt atgaagttaa agccaccggc    1260
gagttgaaca ctcaggttct tgcggcagac gaagacgctg ctccttacgg aactattgtg    1320
gccccgcagg ttgacgctca acaccatcaa catttgttca gtatgcgtat cgacccaatg    1380
gtcgatggcc cgaataactc agtggcggaa gtcgacgttg tggcatctga tcttccggtc    1440
```

```
gggcacccgc acaattctat tggtaacagt ttttaccccg taacgaaagt atttaacacg   1500
actgatgagg caaaaacgat ggcctccatt gaacgccacc gctcatggaa aattattaac   1560
gagaacaaaa ttcatcccta tgcaaagcag cccgtaggtt tcaaaatgat ggcccaccct   1620
acgccgcctc ttctgcccaa accaggttct atcgtctacg aacgcgccat gtttgcgagc   1680
aaaacattgt gggttactcc atacaacgag gagcaacgtt atcccggggg gttttattgt   1740
taccagtcgg aaccttcgga gaacttagga ctgccacagt ggacaaagga aactcagaat   1800
gttcgcgata cggatattgt atgttggttg aattttggca tcacccacat ccctcgcgtt   1860
gaggatttcc caatcatgcc tatcgaaacg tgcggcgtaa tgctgaagcc ggtaaatttt   1920
tttttaggga atcccggcat tgacatcccg ccctccactc gccaaagcac gaagagtgcg   1980
tacgcgacgg aagcgacttg ctgccgcaaa ataatttat aa                       2022

<210> SEQ ID NO 22
<211> LENGTH: 678
<212> TYPE: DNA
<213> ORGANISM: Lichtheimia ramosa

<400> SEQUENCE: 22
atgtcgtcct caccgatcaa gccgtatcct ttagatccat taacagccga tgagattcgc     60
cgcgcagcag cccttatccg tgaaacgcgc gggcaggaca ccacctatgt gttcaactct    120
ctgacactga aggaaccttc gaagcagcaa atgatgtctt accttgggtg gactaactcg    180
cctagtcacc ccaagccggt cactattgac cgcgaagtct ttgcggtgtt aatcgaccgt    240
ccatccgggt tggtccatga aatgaccgtg aacttggata aaaaccaggt gacccgctgg    300
aataaggttg aaggtcgcca acctacggta aatgtattcg agatgttgga ggcggaacgc    360
gagattttga agacgagcg tgttaaagag caatgccgcc aattggggat taatgatatg    420
agtatggtct ttgccgatcc ctggggtgta ggatatcacg aaattaaagg caaacgtttg    480
gttcaggcct tgatgtatgc acgtacctct ccggatgaca accaatacgc tcatccactg    540
gactttaacc ctctgtacga tgtgaacgcc aagaaagtaa tcgacattat cgtgtcaaaa    600
cgtcgcaaca gtagtttcga tcgtccagtc attcccatgg caaatcatca tttcttgccg    660
gagcatttag ggcaagat                                                 678

<210> SEQ ID NO 23
<211> LENGTH: 693
<212> TYPE: DNA
<213> ORGANISM: Lichtheimia ramosa

<400> SEQUENCE: 23
catttagggc aagatcgcct tcgcaaagac atcaagccta ttgagatcac tcaacctcag     60
ggggtttctt tcagcatccg cgatggacac caattacatt ggcagaagtg ggacatgcat    120 ttgtcatttta ttaccgtga aggacttgtg atcaacaact tgagctatcg cgacatggat    180
ggcactgtcc gccccattat ttatcgtatg tcgctttccg agatggttgt gccctatgcg    240
aatccatata agccgtataa ccacaaaatg gccttcgacg ttggtgagta cgggcttggt    300
aaccttacaa actctcttga attagggtgt gactgcgtcg gaaagatttg ctatttagac    360
gcgacattgt cggatttgaa tggagacccg tggcagattc ccaatgcaat ctgcatccat    420
gaagaagaca caggacttct gtttaagcac acggattacc gcagggaaa agcacactcg    480 gcgcgttctc gtcgtttggt tatctctcat atcgttacgg cggcaaatta cgactacggt    540
ttatattatt acttctatca agacggtacc attcagtatg aagttaaagc caccggcgag    600
```

```
ttgaacactc aggttcttgc ggcagacgaa gacgctgctc cttacggaac tattgtggcc    660
ccgcaggttg acgctcaaca ccatcaacat ttg                                 693

<210> SEQ ID NO 24
<211> LENGTH: 681
<212> TYPE: DNA
<213> ORGANISM: Lichtheimia ramosa

<400> SEQUENCE: 24
caccatcaac atttgttcag tatgcgtatc gacccaatgg tcgatggccc gaataactca     60
gtggcggaag tcgacgttgt ggcatctgat cttccggtcg ggcacccgca caattctatt    120
ggtaacagtt tttaccccgt aacgaaagta tttaacacga ctgatgaggc aaaaacgatg    180
gcctccattg aacgccaccg ctcatggaaa attattaacg agaacaaaat tcatccctat    240
gcaaagcagc ccgtaggttt caaaatgatg gcccacccta cgccgcctct tctgcccaaa    300
ccaggttcta tcgtctacga acgcgccatg tttgcgagca aaacattgtg ggttactcca    360
tacaacgagg agcaacgtta tcccgggggg ttttattgtt accagtcgga accttcggag    420
aacttaggac tgccacagtg gacaaaggaa actcagaatg ttcgcgatac ggatattgta    480
tgttggttga atttttggcat cacccacatc cctcgcgttg aggatttccc aatcatgcct    540
atcgaaacgt gcggcgtaat gctgaagccg gtaaatttttt ttttagggaa tcccggcatt    600
gacatcccgc cctccactcg ccaaagcacg aagagtgcgt acgcgacgga agcgacttgc    660
tgccgcaaaa ataatttata a                                              681

<210> SEQ ID NO 25
<211> LENGTH: 668
<212> TYPE: PRT
<213> ORGANISM: Syncephalastrum racemosum

<400> SEQUENCE: 25

Met Thr Ile Val Ser Pro Ser His Pro Leu Asp Pro Leu Thr Pro Ser
1               5                   10                  15

Glu Ile Arg His Val Ala Glu Ile Val Arg Ala Thr Arg Ser Pro Asp
            20                  25                  30

Asp Lys Thr Pro Arg Asp Tyr Ile Phe Ser Ser Ile Cys Leu Lys Glu
        35                  40                  45

Pro His Lys Asp Lys Thr Leu Ala Tyr Leu Gln Ser Val Ser Glu Glu
    50                  55                  60

Ala Ala Ala Leu Met Pro Glu Arg Glu Ala Leu Val Ile Leu Ile Asp
65                  70                  75                  80

Arg Pro Ser Gly Leu Val His Glu Ile Leu Val Ser Ile Thr Asp Glu
                85                  90                  95

Lys Val Lys Ser Ala Lys Thr Leu Lys Asn Val Gln Pro Thr Gln His
            100                 105                 110

Val Leu Glu Met Ile Glu Ala Glu Lys Ile Ile Thr Lys Asp Pro Ser
        115                 120                 125

Val Ile Glu Glu Cys Arg Lys Leu Gly Ile Thr Asp Met Lys Asn Val
    130                 135                 140

Tyr Ala Asp Pro Trp Thr Val Gly Tyr His Ala Gln Phe Lys Ser Ser
145                 150                 155                 160

Lys Arg Leu Met Gln Ala Leu Met Tyr Met Arg Thr Ser Pro Asp Asp
                165                 170                 175

Asn Gln Tyr Ala His Pro Leu Asp Phe Val Pro Ile Tyr Asp Val Asn
```

```
                180                 185                 190
Ala Gln Lys Val Val Glu Ile Leu Arg Gln Glu Thr Ser Glu Ala Ser
            195                 200                 205

Lys Tyr Asp Arg Pro Thr Val Pro Leu Glu Asn His Gln Phe Leu Pro
        210                 215                 220

Glu His Ile Gly Val Glu Asn Leu Arg Lys Asp Ile Lys Pro Ile Glu
225                 230                 235                 240

Ile Thr Gln Pro Glu Gly Val Ser Phe Thr Val Arg Gly Arg Glu Ile
                245                 250                 255

Glu Trp Gln Asn Trp Ser Met His Val Gly Phe Asn Tyr Arg Glu Gly
            260                 265                 270

Val Ile Ile Asn Asn Val Ser Tyr Lys Asp Lys Gly Asn Val Arg Pro
        275                 280                 285

Leu Phe Tyr Arg Val Ser Val Ser Glu Met Val Val Pro Tyr Ala His
        290                 295                 300

Pro Lys Glu Pro Phe Asn His Lys Met Ala Phe Asp Val Gly Glu Tyr
305                 310                 315                 320

Gly Leu Gly Asn Leu Thr Asn Ser Leu Glu Leu Gly Cys Asp Cys Leu
                325                 330                 335

Gly Ser Ile Tyr Tyr Met Asp Gly Val Cys Asn Asn Leu Asp Gly Glu
            340                 345                 350

Pro Trp Val Ile Pro Asn Ala Ile Cys Ile His Glu Glu Asp Thr Gly
        355                 360                 365

Leu Leu Phe Lys His Thr Asp Tyr Arg Thr Asp Lys Ala His Ser Ala
        370                 375                 380

Arg Ser Arg Arg Leu Val Ile Ser Gln Ile Val Thr Ala Ala Asn Tyr
385                 390                 395                 400

Asp Tyr Gly Leu Tyr Phe Tyr Phe Tyr Gln Asp Gly Thr Phe Gln Tyr
                405                 410                 415

Glu Val Lys Ala Thr Gly Glu Leu Asn Thr Gln Val Phe Ala Glu Asp
            420                 425                 430

Glu Asn Pro Ala Pro Tyr Gly Thr Ala Val Ala Pro Gln Val Val Gly
        435                 440                 445

Gln His His Gln His Leu Phe Met Met Arg Ile Asp Pro Met Leu Asp
        450                 455                 460

Gly Arg Leu Asn Ser Val Ala Gln Val Asp Val Leu Pro Ser Glu Tyr
465                 470                 475                 480

Pro Val Gly His Val Glu Asn Pro Ile Gly Asn Ala Phe Ser Pro Ile
                485                 490                 495

Thr Thr Ile Tyr Ser Asp Thr Thr Glu Ala Gln Ala His Gly Asn Leu
            500                 505                 510

Glu Ser Ser Arg Thr Trp Lys Ile Ile Asn Glu Ser Lys Leu His Pro
        515                 520                 525

Tyr Thr Lys Glu Pro Val Gly Tyr Lys Leu Val Ser Pro Asn Thr Pro
        530                 535                 540

Pro Met Leu Pro Lys Pro Gly Ser Leu Val Tyr Glu Arg Ala Lys Phe
545                 550                 555                 560

Ala Thr Lys Thr Ile Trp Val Thr Pro Tyr Asp Pro Asp Gln Ile Tyr
                565                 570                 575

Pro Ala Gly Phe Tyr Cys Ser Gln Ser Pro Gly Asp Asp Ser Met Gly
            580                 585                 590

Leu Pro Ala Trp Thr Lys Glu Pro Gln Ser Val Arg Gly Arg Asp Val
        595                 600                 605
```

```
Val Val Trp Leu Thr Phe Gly Leu Thr His Ile Pro Arg Val Glu Asp
    610                 615                 620

Phe Pro Val Met Pro Val Glu Thr Cys Gly Trp Ala Leu Lys Ala Cys
625                 630                 635                 640

Asn Phe Phe Leu Gly Asn Pro Gly Ile Asp Ile Pro Ala Ala Gln Lys
                645                 650                 655

Gly Thr Ser Lys Arg Val Asn Gly Ala Cys Cys Ala
            660                 665
```

<210> SEQ ID NO 26
<211> LENGTH: 2007
<212> TYPE: DNA
<213> ORGANISM: Syncephalastrum racemosum

<400> SEQUENCE: 26

```
atgaccattg tctctccttc acacccctta gacccgctta cccctagtga aattcgccac    60
gtagccgaaa tcgtacgcgc cactcgctct cctgatgata agaccccgcg cgattatatt   120
ttttccagca tttgcttaaa agaacctcat aaggacaaga cgttggcata cttgcaatcg   180
gtgtccgaag aagctgccgc tctgatgcct gaacgtgaag ctctggtaat tctgatcgat   240
cgcccgtcgg gccttgtaca cgagatttta gtttctatca cagatgagaa ggtgaaatct   300
gcaaagaccc ttaagaatgt tcaacctact cagcatgtct tagagatgat cgaagcggaa   360
aagatcatca cgaaggatcc ttcagttatc gaagaatgtc gcaagttagg cattacggat   420
atgaagaatg tctatgctga tccgtggacg gtgggttacc atgctcaatt taagtccagt   480
aaacgtttaa tgcaggccct tatgtacatg cgcacctctc ccgacgacaa ccagtatgcg   540
catcctttag attttgtacc gatttatgat gttaacgcac aaaaggtcgt cgagattttg   600
cgccaggaaa cttcggaagc aagcaagtat gatcgtccga cagttccgtt agaaaaccat   660
cagttttttac cagagcacat tggcgtggaa aacttacgca aggacatcaa gcccatcgaa   720
attacccaac cggagggggt gtcttttaca gtgcgcgggc gtgaaatcga atggcaaaat   780
tggagtatgc atgtcgggtt caactatcgt gaaggagtta tcattaacaa cgtgtccctat  840
aaggacaagg gcaatgtgcg tccgttattc taccgcgtgt cggtaagtga atggtcgta    900
ccgtacgcac accccaagga gccgttcaac ataagatggc ctttgacgt cggggagtac   960
ggtttgggga accttactaa cagccttgag ctgggctgtg attgtttggg ctcgattat   1020
tatatggatg gtgtctgtaa taatctggat ggcgaaccct gggtcatccc caatgcaatt  1080
tgcatccatg aagaggatac gggttgtta ttcaaacaca ccgattaccg cactgataaa  1140
gctcacagcg cacgtagccg ccgtttggtt atctcgcaaa ttgtgaccgc cgccaactat  1200
gattatggct tgtatttcta cttctaccaa gacggtacgt tcagtacga ggtcaaagct   1260
accggggagc tgaacactca gttttttgcg gaagacgaaa cccagcacc ttatggtacc   1320
gcagtcgctc cccaagtcgt aggccagcat catcaacact tatttatgat gcgcattgac  1380
ccaatgttag atggtcgtct gaactctgtt gcccaggttg atgttttacc ctccgagtac  1440
ccagtcggtc acgtcgagaa tccaatcggc aacgcctta gtcctattac gactatttac  1500
agtgacacga ctgaggcgca ggcacatggg aatttagagt cgtcgcgtac atggaagatc  1560
attaacgaat ctaaactgca tccatataca aaagaaccag taggttacaa acttgtgagt  1620
cctaacactc ccccgatgct tcccaaacct ggatccttg tctatgaacg cgcaaaattc  1680
gctactaaaa ccatctgggt aactccctat gaccccgatc agatttatcc cgccggattc  1740
```

```
tattgctcac aatcaccggg tgacgattcg atgggattgc ctgcatggac taaagaacca   1800
caaagcgtac gtggacgtga cgtagttgtg tggcttacct tcggacttac gcacatccca   1860
cgcgtggaag acttccccgt tatgcctgta gagacgtgcg ggtgggcgct gaaagcgtgt   1920
aattttttct tagggaatcc agggatcgac attccggcag cacagaaggg gacctccaag   1980
cgcgtaaatg gtgcatgttg tgcgtaa                                      2007

<210> SEQ ID NO 27
<211> LENGTH: 675
<212> TYPE: DNA
<213> ORGANISM: Syncephalastrum racemosum

<400> SEQUENCE: 27
atgaccattg tctctccttc acaccccttg acccgctta ccctagtga aattcgccac      60 gtagccgaaa tcgtacgcgc cactcgctct cctgatgata agaccccgcg cgattatatt    120
ttttccagca tttgcttaaa agaacctcat aaggacaaga cgttggcata cttgcaatcg    180
gtgtccgaag aagctgccgc tctgatgcct gaacgtgaag ctctggtaat tctgatcgat    240
cgcccgtcgg gccttgtaca cgagatttta gtttctatca cagatgagaa ggtgaaatct    300
gcaaagaccc ttaagaatgt tcaacctact cagcatgtct tagagatgat cgaagcggaa    360
aagatcatca cgaaggatcc ttcagttatc gaagaatgtc gcaagttagg cattacggat    420
atgaagaatg tctatgctga tccgtggacg gtgggttacc atgctcaatt taagtccagt    480
aaacgtttaa tgcaggccct tatgtacatg cgcacctctc ccgacgacaa ccagtatgcg    540
catcctttag attttgtacc gatttatgat gttaacgcac aaaaggtcgt cgagattttg    600
cgccaggaaa cttcggaagc aagcaagtat gatcgtccga cagttccgtt agaaaaccat    660 cagttttttac cagag                                                   675

<210> SEQ ID NO 28
<211> LENGTH: 690
<212> TYPE: DNA
<213> ORGANISM: Syncephalastrum racemosum

<400> SEQUENCE: 28 cagttttttac cagagcacat tggcgtggaa aacttacgca aggacatcaa gcccatcgaa    60
attacccaac cggaggggggt gtcttttaca gtgcgcgggc gtgaaatcga atggcaaaat   120
tggagtatgc atgtcgggtt caactatcgt gaaggagtta tcattaacaa cgtgtcctat   180
aaggacaagg gcaatgtgcg tccgttattc taccgcgtgt cggtaagtga atggtcgta    240 ccgtacgcac accccaagga gccgttcaac cataagatgg cctttgacgt cggggagtac   300
ggtttgggga accttactaa cagccttgag ctgggctgtg attgtttggg ctcgatttat   360
tatatggatg gtgtctgtaa taatctggat ggcgaaccct gggtcatccc caatgcaatt   420
tgcatccatg aagaggatac gggttttgtta ttcaaacaca ccgattaccg cactgataaa   480
gctcacagcg cacgtagccg ccgtttggtt atctcgcaaa ttgtgaccgc cgccaactat   540
gattatggct tgtatttcta cttctaccaa gacggtacgt ttcagtacga ggtcaaagct   600 accgggagc tgaacactca agttttttgcg gaagacgaaa acccagcacc ttatggtacc   660
gcagtcgctc cccaagtcgt aggccagcat                                   690

<210> SEQ ID NO 29
<211> LENGTH: 672
<212> TYPE: DNA
<213> ORGANISM: Syncephalastrum racemosum
```

<400> SEQUENCE: 29

```
gtcgtaggcc agcatcatca acacttattt atgatgcgca ttgacccaat gttagatggt    60
cgtctgaact ctgttgccca ggttgatgtt ttaccctccg agtacccagt cggtcacgtc   120
gagaatccaa tcggcaacgc ctttagtcct attacgacta tttacagtga cacgactgag   180
gcgcaggcac atgggaattt agagtcgtcg cgtacatgga agatcattaa cgaatctaaa   240
ctgcatccat atacaaaaga accagtaggt tacaaacttg tgagtcctaa cactcccccg   300
atgcttccca aacctggatc ccttgtctat gaacgcgcaa aattcgctac taaaaccatc   360
tgggtaactc cctatgaccc cgatcagatt tatcccgccg gattctattg ctcacaatca   420
ccgggtgacg attcgatggg attgcctgca tggactaaag aaccacaaag cgtacgtgga   480
cgtgacgtag ttgtgtggct taccttcgga cttacgcaca tcccacgcgt ggaagacttc   540
cccgttatgc ctgtagagac gtgcgggtgg gcgctgaaag cgtgtaattt tttcttaggg   600
aatccaggga tcgacattcc ggcagcacag aagggaccct ccaagcgcgt aaatggtgca   660
tgttgtgcgt aa                                                       672
```

<210> SEQ ID NO 30
<211> LENGTH: 683
<212> TYPE: PRT
<213> ORGANISM: Syncephalastrum racemosum

<400> SEQUENCE: 30

```
Met Thr Val Ser Ala Val Ile His Pro Leu Asp Pro Leu Ser Pro Glu
1               5                  10                  15

Glu Ile Arg His Ala Ser Ala Ile Ile Arg Arg Glu Arg Ser Ala Asp
            20                  25                  30

Lys Thr Ile Phe Ile Phe Asn Ser Ile Ser Leu Arg Glu Pro Pro Lys
        35                  40                  45

Asp Gln Val Leu Ala His Phe Gly Trp Ala Ala Gly Pro Lys Pro Ala
    50                  55                  60

Gln Ile Asp Arg Gln Ala Phe Val Val Leu Ile Asp Arg Pro Ser Gly
65                  70                  75                  80

Leu Val His Glu Ile Ile Val Ser Leu Thr Thr Ser Ser Val Val Ser
                85                  90                  95

Trp Asn Arg Lys Gln Gly Val Gln Pro Thr Leu His Val Gln Glu Met
            100                 105                 110

Leu Glu Ala Glu Glu Val Met Leu Lys Asp Glu Arg Val Ile Glu Glu
        115                 120                 125

Cys Arg Lys Leu Gly Ile Glu Asp Met Ser Leu Val Phe Ala Asp Thr
    130                 135                 140

Trp Gly Val Gly Trp His Lys Thr Lys Gly Lys Arg Leu Met Gln Ala
145                 150                 155                 160

Leu Met Tyr Met Arg Thr Ser Pro Asp Asn Gln Tyr Ala His Pro
                165                 170                 175

Leu Asp Phe Thr Pro Leu Tyr Asp Val Asn Glu Gln Lys Val Ile Asp
            180                 185                 190

Val Leu Val Ala Lys Arg Arg Asn Ser Lys Phe Glu Arg Pro Val Ile
        195                 200                 205

Pro Arg Ala Asp His Gln Phe Leu Pro Glu His Leu Gly Glu Gly Asn
    210                 215                 220

Leu Arg Lys Asp Ile Lys Pro Ile Glu Ile Gln Pro Glu Gly Val
225                 230                 235                 240
```

-continued

Ser Phe Gln Ile Arg Gly His Glu Ile Asp Trp Gln Lys Trp Asn Leu
                245                 250                 255

His Ile Gly Phe Asn Tyr Arg Glu Gly Leu Val Ile Ser Asn Val Ser
            260                 265                 270

Tyr Lys Asp Met Asp Gly Thr Val Arg Pro Val Phe Tyr Arg Val Ser
        275                 280                 285

Leu Ala Glu Met Val Val Pro Tyr Ala Asn Pro Tyr Glu Pro Tyr Asn
    290                 295                 300

His Lys Met Ala Phe Asp Val Gly Glu Tyr Gly Leu Gly Asn Leu Thr
305                 310                 315                 320

Asn Ser Leu Glu Leu Gly Cys Asp Cys Val Gly Ser Ile Phe Tyr Met
                325                 330                 335

Asp Gly Val Cys Ser Asp Leu Lys Gly Asp Ala Trp Val Ile Pro Asn
            340                 345                 350

Ala Ile Cys Ile His Glu Glu Asp Thr Gly Leu Leu Phe Lys His Thr
        355                 360                 365

Asp Phe Arg Asn Asn Lys Ala His Ser Ala Arg Ser Arg Arg Leu Val
    370                 375                 380

Ile Ser His Ile Val Thr Ala Ala Asn Tyr Asp Tyr Gly Leu Tyr Tyr
385                 390                 395                 400

Tyr Phe Tyr Gln Asp Gly Thr Phe Gln Tyr Glu Val Lys Ala Thr Gly
                405                 410                 415

Glu Leu Asn Thr His Val Leu Ala Glu Asp Glu Asn Pro Ala Pro Tyr
            420                 425                 430

Gly Thr Ile Val Ala Pro Gln Ile Asp Ala Gln His His Gln His Leu
        435                 440                 445

Phe Ser Met Arg Ile Asp Pro Met Val Asp Gly Pro Thr Asn Ser Val
    450                 455                 460

Ala Gln Val Asp Val Val Ala Ser Asp Leu Pro Val Gly His Pro Asp
465                 470                 475                 480

Asn Ala Val Gly Asn Ala Phe Ser Pro Ile Thr Thr Ile Tyr Ala Asn
                485                 490                 495

Thr Asp Glu Ala Gln Ala Arg Ala Asn Gly Glu Thr Ser Arg Tyr Trp
            500                 505                 510

Lys Ile Ile Asn Glu Asp Lys Ile His Pro Tyr Thr Arg Glu Pro Val
        515                 520                 525

Gly Phe Lys Leu Met Cys Pro Asn Thr Pro Pro Met Leu Pro Lys Pro
    530                 535                 540

Gly Ser Ile Ala Tyr Glu Arg Ala Val Phe Ala Ser Lys Thr Val Trp
545                 550                 555                 560

Val Thr Pro Tyr Asp Ala Glu Gln Leu Phe Pro Gly Gly Phe Tyr Cys
                565                 570                 575

Tyr Gln Ser Asp Pro Ala Asp Arg Leu Gly Leu Pro Glu Trp Thr Lys
            580                 585                 590

Gly Lys Lys Asp Val Lys Asn Lys Asp Ile Val Leu Trp Leu Thr Phe
        595                 600                 605

Gly Leu Thr His Ile Pro Arg Val Glu Asp Phe Pro Ile Met Pro Val
    610                 615                 620

Glu Thr Cys Gly Phe Met Leu Lys Pro Cys Asn Phe Phe Leu Ala Asn
625                 630                 635                 640

Pro Gly Ile Asp Ile Pro Ala Ser Asp Lys His Ser Thr Lys Ser Ala
                645                 650                 655

```
                Tyr Ala His Ala Leu Thr Asn Gly Ala Asn Gly Thr Gly Asn Gly Ser
                            660                 665                 670

Thr Asn Gly Ser Ser Cys Cys Asn Lys Asn Tyr
                    675                 680

<210> SEQ ID NO 31
<211> LENGTH: 2052
<212> TYPE: DNA
<213> ORGANISM: Syncephalastrum racemosum

<400> SEQUENCE: 31
atgacagttt ctgccgtgat tcatcctttg gaccccttgt ctcccgagga gatccgtcat         60
gcatcagcga ttatccgccg cgagcgtagt gccgacaaga caatctttat cttcaacagc       120
atctcgctgc gtgaaccccc caaagaccag gtgcttgcac actttggctg gctgctggc        180 ccaaaacctg ctcagattga tcgtcaggct ttcgtcgtcc ttatcgatcg cccgtccggc       240
ttagtgcatg aaattatcgt gtccttaacg acgtccagcg tggtttcatg gaaccgtaaa       300
caaggcgtac aaccaacgct gcacgttcag gagatgcttg aggcagaaga ggtgatgttg       360
aaagatgaac gtgtcatcga ggaatgccgc aaattaggaa tcgaagatat gagtcttgtg       420
tttgccgaca cgtggggagt gggctggcat aaaacaaagg gcaaacgtct tatgcaggct       480
ttgatgtata tgcgtacgag ccctgatgat aaccagtatg cgcatcccct tgactttaca       540
ccattatacg atgtcaatga gcaaaaagtc atcgatgtgc ttgtcgccaa cgccgtaac        600 tcaaagttcg aacgtcccgt catccccccgt gcggaccacc agtttctgcc ggaacacctg       660
ggggagggca atttgcgcaa agatattaag cccattgaaa ttattcaacc agagggtgtc       720
agctttcaaa tccgcgggca tgagatcgac tggcaaaagt ggaaccttca catcggattc       780
aattatcgcg agggacttgt tatcagcaac gttagttaca agacatgga cggcacggta       840 cgtcctgtat tctatcgcgt atctctggca gaaatggtag tccctacgc gaatccttac        900 gaaccctaca accataagat ggccttcgat gtaggagagt acggcctggg caacttgacg       960
aacagtttag aactgggatg tgattgcgta gggagcatct tctacatgga cggggtctgt      1020
tcggatctga agggagacgc gtgggtcatc cccaatgcga tctgcatcca tgaagaggac      1080
accgggttat tgttcaagca cacagatttt cgcaacaaca aagcgcactc agctcgtagt      1140
cgtcgtttgg ttatttccca tatcgttacc gccgccaatt atgattatgg ttgtattac       1200 tatttttacc aggatggtac tttccaatac gaagtcaagg ccacaggaga acttaacact      1260
cacgtcttag cggaggatga gaaccccgct ccctacggaa caattgtggc acctcagatc      1320
gatgcgcaac accaccaaca cttatttttcc atgcgcattg atccgatggt agacggaccg      1380
actaactcgg tggctcaggt agacgtggta gctagcgact tgcctgtcgg acaccctgac      1440
aacgccgtgg ggaatgcatt ctcgccaatt accacaatct atgcgaacac agacgaggca      1500
caagcgcgcg ccaatggaga gacttcccgt tactggaaga tcatcaacga agataaaatt      1560
cacccatata cacgtgaacc tgttggtttt aagcttatgt gtccgaacac accacccatg      1620
ctgccgaaac cgggatccat tgcgtatgag cgtgcagtct tcgcttcgaa acggtctgg       1680 gttaccccgt acgacgcaga acaattgttc ccaggtggtt tctactgtta tcagtcggac      1740
cccgccgatc gtttaggcct gccggagtgg acaaaaggga aaaggacgt aaagaacaag       1800 gacattgtcc tgtggttaac gttcgggctg acccacattc gcgtgtggga agactttccc      1860
attatgcccg tagaaacctg cggctttatg cttaaacccct gtaacttctt ccttgcaaac      1920
ccaggaattg acatcccggc ctccgataag cactcgacta aatcggcgta cgctcatgcg      1980
```

| | |
|---|---|
| cttacgaatg gagccaatgg gactgggaac ggtagcacaa acggctccag ctgctgcaat | 2040 |
| aagaattact aa | 2052 |

<210> SEQ ID NO 32
<211> LENGTH: 687
<212> TYPE: DNA
<213> ORGANISM: Syncephalastrum racemosum

<400> SEQUENCE: 32

| | |
|---|---|
| atgacagttt ctgccgtgat tcatcctttg acccccttgt ctcccgagga gatccgtcat | 60 |
| gcatcagcga ttatccgccg cgagcgtagt gccgacaaga caatctttat cttcaacagc | 120 |
| atctcgctgc gtgaaccccc caaagaccag gtgcttgcac actttggctg gctgctggc | 180 |
| ccaaaacctg ctcagattga tcgtcaggct tcgtcgtcc ttatcgatcg cccgtccggc | 240 |
| ttagtgcatg aaattatcgt gtccttaacg acgtccagcg tggtttcatg gaaccgtaaa | 300 |
| caaggcgtac aaccaacgct gcacgttcag gagatgcttg aggcagaaga ggtgatgttg | 360 |
| aaagatgaac gtgtcatcga ggaatgccgc aaattaggaa tcgaagatat gagtcttgtg | 420 |
| tttgccgaca cgtggggagt gggctggcat aaaacaaagg gcaaacgtct tatgcaggct | 480 |
| tgatgtata tgcgtacgag ccctgatgat aaccagtatg cgcatccctt ggactttaca | 540 |
| ccattatacg atgtcaatga gcaaaaagtc atcgatgtgc ttgtcgccaa gcgccgtaac | 600 |
| tcaaagttcg aacgtcccgt catccccgt gcggaccacc agtttctgcc ggaacacctg | 660 |
| ggggagggca atttgcgcaa agatatt | 687 |

<210> SEQ ID NO 33
<211> LENGTH: 702
<212> TYPE: DNA
<213> ORGANISM: Syncephalastrum racemosum

<400> SEQUENCE: 33

| | |
|---|---|
| ttgcgcaaag atattaagcc cattgaaatt attcaaccag agggtgtcag ctttcaaatc | 60 |
| cgcgggcatg agatcgactg gcaaaagtgg aaccttcaca tcggattcaa ttatcgcgag | 120 |
| ggacttgtta tcagcaacgt tagttacaaa gacatggacg gcacggtacg tcctgtattc | 180 |
| tatcgcgtat ctctggcaga atggtagtc ccctacgcga atccttacga accctacaac | 240 |
| cataagatgg ccttcgatgt aggagagtac ggcctgggca acttgacgaa cagtttagaa | 300 |
| ctgggatgtg attgcgtagg gagcatcttc tacatggacg gggtctgttc ggatctgaag | 360 |
| ggagacgcgt gggtcatccc caatgcgatc tgcatccatg aagaggacac cgggttattg | 420 |
| ttcaagcaca cagattttcg caacaacaaa gcgcactcag ctcgtagtcg tcgtttggtt | 480 |
| atttcccata tcgttaccgc cgccaattat gattatgggt tgtattacta ttttaccag | 540 |
| gatggtactt tccaatacga agtcaaggcc acaggagaac ttaacactca cgtcttagcg | 600 |
| gaggatgaga accccgctcc ctacggaaca attgtgcac ctcagatcga tgcgcaacac | 660 |
| caccaacact tattttccat gcgcattgat ccgatggtag ac | 702 |

<210> SEQ ID NO 34
<211> LENGTH: 693
<212> TYPE: DNA
<213> ORGANISM: Syncephalastrum racemosum

<400> SEQUENCE: 34

| | |
|---|---|
| gatccgatgg tagacggacc gactaactcg gtggctcagg tagacgtggt agctagcgac | 60 |

-continued

```
ttgcctgtcg gacaccctga caacgccgtg gggaatgcat tctcgccaat taccacaatc    120
tatgcgaaca cagacgaggc acaagcgcgc gccaatggag agacttcccg ttactggaag    180
atcatcaacg aagataaaat tcacccatat acacgtgaac ctgttggttt taagcttatg    240
tgtccgaaca caccacccat gctgccgaaa ccgggatcca ttgcgtatga gcgtgcagtc    300
ttcgcttcga aaacggtctg ggttaccccg tacgacgcag aacaattgtt cccaggtggt    360
ttctactgtt atcagtcgga ccccgccgat cgtttaggcc tgccggagtg gacaaaaggg    420
aaaaaggacg taagaacaa ggacattgtc ctgtggttaa cgttcgggct gacccacatt    480
ccgcgtgtgg aagactttcc cattatgccc gtagaaacct gcggctttat gcttaaaccc    540
tgtaacttct tccttgcaaa cccaggaatt gacatcccgg cctccgataa gcactcgact    600
aaatcggcgt acgctcatgc gcttacgaat ggagccaatg ggactgggaa cggtagcaca    660
aacggctcca gctgctgcaa taagaattac taa                                  693
```

<210> SEQ ID NO 35
<211> LENGTH: 683
<212> TYPE: PRT
<213> ORGANISM: Syncephalastrum racemosum

<400> SEQUENCE: 35

```
Met Thr Leu Pro Thr Thr Ile His Pro Leu Asp Pro Leu Ser Pro Glu
1               5                   10                  15

Glu Ile Arg His Val Ser Glu Ile Ile Arg Lys Gln Arg Ala Ala Asp
                20                  25                  30

Glu Thr Thr Tyr Ile Phe Asn Ser Ile Ala Leu Arg Glu Pro Pro Lys
            35                  40                  45

Glu Gln Ile Leu Ala His Phe Gly Trp Thr Asp Gly Pro Lys Pro Val
        50                  55                  60

Gln Ile Asp Arg Gln Ala Phe Ala Val Leu Ile Asp Arg Pro Ser Gly
65                  70                  75                  80

Leu Val His Glu Ile Ile Val Ser Ile Thr Thr Ala Ser Ile Val Ser
                85                  90                  95

Trp Glu Thr Lys Glu Gly Val Gln Pro Thr Leu His Val Gln Glu Met
                100                 105                 110

Leu Glu Ala Glu Gln Val Met Leu Lys Asp Glu Arg Val Ile Glu Glu
            115                 120                 125

Cys Arg Lys Leu Gly Ile Glu Asp Met Ser Met Val Phe Ala Asp Thr
        130                 135                 140

Trp Gly Val Gly Trp His Lys Thr Lys Gly Lys Arg Leu Met Gln Ala
145                 150                 155                 160

Leu Met Tyr Met Arg Thr Ser Pro Asp Asp Asn Gln Tyr Ala His Pro
                165                 170                 175

Leu Asp Phe Thr Pro Leu Tyr Asp Val Asn Glu Gln Lys Val Ile Asp
            180                 185                 190

Val Leu Val Ala Lys Arg Arg Asn Ser Lys Phe Glu Arg Pro Val Ile
        195                 200                 205

Pro Arg Ala Asp Arg Gln Phe Leu Pro Glu His Leu Gly Glu Glu Asn
    210                 215                 220

Leu Arg Lys Asp Ile Lys Pro Ile Glu Ile Thr Gln Pro Gln Gly Val
225                 230                 235                 240

Ser Phe Gln Ile Arg Gly His Glu Ile Asp Trp Gln Lys Trp Asn Leu
                245                 250                 255

His Val Gly Phe Asn Tyr Arg Glu Gly Leu Val Ile Asn Asn Val Ser
```

-continued

```
                260                 265                 270
Tyr Lys Asp Met Asp Gly Thr Val Arg Pro Met Phe Tyr Arg Val Ser
            275                 280                 285

Leu Ala Glu Met Val Val Pro Tyr Ala Asn Pro Tyr Glu Pro Tyr Asn
290                 295                 300

His Lys Met Ala Phe Asp Val Gly Glu Tyr Gly Leu Gly Asn Leu Thr
305                 310                 315                 320

Asn Ser Leu Glu Leu Gly Cys Asp Cys Val Gly Ser Ile Phe Tyr Met
            325                 330                 335

Asp Gly Val Cys Ser Asp Ile Lys Gly Asp Ala Trp Val Ile Pro Asn
            340                 345                 350

Ala Ile Cys Ile His Glu Glu Asp Thr Gly Leu Leu Phe Lys His Thr
            355                 360                 365

Asp Phe Arg Asn Asn Lys Ala His Ser Ala Arg Ser Arg Arg Leu Val
370                 375                 380

Ile Ser His Ile Val Thr Ala Ala Asn Tyr Asp Tyr Gly Leu Tyr Tyr
385                 390                 395                 400

Tyr Phe Tyr Gln Asp Gly Thr Phe Gln Tyr Glu Val Lys Ala Thr Gly
            405                 410                 415

Glu Leu Asn Thr His Val Leu Ala Glu Asp Glu Pro Ala Pro Tyr
            420                 425                 430

Gly Thr Ile Val Ala Pro Gln Val Asp Ala Gln His His Gln His Leu
            435                 440                 445

Phe Ser Met Arg Ile Asp Pro Met Val Asp Gly Pro Thr Asn Ser Val
450                 455                 460

Ala Gln Val Asp Val Val Ala Ser Asp Leu Pro Val Gly His Pro Asp
465                 470                 475                 480

Asn Ala Val Gly Asn Ala Phe Ser Pro Val Thr Thr Ile Tyr Ala Asp
            485                 490                 495

Thr Asp Glu Ala Arg Ala Arg Ala Asn Gly Glu Thr Ser Arg Tyr Trp
            500                 505                 510

Lys Ile Ile Asn Glu Thr Arg Ile His Pro Tyr Thr Lys Glu Pro Val
            515                 520                 525

Gly Phe Lys Leu Met Cys Pro Asn Thr Pro Met Leu Pro Lys Pro
530                 535                 540

Gly Ser Ile Ala Tyr Glu Arg Ala Val Phe Ala Ser Asn Thr Val Trp
545                 550                 555                 560

Val Thr Pro Tyr Asp Ala Glu Gln Leu Phe Pro Gly Gly Phe Tyr Cys
            565                 570                 575

Tyr Gln Ser Asp Pro Ala Asp Arg Leu Gly Leu Pro Glu Trp Thr Arg
            580                 585                 590

Glu Lys Lys Asp Val Lys Asn Lys Asp Ile Val Leu Trp Leu Thr Phe
            595                 600                 605

Gly Leu Thr His Ile Pro Arg Val Glu Asp Phe Pro Ile Met Pro Val
            610                 615                 620

Glu Thr Cys Gly Phe Met Leu Lys Pro Cys Asn Phe Phe Leu Ala Asn
625                 630                 635                 640

Pro Gly Ile Asp Ile Pro Ala Ser Asp Arg His Ser Ser Lys Ser Ala
            645                 650                 655

Tyr Ala Pro Ala Val Ala Asn Gly Glu Tyr Gly Ile Thr Asn Gly Thr
            660                 665                 670

Thr Asn Gly Ser Ser Cys Cys Ser Lys Gly His
            675                 680
```

<210> SEQ ID NO 36
<211> LENGTH: 2052
<212> TYPE: DNA
<213> ORGANISM: Syncephalastrum racemosum

<400> SEQUENCE: 36

```
atgacactcc ccactactat ccacccattg gatccgctga gtcccgagga aattcgtcat      60
gttagtgaga tcatccgaaa acaacgggcc gccgacgaaa caacctatat attcaactcc     120
atagcactcc gtgaaccgcc taaggaacag atcctcgcgc atttcggttg dacagatgga     180
cctaaaccag ttcagattga tcggcaagcg ttcgctgtcc tcatagaccg cccttcggga     240
ttggtccatg agataattgt gagcatcacg accgcctcca tagtttcctg ggagactaag     300
gaaggcgttc agcccactct gcatgtacaa gaaatgctgg aggcagagca agtgatgctc     360
aaggatgaac gtgtcatcga ggaatgccga aaactcggta ttgaagatat gtcgatggta     420
ttcgctgata catggggagt gggttggcac aaaaccaagg gcaaacgatt gatgcaagcc     480
ctcatgtaca tgcgcactag tccagacgac aatcagtatg cccatcccct ggatttcaca     540
cccctgtata tgtaaacga gcaaaaagtg atagatgttc tggtggcgaa aaggcgaaat     600
tcgaaattcg agcgaccagt cattccacga gccgaccgcc agttcttgcc agagcacctc     660
ggagaggaaa atctccgcaa agatataaaa ccgattgaaa ttacccagcc caaggtgtc      720
agtttccaga ttaggggcca cgagatcgac tggcaaaagt ggaacctgca tgtcggattc     780
aattatcgag aaggcctcgt aattaacaat gtcagttaca aggacatgga tggcactgtt     840
aggcccatgt tctatcgagt gagtctggca gaaatggtcg tcccgtatgc gaacccgtac     900
gagccttaca atcacaagat ggcttttgac gtgggtgaat atggactcgg taacctcaca     960
aatagcttgg agctcggatg tgattgtgta ggtagtatat tttatatgga cggagtgtgt    1020
agcgacatca agggtgacgc ttgggtaatt cccaatgcga tttgcatcca cgaagaagac    1080
acgggcctcc tgttcaagca cactgatttt aggaacaata aggcgcatag cgctcgaagc    1140
cgcaggctgg tgatttccca catcgtcaca gcggcaaatt acgattatgg cctgtactat    1200
tattttatc aggacggtac atttcagtac gaagtgaagg cgactggaga gctcaacact    1260
cacgtattgg cggaagacga agaccctgca ccttacggca ctattgttgc tcctcaggta    1320
gacgcgcagc atcatcaaca cctctttagt atgcgtattg atccaatggt agatggacct    1380
accaatagtg tggctcaagt agacgtcgtg gccagcgatt tgcccgtcgg tcatcccgat    1440
aacgccgtgg gtaacgcgtt cagtccggtt acaacgattt acgcagacac tgacgaagcg    1500
cgggcacgag ctaatggaga aacctcccgc tactggaaga taattaacga aactcgcata    1560
catccctaca ctaaagaacc agtaggtttc aaactcatgt gccctaatac acctccgatg    1620
ctcccgaaac cgggaagcat tgcgtacgaa cgcgcagtat ttgcctcgaa tacagtttgg    1680
gttactccgt acgatgccga gcaactgttt ccgggtggat tctactgcta tcaaagcgat    1740
cccgccgacc gcctgggtct gccggagtgg actagggaga agaaggacgt gaaaaacaag    1800
gacatagttc tgtggctgac gtttggtctc actcatattc ccagggttga ggattttcca    1860
atcatgccgg tagaaacatg tggattcatg ctgaagcctt gtaatttctt cttggcaaac    1920
ccggaattg atatccctgc tagcgatcgt catagtagta agtccgcata tgcaccggcg    1980
gttgcaaacg gagaatatgg cataacaaat ggaacgacga atggctcgtc ctgttgcagc    2040
aagggacact aa                                                         2052
```

<210> SEQ ID NO 37
<211> LENGTH: 687
<212> TYPE: DNA
<213> ORGANISM: Syncephalastrum racemosum

<400> SEQUENCE: 37

```
atgacactcc ccactactat ccacccattg gatccgctga gtcccgagga aattcgtcat    60
gttagtgaga tcatccgaaa acaacgggcc gccgacgaaa caacctatat attcaactcc   120
atagcactcc gtgaaccgcc taaggaacag atcctcgcgc atttcggttg acagatgga    180
cctaaaccag ttcagattga tcggcaagcg ttcgctgtcc tcatagaccg cccttcggga   240
ttggtccatg agataattgt gagcatcacg accgcctcca tagtttcctg ggagactaag   300
gaaggcgttc agcccactct gcatgtacaa gaaatgctgg aggcagagca agtgatgctc   360
aaggatgaac gtgtcatcga ggaatgccga aaactcggta ttgaagatat gtcgatggta   420
ttcgctgata catggggagt gggttggcac aaaaccaagg gcaaacgatt gatgcaagcc   480
ctcatgtaca tgcgcactag tccagacgac aatcagtatg cccatcccct ggatttcaca   540
cccctgtatg atgtaaacga gcaaaaagtg atagatgttc tggtggcgaa aaggcgaaat   600
tcgaaattcg agcgaccagt cattccacga gccgaccgcc agttcttgcc agagcacctc   660
ggagaggaaa atctccgcaa agatata                                      687
```

<210> SEQ ID NO 38
<211> LENGTH: 705
<212> TYPE: DNA
<213> ORGANISM: Syncephalastrum racemosum

<400> SEQUENCE: 38

```
ctccgcaaag atataaaacc gattgaaatt acccagcccc aaggtgtcag tttccagatt    60
aggggccacg agatcgactg gcaaaagtgg aacctgcatg tcggattcaa ttatcgagaa   120
ggcctcgtaa ttaacaatgt cagttacaag gacatggatg gcactgttag gcccatgttc   180
tatcgagtga gtctggcaga aatggtcgtc ccgtatgcga acccgtacga gccttacaat   240
cacaagatgg cttttgacgt gggtgaatat ggactcggta acctcacaaa tagcttggag   300
ctcggatgtg attgtgtagg tagtatattt tatatggacg gagtgtgtag cgacatcaag   360
ggtgacgctt gggtaattcc caatgcgatt tgcatccacg aagaagacac gggcctcctg   420
ttcaagcaca ctgattttag gaacaataag gcgcatagcg ctcgaagccg caggctggtg   480
atttcccaca tcgtcacagc ggcaaattac gattatggcc tgtactatta ttttttatcag  540
gacggtacat ttcagtacga agtgaaggcg actggagagc tcaacactca cgtattggcg   600
gaagacgaag accctgcacc ttacggcact attgttgctc ctcaggtaga cgcgcagcat   660
catcaacacc tctttagtat gcgtattgat ccaatggtag atgga                  705
```

<210> SEQ ID NO 39
<211> LENGTH: 690
<212> TYPE: DNA
<213> ORGANISM: Syncephalastrum racemosum

<400> SEQUENCE: 39

```
ccaatggtag atggacctac caatagtgtg gctcaagtag acgtcgtggc cagcgatttg    60
cccgtcggtc atcccgataa cgccgtgggt aacgcgttca gtccggttac aacgatttac   120
gcagacactg acgaagcgcg ggcacagagct aatggagaaa cctcccgcta ctggaagata  180
attaacgaaa ctcgcataca tccctacact aaagaaccag taggtttcaa actcatgtgc   240
```

```
cctaatacac ctccgatgct cccgaaaccg ggaagcattg cgtacgaacg cgcagtattt    300
gcctcgaata cagtttgggt tactccgtac gatgccgagc aactgttttcc gggtggattc   360 tactgctatc aaagcgatcc cgccgaccgc ctgggtctgc cggagtggac tagggagaag    420
aaggacgtga aaacaagga catagttctg tggctgacgt ttggtctcac tcatattccc    480
agggttgagg attttccaat catgccggta gaaacatgtg gattcatgct gaagccttgt    540
aatttcttct tggcaaaccc gggaattgat atccctgcta gcgatcgtca tagtagtaag    600
tccgcatatg caccggcggt tgcaaacgga gaatatggca taacaaatgg aacgacgaat    660
ggctcgtcct gttgcagcaa gggacactaa                                    690
```

```
<210> SEQ ID NO 40
<211> LENGTH: 30
<212> TYPE: DNA
<213> ORGANISM: Artificial Sequence
<220> FEATURE:
<223> OTHER INFORMATION: pKK223-3 HindIII 3Fw

<400> SEQUENCE: 40
aagcttggct gttttggcgg atgagagaag                                    30

<210> SEQ ID NO 41
<211> LENGTH: 30
<212> TYPE: DNA
<213> ORGANISM: Artificial Sequence
<220> FEATURE:
<223> OTHER INFORMATION: pKK223-3 EcoRI 5Rv

<400> SEQUENCE: 41
gaattctgtt tcctgtgtga aattgttatc                                    30

<210> SEQ ID NO 42
<211> LENGTH: 15
<212> TYPE: DNA
<213> ORGANISM: Artificial Sequence
<220> FEATURE:
<223> OTHER INFORMATION: 5' end side of the agpeaox_1-325

<400> SEQUENCE: 42
caggaaacag aattc                                                    15

<210> SEQ ID NO 43
<211> LENGTH: 15
<212> TYPE: DNA
<213> ORGANISM: Artificial Sequence
<220> FEATURE:
<223> OTHER INFORMATION: 3' end side of agpeaox_321-638

<400> SEQUENCE: 43
aagcttggct gtttt                                                    15

<210> SEQ ID NO 44
<211> LENGTH: 15
<212> TYPE: DNA
<213> ORGANISM: Artificial Sequence
<220> FEATURE:
<223> OTHER INFORMATION: 3' end of agpeaox_1-325

<400> SEQUENCE: 44
atcacgtacc tgtcc                                                    15

<210> SEQ ID NO 45
```

```
<211> LENGTH: 15
<212> TYPE: DNA
<213> ORGANISM: Artificial Sequence
<220> FEATURE:
<223> OTHER INFORMATION: 5' end of agpeaox_321-638

<400> SEQUENCE: 45
atcacgtacc tgtcc                                                    15

<210> SEQ ID NO 46
<211> LENGTH: 15
<212> TYPE: DNA
<213> ORGANISM: Artificial Sequence
<220> FEATURE:
<223> OTHER INFORMATION: 3' end of lcaox_frag1 and 5' end of lcaox_frag2

<400> SEQUENCE: 46
cccgaacacc ttggt                                                    15

<210> SEQ ID NO 47
<211> LENGTH: 15
<212> TYPE: DNA
<213> ORGANISM: Artificial Sequence
<220> FEATURE:
<223> OTHER INFORMATION: 3' end of lcaox_frag2 and 5' end of lcaox_frag3

<400> SEQUENCE: 47
cagcatcatc aacat                                                    15

<210> SEQ ID NO 48
<211> LENGTH: 15
<212> TYPE: DNA
<213> ORGANISM: Artificial Sequence
<220> FEATURE:
<223> OTHER INFORMATION: 3' end of lrhp_frag1 and at 5' end of
      lrhp_frag2

<400> SEQUENCE: 48
catttagggc aagat                                                    15

<210> SEQ ID NO 49
<211> LENGTH: 15
<212> TYPE: DNA
<213> ORGANISM: Artificial Sequence
<220> FEATURE:
<223> OTHER INFORMATION: 3' end of lrhp_frag2 and at 5' end of
      lrhp_frag3

<400> SEQUENCE: 49
caccatcaac atttg                                                    15

<210> SEQ ID NO 50
<211> LENGTH: 15
<212> TYPE: DNA
<213> ORGANISM: Artificial Sequence
<220> FEATURE:
<223> OTHER INFORMATION: 3' end of sraox3925-frag1 and 5' end of
      sraox3925-frag2

<400> SEQUENCE: 50
cagtttttac cagag                                                    15

<210> SEQ ID NO 51
<211> LENGTH: 15
<212> TYPE: DNA
<213> ORGANISM: Artificial Sequence
<220> FEATURE:
```

```
<223> OTHER INFORMATION: 3' end of sraox3925-frag2 and 5' end of
      sraox3925-frag3

<400> SEQUENCE: 51
gtcgtaggcc agcat                                                      15

<210> SEQ ID NO 52
<211> LENGTH: 15
<212> TYPE: DNA
<213> ORGANISM: Artificial Sequence
<220> FEATURE:
<223> OTHER INFORMATION: 3' end of sraox3926-frag1 and 5' end of
      sraox3926-frag2

<400> SEQUENCE: 52
ttgcgcaaag atatt                                                      15

<210> SEQ ID NO 53
<211> LENGTH: 15
<212> TYPE: DNA
<213> ORGANISM: Artificial Sequence
<220> FEATURE:
<223> OTHER INFORMATION: 3' end of sraox3926-frag2 and 5' end of
      sraox3926-frag3

<400> SEQUENCE: 53
gatccgatgg tagac                                                      15

<210> SEQ ID NO 54
<211> LENGTH: 15
<212> TYPE: DNA
<213> ORGANISM: Artificial Sequence
<220> FEATURE:
<223> OTHER INFORMATION: 3' end of sreaox_frag1 and at 5' end of
      sreaox_frag2

<400> SEQUENCE: 54
ctccgcaaag atata                                                      15

<210> SEQ ID NO 55
<211> LENGTH: 15
<212> TYPE: DNA
<213> ORGANISM: Artificial Sequence
<220> FEATURE:
<223> OTHER INFORMATION: 3' end of sreaox_frag2 and at 5' end of
      sreaox_frag3

<400> SEQUENCE: 55
ccaatggtag atgga                                                      15
```